US010533058B2

(12) United States Patent
Flygare et al.

(10) Patent No.: US 10,533,058 B2
(45) Date of Patent: Jan. 14, 2020

(54) PEPTIDOMIMETIC COMPOUNDS AND ANTIBODY-DRUG CONJUGATES THEREOF

(71) Applicants: GENENTECH INC., South San Francisco, CA (US); MEDIMMUNE LIMITED, Cambridge, Camdridgeshire (GB)

(72) Inventors: John Flygare, South San Francisco, CA (US); Janet Gunzner-Toste, South San Francisco, CA (US); Thomas Pillow, South San Francisco, CA (US); Brian Safina, South San Francisco, CA (US); Vishal Verma, South San Francisco, CA (US); Binqing Wei, South San Francisco, CA (US); Guiling Zhao, South San Francisco, CA (US); Leanna Staben, South San Francisco, CA (US); Philip Wilson Howard, Cambridge (GB); Luke Masterson, Cambridge (GB)

(73) Assignees: Genentech Inc., South San Francisco, CA (US); Medimmune Limited, Cambridge, Cambridgesh (GB)

( * ) Notice: Subject to any disclaimer, the term of this patent is extended or adjusted under 35 U.S.C. 154(b) by 445 days.

(21) Appl. No.: 15/104,388

(22) PCT Filed: Dec. 16, 2014

(86) PCT No.: PCT/US2014/070493
§ 371 (c)(1),
(2) Date: Jun. 14, 2016

(87) PCT Pub. No.: WO2015/095124
PCT Pub. Date: Jun. 25, 2015

(65) Prior Publication Data
US 2016/0310611 A1 Oct. 27, 2016

Related U.S. Application Data

(60) Provisional application No. 61/916,675, filed on Dec. 16, 2013.

(51) Int. Cl.
*A61K 47/68* (2017.01)
*A61K 31/5517* (2006.01)
*C07K 16/30* (2006.01)
*C07K 16/28* (2006.01)

(52) U.S. Cl.
CPC ...... *C07K 16/3092* (2013.01); *A61K 31/5517* (2013.01); *A61K 47/6803* (2017.08); *A61K 47/6851* (2017.08); *A61K 47/6867* (2017.08); *A61K 47/6869* (2017.08); *A61K 47/6889* (2017.08); *C07K 16/2851* (2013.01); *C07K 16/30* (2013.01); *C07K 16/3061* (2013.01); *C07K 16/3069* (2013.01); *C07K 2317/24* (2013.01); *C07K 2317/51* (2013.01); *C07K 2317/515* (2013.01); *C07K 2317/56* (2013.01)

(58) Field of Classification Search
None
See application file for complete search history.

(56) References Cited

U.S. PATENT DOCUMENTS

| 6,214,345 | B1 | 4/2001 | Firestone et al. |
| 7,521,541 | B2 | 4/2009 | Eigenbrot et al. |
| 7,855,275 | B2 | 12/2010 | Eigenbrot et al. |
| 8,309,300 | B2 | 11/2012 | Junutula et al. |
| 9,000,130 | B2 | 4/2015 | Bhakta et al. |
| 2007/0092940 | A1 | 4/2007 | Eigenbrot et al. |
| 2009/0175865 | A1 | 7/2009 | Eigenbrot et al. |
| 2010/0003766 | A1 | 1/2010 | Eigenbrot et al. |
| 2010/0111856 | A1 | 5/2010 | Gill et al. |
| 2011/0137017 | A1 | 6/2011 | Eigenbrot et al. |
| 2011/0256157 | A1 | 10/2011 | Howard et al. |
| 2011/0301334 | A1 | 12/2011 | Bhakta et al. |
| 2013/0028917 | A1 | 1/2013 | Howard et al. |
| 2013/0266595 | A1 | 10/2013 | Flygare et al. |
| 2014/0288280 | A1 | 9/2014 | Bhakta et al. |
| 2014/0294868 | A1 | 10/2014 | Howard et al. |
| 2014/0356375 | A1 | 12/2014 | Brown et al. |
| 2014/0356376 | A1 | 12/2014 | Brown et al. |
| 2015/0017094 | A1 | 1/2015 | Gill et al. |
| 2015/0017188 | A1 | 1/2015 | Eigenbrot et al. |
| 2015/0165063 | A1 | 6/2015 | Flygare et al. |
| 2015/0366985 | A1 | 12/2015 | Brown et al. |
| 2016/0074527 | A1 | 3/2016 | Flygare et al. |
| 2016/0074529 | A1 | 3/2016 | Brown et al. |
| 2016/0075787 | A1 | 3/2016 | Zheng et al. |
| 2016/0130358 | A1 | 5/2016 | Bhakta et al. |
| 2016/0279260 | A1 | 9/2016 | Flygare et al. |
| 2016/0279261 | A1 | 9/2016 | Lee et al. |
| 2016/0354485 | A1 | 12/2016 | Flygare et al. |

FOREIGN PATENT DOCUMENTS

| WO | 2006/034488 | 3/2006 |
| WO | 2011/056983 | 5/2011 |
| WO | 2011/130598 | 10/2011 |
| WO | WO-2011130598 A1 * | 10/2011 ........... C07D 487/04 |
| WO | 2011/156328 | 12/2011 |
| WO | 2013/041606 | 3/2013 |
| WO | 2013/053873 | 4/2013 |
| WO | 2013/055987 | 4/2013 |
| WO | 2013/055990 | 4/2013 |

(Continued)

OTHER PUBLICATIONS

Vippagunta et al. "Crystalline Solids," Advanced Drug Delivery Reviews, 2001, 48, pp. 18.*

(Continued)

*Primary Examiner* — Mark Halvorson
*Assistant Examiner* — Kauser M Akhoon
(74) *Attorney, Agent, or Firm* — Casimir Jones, S.C.; Melissa E. Kolom

(57) ABSTRACT

This invention relates to peptidomimetic linkers and antibody drug conjugates thereof, pharmaceutical compositions containing them, and to their use in therapy for the prevention treatment of cancer.

7 Claims, 3 Drawing Sheets

Specification includes a Sequence Listing.

(56) References Cited

FOREIGN PATENT DOCUMENTS

| WO | 2013/177055 | 11/2013 |
|----|-------------|---------|
| WO | 2014/159981 | 10/2014 |
| WO | 2014/193722 | 12/2014 |
| WO | 2014/194247 | 12/2014 |
| WO | 2015/023355 | 2/2015 |
| WO | 2015/095212 | 6/2015 |
| WO | 2015/095223 | 6/2015 |
| WO | 2015/095227 | 6/2015 |
| WO | 2016/040856 | 3/2016 |
| WO | 2016/040868 | 3/2016 |
| WO | 2016/044560 | 3/2016 |
| WO | 2016/090038 | 9/2016 |
| WO | 2016/090040 | 9/2016 |
| WO | 2016/090050 | 9/2016 |

OTHER PUBLICATIONS

Doronina et al., "Novel Peptide Linkers for Highly Potent Antibody-Auristatin Conjugate," Bioconjugate Chem., 2008, 19(10):1960-1963.
Ducry et al., "Antibody-Drug Conjugates: Linking Cytotoxic Payloads to Monoclonal Antibodies," Bioconjugate Chem, 2010, 21:5-13.
International Search Report and Written Opinion for Application No. PCT/US2014/070493 dated Mar. 26, 2015.
Nolting, "Linker Technologies for Antibody-Drug Conjugates," Methods in Molecular Biology, 2013, Chapter 5, 1045:71-100.

* cited by examiner

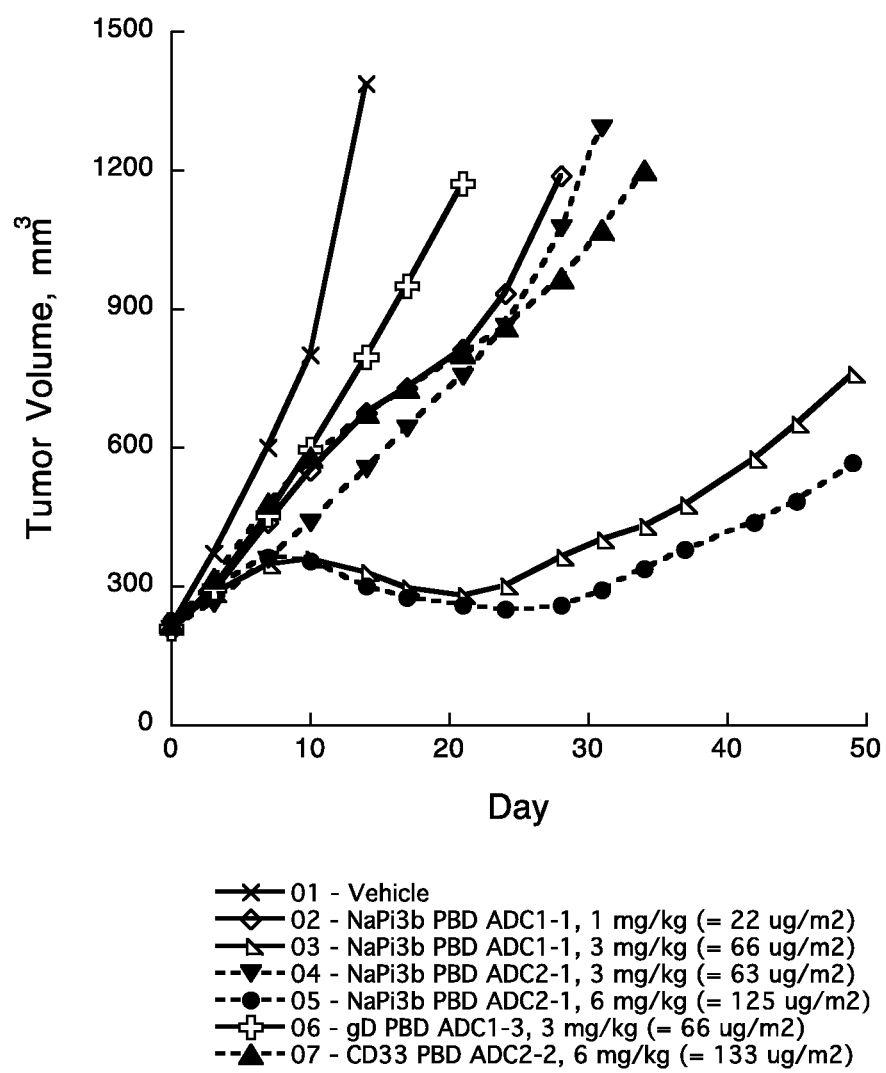
Figure 1 (OVCAR3X2.1)

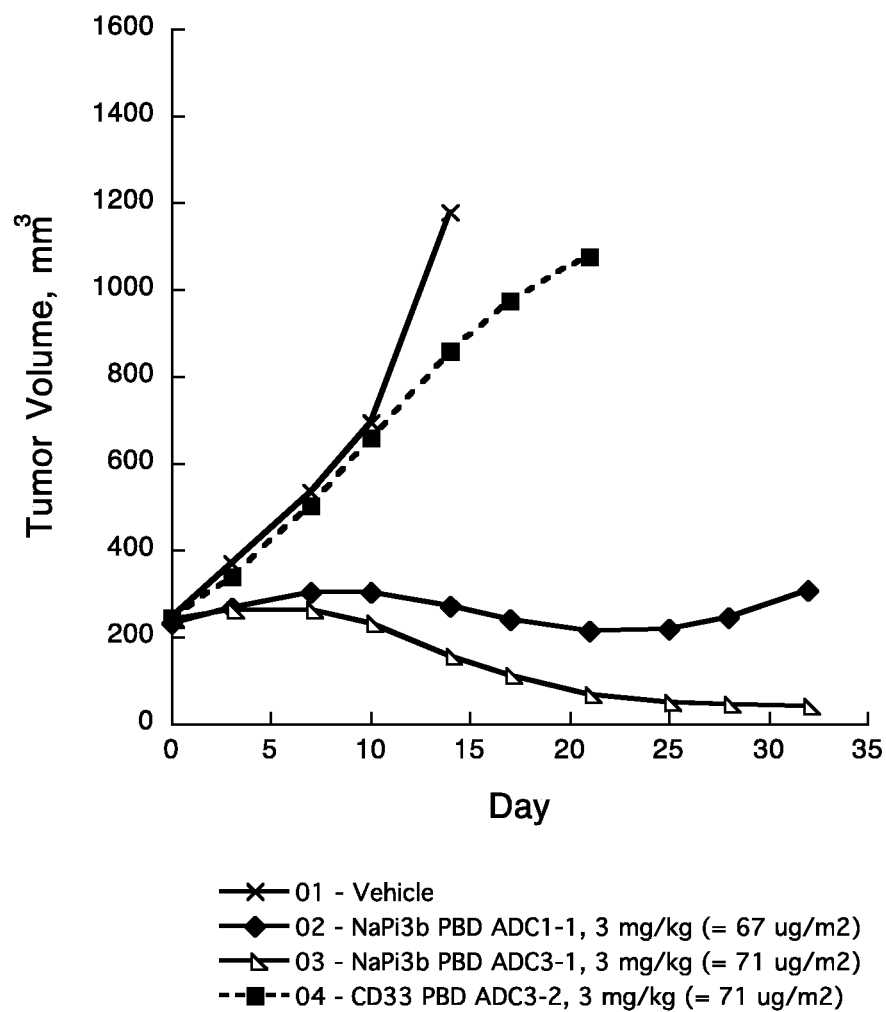
Figure 2 (OVCAR3X2.1)

Figure 3 (EOL-1)
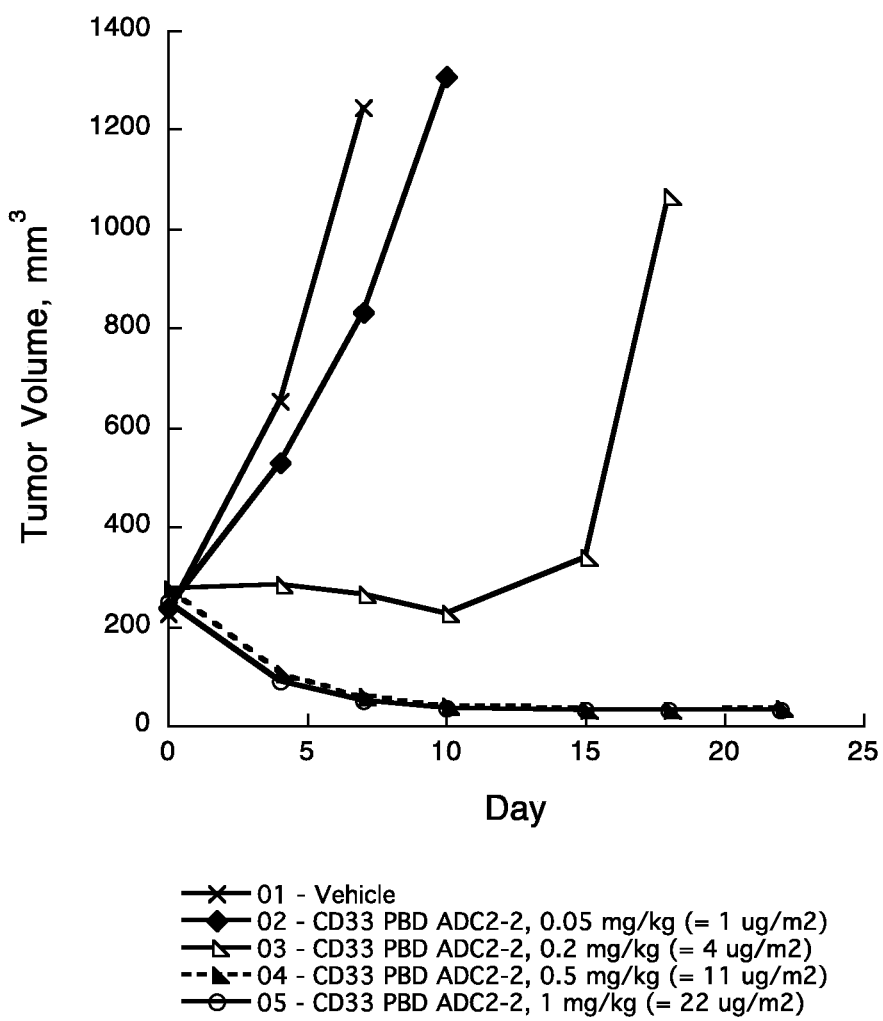

PEPTIDOMIMETIC COMPOUNDS AND ANTIBODY-DRUG CONJUGATES THEREOF

FIELD OF INVENTION

This invention relates to novel peptidomimetic compounds which are useful as linkers of antibody-drug conjugates (ADC). This invention also relates to ADCs containing peptidomimetic linkers and pyrrolobenzodiazepines (PBD). This invention also relates to methods of treating diseases in humans.

BACKGROUND OF THE INVENTION

The use of monoclonal antibodies (mABs) to deliver anticancer drugs directly to tumor cells has attracted a great deal of focus in recent years. Two new antibody-drug conjugates have been approved by the FDA for the treatment of cancer. Adcetris® (brentuximab vedotin) is a CD30-directed antibody-drug conjugate (ADC) indicated for the treatment of relapsed or refractory Hodgkin lymphoma and systemic anaplastic large cell lymphoma (ALCL). Kadcyla® (ado-trastuzumab emtansine), is a new therapy approved for patients with HER2-positive, late-stage (metastatic) breast cancer. To obtain a therapeutic both potent anti-tumor activity and acceptable therapeutic index in an ADC, several aspects of design may be optimized. Particularly, it is well known that the chemical structure of the linker can have significant impact on both the efficacy and the safety of ADC (Ducry & Stump, Bioconjugate Chem, 2010, 21, 5-13). Choosing the right linker influences proper drug delivery to the intended cellular compartment of cancer cells. Linkers can be generally divided into two categories: cleavable (such as peptide, hydrzone, or disulfide) or non-cleavable (such as thioether). Peptide linkers, such as Valine-Citrulline (Val-Cit), that can be hydrolyzed by lysosomal enzymes (such as Cathepsin B) have been used to connect the drug with the antibody (U.S. Pat. No. 6,214, 345). They have been particularly useful, due in part to their relative stability in systemic circulation and the ability to efficiently release the drug in tumor. ADCs containing the Val-Cit linker have been shown to be relatively stable in vivo (t1/2 for drug release ~7 days (Doronina et al (2008), Bioconjugate Chem., 19, 1960-1963). However, the chemical space represented by natural peptides is limited; therefore, it is desirable to have a variety of non-peptide linkers which act like peptides and can be effectively cleaved by lysosomal proteases. The greater diversity of non-peptide structures may yield novel, beneficial properties that are not afforded by the peptide linkers. Provided herein are different types of non-peptide linkers for ADC that can be cleaved by lysosomal enzymes.

SUMMARY OF THE INVENTION

This invention relates to antibody-drug conjugates represented by Formula (I)

Ab-(L-D)$_p$,

Ab is an antibody:
L is a peptidomimetic linker represented by the following formula -Str-(PM)-Spwherein
Str is a stretcher unit covalently attached to Ab;
Sp is a bond or spacer unit covalently attached to a drug moiety;

PM is a non-peptide chemical moiety selected from the group consisting of:

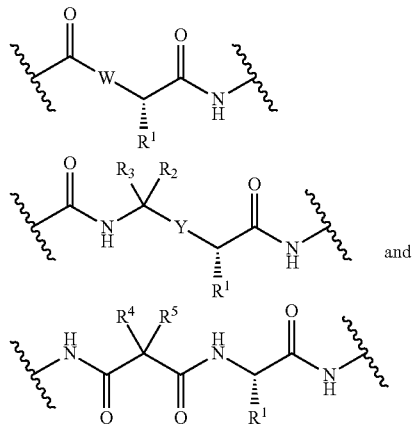

and

W is —NH-heterocycloalkyl- or heterocycloalkyl;
Y is heteroaryl, aryl, —C(O)$C_1$-$C_6$alkylene, $C_1$-$C_6$alkenyl, $C_1$-$C_6$alkylenyl or —$C_1$-$C_6$alkylene-NH—;
each $R^1$ is independently $C_1$-$C_{10}$alkyl, $C_1$-$C_{10}$alkenyl, ($C_1$-$C_{10}$alkyl)NHC(NH)$NH_2$ or ($C_1$-$C_{10}$alkyl)NHC(O)$NH_2$;
$R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl;
$R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ may form a $C_3$-$C_7$cycloalkyl ring;
p is an integer from 1 to 8;
D is a drug moiety of formula A or of formula B

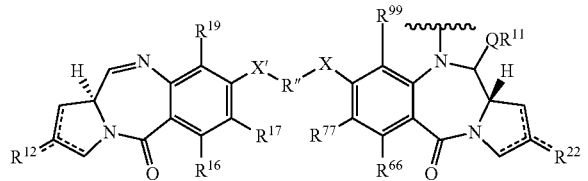

A

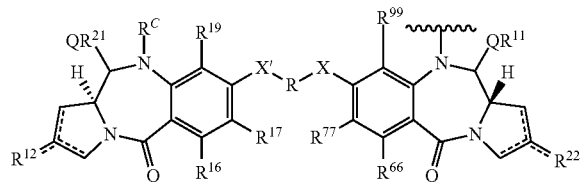

B and salts and solvates thereof, wherein:
the wavy line indicates the covalent attachment site to the linker;
the dotted lines indicate the optional presence of a double bond between C1 and C2 or C2 and C3;
$R^{22}$ is independently selected from H, OH, =O, =$CH_2$, CN, $R^m$, O $R^m$, =CH—$R^m$, =C($R^D$)$_2$, O—$SO_2$—$R^m$, $CO_2$ $R^m$ and CO $R^m$, and optionally further selected from halo or dihalo, wherein $R^D$ is independently selected from $R^m$, $CO_2$ $R^m$, CO $R^m$, CHO, $CO_2$H, and halo;
$R^{66}$ and $R^{99}$ are independently selected from H, $R^m$, OH, O $R^m$, SH, S $R^m$, $NH_2$, NH $R^m$, N $R^m$ $R^p$, $NO_2$, Me$_3$Sn and halo;

$R^{77}$ is independently selected from H, $R^m$, OH, O $R^m$, SH, S $R^m$, $NH_2$, NH $R^m$, N $R^m$ $R^p$, $NO_2$. $Me_3Sn$ and halo;

Q is independently selected from O, S and NH;

$R^{11}$ is either H, or $R^m$ or, where Q is O, $SO_3M$, where M is a metal cation;

$R^m$ and $R^p$ are each independently selected from optionally substituted $C_1$-$C_8$ alkyl, $C_2$-$C_8$ alkenyl, $C_2$-$C_8$ alkynyl, $C_3$-$C_8$ cycloalkyl, $C_3$-$C_8$ heterocyclyl $C_5$-$C_{20}$ aryl and $C_{5-20}$ heteroaryl groups, and optionally in relation to the group N $R^m$ $R^p$, $R^m$ and $R^p$ together with the nitrogen atom to which they are attached form an optionally substituted 4-, 5-, 6- or 7-membered heterocyclic ring;

$R^{12}$, $R^{16}$, $R^{19}$, $R^{21}$ and $R^{17}$ are as defined for $R^{22}$, $R^{66}$, $R^{99}$, $R^{11}$ and $R^{77}$ respectively;

R" is a $C_3$-$C_{12}$ alkylene group, which chain may be interrupted by one or more heteroatoms, e.g. O, S, N(H), NMe and/or aromatic rings, e.g. benzene or pyridine, which rings are optionally substituted;

X and X' are independently selected from O, S and N(H); and $R^C$ is a capping group.

This invention also relates to pharmaceutical compositions of antibody-drug conjugates of Formula (I).

This invention also relates to a method of treating cancer, use of antibody-drug conjugates of Formula (I) in therapy, and use of antibody-drug conjugates of Formula (I) in manufacturing a medicament for treating cancer.

This invention also relates to method of preparing antibody-drug conjugates of Formula (I).

BRIEF DESCRIPTION OF THE FIGURES

FIG. 1 shows efficacy comparison of NaPi3b ADCs (NaPi3b PBD ADC1-1 and ADC2-1) in SCID-beige mice with OVCAR3X2.1 human ovarian tumors.

FIG. 2 shows efficacy comparison of NaPi3b ADCs (NaPi3b PBD ADC1-1 and $ADC_3$-1) in SCID-beige mice with OVCAR3X2.1 human ovarian tumors.

FIG. 3 shows efficacy of CD33 PBD ADC2-2 at various doses in SCID mice with EOL-1 human acute myeloid leukemia tumors.

DETAILED DESCRIPTION OF THE INVENTION

Provided herein are different types of non-peptide linkers for ADC that are cleavable by lysosomal enzymes. For example, the amide bond in the middle of a dipeptide (e.g. Val-Cit) was replaced with an amide mimic; and/or entire amino acid (e.g., valine amino acid in Val-Cit dipeptide) was replaced with a non-amino acid moiety (e.g., cycloalkyl dicarbonyl structures (for example, ring size=4 or 5)).

This invention relates to antibody-conjugates of Formula (I).

This invention also relates to antibody-conjugates of Formula (I), wherein Y is heteroaryl; $R^4$ and $R^5$ together form a cyclobutyl ring.

This invention also relates to antibody-conjugates of Formula (I), wherein Y is a moiety selected from the group consisting of

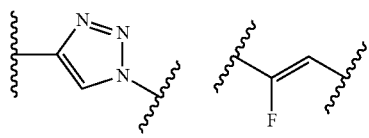

AND

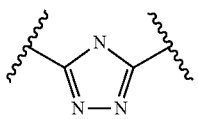

This invention also relates to antibody-conjugates of Formula (I), wherein Str is a chemical moiety represented by the following formula:

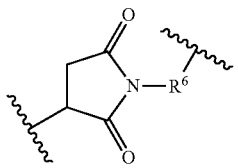

(Ab)

wherein $R^6$ is selected from the group consisting of $C_1$-$C_{10}$alkylene, $C_1$-$C_{10}$alkenyl, $C_3$-$C_8$cycloalkyl, ($C_1$-$C_6$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl, heteroarylalkyl and heteroaryl each $R^a$ is independently H or $C_1$-$C_6$alkyl; Sp is —Ar—$R^b$—, wherein Ar is aryl or heteroaryl, $R^b$ is ($C_1$-$C_{10}$alkylene)-C(=O)O—.

This invention also relates to antibody-conjugates of Formula (I), wherein Str has the formula:

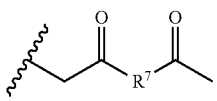

(Ab)

wherein $R^7$ is selected from $C_1$-$C_{10}$alkylene, $C_1$-$C_{10}$alkenyl, ($C_1$-$C_{10}$alkylene)O—, N($R^c$)—($C_1$-$C_6$ alkylene)-N($R^c$) and N($R^c$)—($C_2$-$C_6$alkylene); where each $R^c$ is independently H or $C_1$-$C_6$ alkyl; Sp is —Ar—$R^b$—, wherein Ar is aryl or heteroaryl, $R^b$ is ($C_1$-$C_{10}$alkylene)-C(=O)O—.

This invention also relates to antibody-conjugates of Formula (I), which is represented by:

Ab-(L-D)$_p$ wherein Ab is an antibody; L is non-peptide chemical moiety represented by the following formula

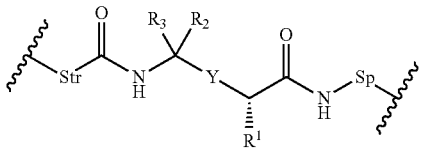

$R^1$ is $C_1$-$C_6$alkyl, $C_1$-$C_6$alkenyl, ($C_1$-$C_6$alkyl)NHC(NH)$NH_2$ or ($C_1$-$C_6$alkyl)NHC(O)$NH_2$;

$R^3$ and $R^2$ are each independently H, $C_1$-$C_{10}$alkyl.

This invention also relates to antibody-conjugates of Formula (I), which is represented by:

Ab-(L-D)$_p$ wherein Ab is an antibody;
L is non-peptide chemical moiety represented by the following formula

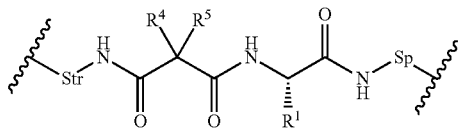

$R^1$ is $C_1$-$C_6$alkyl, ($C_1$-$C_6$alkyl)NHC(NH)NH$_2$ or ($C_1$-$C_6$alkyl)NHC(O)NH$_2$;
$R^4$ and $R^5$ together form a $C_3$-$C_7$cycloalkyl ring.

This invention also relates to antibody-conjugates of Formula (I), which is represented by:

Ab-(L-D)$_p$ wherein Ab is an antibody;
L is non-peptide chemical moiety represented by the following formula

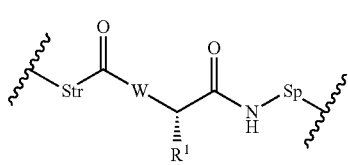

$R^1$ is $C_1$-$C_6$alkyl, ($C_1$-$C_6$alkyl)NHC(NH)NH$_2$ or ($C_1$-$C_6$alkyl)NHC(O)NH$_2$.

This invention also relates to antibody-conjugates of Formula (I) represented by the following formula:

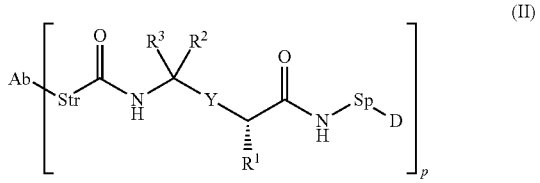

(II)

wherein
Str is a chemical moiety represented by the following formula:

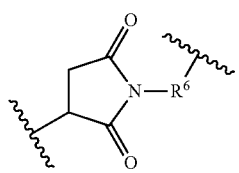

(Ab)

wherein $R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl, heteroarylalkyl and heteroaryl each $R^a$ is independently H or $C_1$-$C_6$alkyl;
p is 1, 2, 3 or 4.

This invention also relates to antibody-conjugates of Formula (I) represented by the following formula:

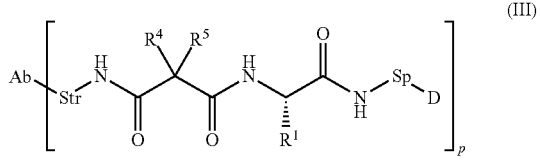

(III)

wherein
Str is a chemical moiety represented by the following formula:

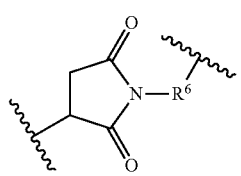

(Ab)

wherein $R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl, heteroarylalkyl and heteroaryl each $R^a$ is independently H or $C_1$-$C_6$alkyl;
p is 1, 2, 3 or 4.

This invention also relates to any one of the above antibody-conjuagates, wherein Y is heteroaryl, aryl or alkenyl; $R^6$ is $C_1$-$C_{10}$alkylene.

This invention also relates to any one of the above antibody-conjuagates, wherein Y is

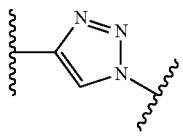 [SMILES: *c1cn(*)nn1]

This invention also relates to any one of the above antibody-conjuagates, wherein Y is

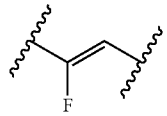

This invention also relates to any one of the above antibody-conjuagates, wherein Y is

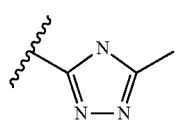 [SMILES: *c1nnc(C)[nH]1]

This invention also relates to any one of the above antibody-conjuagates, wherein Str is a chemical moiety represented by the following formula:

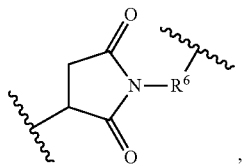

(Ab)

$R^6$ is $C_1$-$C_6$alkylene;

Sp is —Ar—$R^b$—, where Ar is aryl, $R^b$ is ($C_1$-$C_3$alkylene)-C(=O)O—.

This invention also relates to any one of the above antibody-conjuagates represented by the following formula:

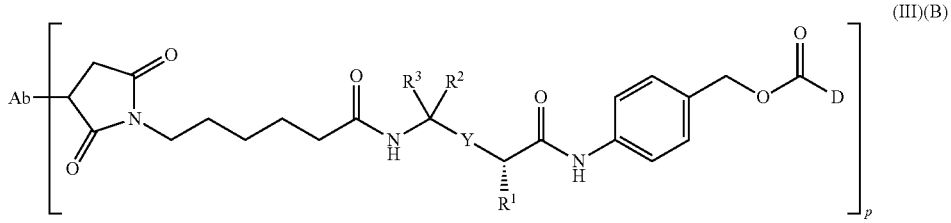

(III)(B)

wherein
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$
p is 1, 2, 3 or 4.

This invention also relates to any one of the above antibody-conjuagates represented by the following formula:

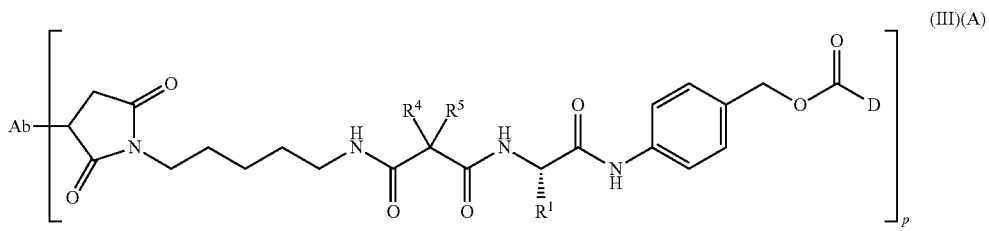

(III)(A)

wherein p is 1, 2, 3 or 4;

$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;

$R^4$ and $R^5$ are each independently $C_1$-$C_6$alkyl, wherein said alkyl are unsubstituted, or $R^4$ and $R^5$ may form a $C_3$-$C_7$cycloalkyl ring.

This invention also relates to non-peptide compounds of Formula (IV):

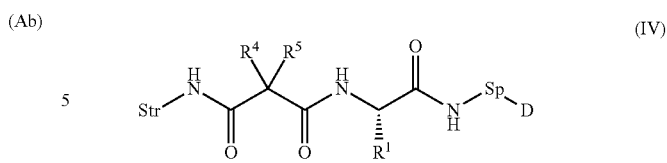

(IV)

wherein

Str is a stretcher unit which can be covalently attached to an antibody;

Sp is a bond or a spacer unit covalently attached to a drug moiety;

$R^1$ is $C_1$-$C_{10}$alkyl, ($C_1$-$C_{10}$alkyl)NHC(NH)$NH_2$ or ($C_1$-$C_{10}$alkyl)NHC(O)$NH_2$;

$R^4$ and $R^5$ are each independently $C_1$-$C_{10}$alkyl, arylalkyl, heteroarylalkyl, ($C_1$-$C_{10}$alkyl)OCH$_2$—, or $R^4$ and $R^5$ may form a $C_3$-$C_7$cycloalkyl ring;

D is a drug moiety of formula A or of formula B:

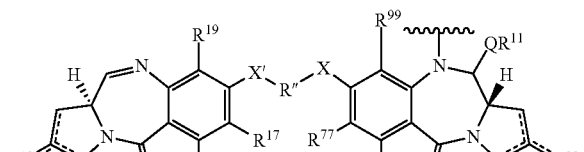

A

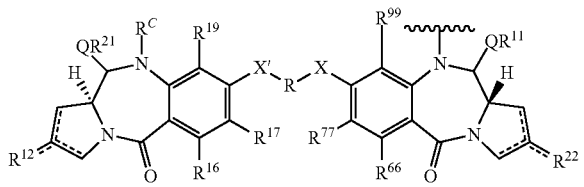

B and salts and solvates thereof, wherein:
the wavy line indicates the covalent attachment site to the linker;
the dotted lines indicate the optional presence of a double bond between C1 and C2 or C2 and C3;
$R^{22}$ is independently selected from H, OH, =O, =CH$_2$, CN, $R^m$, O $R^m$, =CH—$R^D$, =C($R^D$)$_2$, O—SO$_2$—$R^m$, CO$_2$ $R^m$ and CO $R^m$, and optionally further selected from halo or dihalo, wherein $R^D$ is independently selected from $R^m$, CO$_2$ $R^m$, CO $R^m$, CHO, CO$_2$H, and halo;
$R^{66}$ and $R^{99}$ are independently selected from H, $R^m$, OH, O $R^m$, SH, S $R^m$, NH$_2$, NH $R^m$, N $R^m$ $R^p$, NO$_2$, Me$_3$Sn and halo;
$R^{77}$ is independently selected from H, $R^m$, OH, O $R^m$, SH, S $R^m$, NH$_2$, NH $R^m$, N $R^m$ $R^p$, NO$_2$, Me$_3$Sn and halo;
Q is independently selected from O, S and NH;
$R^{11}$ is either H, or $R^m$ or, where Q is O, SO$_3$M, where M is a metal cation;
$R^m$ and $R^p$ are each independently selected from optionally substituted C$_{1-8}$ alkyl, C$_2$-C$_8$ alkenyl, C$_2$-C$_8$ alkynyl, C$_3$-C$_8$ cycloalkyl, C$_{3-8}$ heterocyclyl C$_{5-20}$ aryl and C$_{5-20}$ heteroaryl groups, and optionally in relation to the group N $R^m$ $R^p$, $R^m$ and $R^p$ together with the nitrogen atom to which they are attached form an optionally substituted 4-, 5-, 6- or 7-membered heterocyclic ring;
$R^{12}$, $R^{16}$, $R^{19}$, $R^{21}$ and $R^{17}$ are as defined for $R^{22}$, $R^{66}$, $R^{99}$, $R^{11}$ and $R^{77}$ respectively;
R" is a C$_3$-C$_{12}$ alkylene group, which chain may be interrupted by one or more heteroatoms. e.g. O, S, N(H), NMe and/or aromatic rings, e.g. benzene or pyridine, which rings are optionally substituted;
X and X' are independently selected from O, S and N(H); and $R^C$ is a capping group.

This invention also relates to non-peptide compounds represented by the following formula (IV)(A)

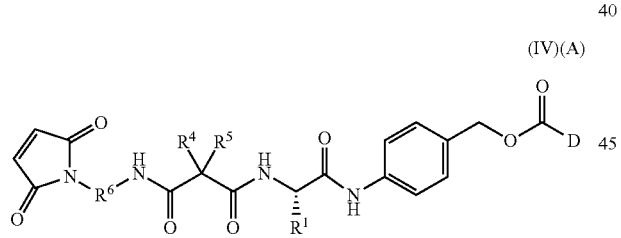

wherein R$_6$ is C$_1$-C$_{10}$alkylene; R$^4$ and R$^5$ together form a C$_3$-C$_7$cycloalkyl ring.

This invention also relates to non-peptide compounds represented by the following formula This invention also relates to non-peptide compounds of Formula:

(V)

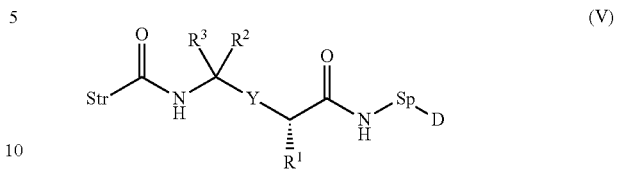

wherein
Str is a stretcher unit which can be covalently attached to an antibody;
Sp is an optional spacer unit covalently attached to a drug moiety;
Y is heteroaryl, aryl, —C(O)C$_1$-C$_6$alkenyl, C$_1$-C$_6$alkenyl or —C$_1$-C$_6$alkenyl-NH—;
R$^1$ is C$_1$-C$_{10}$alkyl, (C$_1$-C$_{10}$alkyl)NHC(NH)NH$_2$ or (C$_1$-C$_{10}$alkyl)NHC(O)NH$_2$;
R$^3$ and R$^2$ are each independently H, C$_1$-C$_{10}$alkyl, arylalkyl or heteroarylalkyl, or R$^3$ and R$^2$ together may form a C$_3$-C$_7$cycloalkyl;
D is a drug moiety of formula A or of formula B:

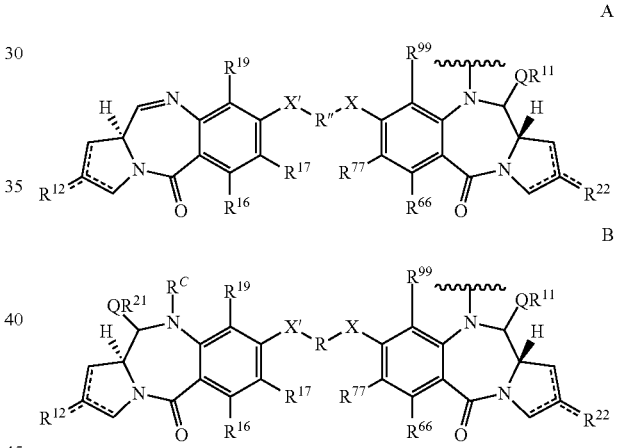

and salts and solvates thereof, wherein:
the wavy line indicates the covalent attachment site to the linker;
the dotted lines indicate the optional presence of a double bond between C1 and C2 or C2 and C3;
$R^{22}$ is independently selected from H, OH, =O, =CH$_2$, CN, $R^m$, O $R^m$, =CH—$R^D$, =C($R^D$)$_2$, O—SO$_2$—$R^m$, CO; $R^m$ and CO $R^m$, and optionally further selected from halo or dihalo, wherein $R^D$ is independently selected from $R^m$, CO$_2$ $R^m$, CO $R^m$, CHO, CO$_2$H, and halo;

(IV)(B)

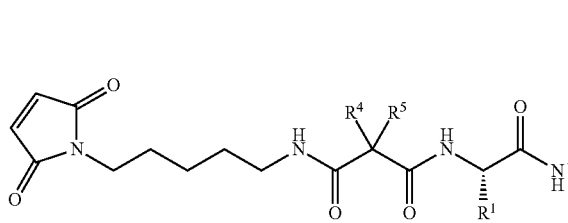

$R^{66}$ and $R^{99}$ are independently selected from H, $R^m$, OH, O $R^m$, SH, S $R^m$, $NH_2$, NH $R^m$, N $R^m$ $R^p$, $NO_2$, $Me_3Sn$ and halo;

$R^{77}$ is independently selected from H, $R^m$, OH, O $R^m$, SH, S $R^m$, $NH_2$, NH $R^m$, N $R^m$ $R^p$, $NO_2$, $Me_3Sn$ and halo;

Q is independently selected from O, S and NH;

$R^{11}$ is either H, or $R^m$ or, where Q is O, $SO_3M$, where M is a metal cation;

$R^m$ and $R^p$ are each independently selected from optionally substituted $C_{1-8}$ alkyl, $C_2$-$C_8$ alkenyl, $C_2$-$C_8$ alkynyl, $C_3$-$C_8$ cycloalkyl, $C_{3-8}$ heterocyclyl $C_{5-20}$ aryl and $C_{5-20}$ heteroaryl groups, and optionally in relation to the group N $R^m$ $R^p$, $R^m$ and $R^p$ together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^{22}$, $R^{66}$, $R^{99}$ and $R^{77}$ respectively;

R" is a $C_3$-$C_{12}$ alkylene group, which chain may be interrupted by one or more heteroatoms. e.g. O, S, N(H), NMe and/or aromatic rings, e.g. benzene or pyridine, which rings are optionally substituted;

X and X' are independently selected from O, S and N(H); and $R^C$ is a capping group.

This invention also relates to non-peptide compounds represented by the following formula:

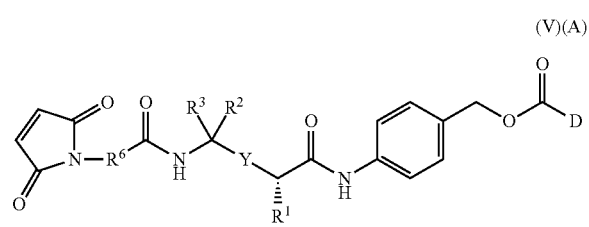

(V)(A)

wherein
$R_6$ is $C_1$-$C_{10}$alkylene.

This invention also relates to non-peptide compounds represented by the following formula:

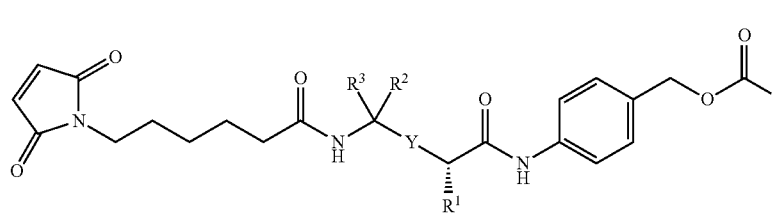

(V)(B)

This invention also relates to any of the above non-peptide compounds, wherein Str has the following formula:

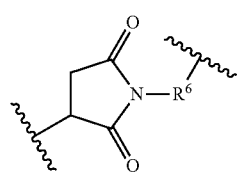

(Ab)

wherein $R^6$ is selected from the group consisting of $C_1$-$C_{10}$alkylene, $C_3$-$C_8$cycloalkyl, O—($C_1$-$C_8$alkylene), and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl and heteroaryl each $R^a$ is independently H or $C_1$-$C_6$alkyl; Sp is —Ar—$R^b$—, wherein Ar is aryl or heteroaryl, $R^b$ is ($C_1$-$C_{10}$alkylene)-C(=O)—O—.

This invention also relates to non-peptide compounds, wherein $R^6$ is $C_1$-$C_{10}$alkylene, Sp is —Ar—$R^b$—, wherein Ar is aryl $R^h$ is ($C_1$-$C_6$alkylene)-C(=O)—O—.

This invention also relates to non-peptide compounds, where $R_6$ is —$(CH_2)_q$ is 1-10;

This invention also relates to non-peptide compounds, wherein Str has the formula:

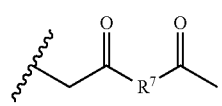

(Ab)

wherein $R^7$ is selected from $C_1$-$C_{10}$alkylene, $C_1$-$C_{10}$alkylene-O, N($R^c$)—($C_2$-$C_6$ alkylene)-N($R^c$) and N($R^c$)—($C_2$-$C_6$alkylene); where each $R^c$ is independently H or $C_1$-$C_6$ alkyl;

Sp is —Ar—$R^b$—, wherein Ar is aryl or heteroaryl, $R^b$ is ($C_1$-$C_{10}$alkylene)-C(=O)—O—.

This invention also relates to non-peptide compounds, wherein $R^6$ is $C_1$-$C_{10}$ alkylene, Sp is —Ar—$R^b$—, wherein Ar is aryl $R^b$ is ($C_1$-$C_6$ alkylene)-C(=O)—O—.

PM

As described above, PM is s a non-peptide chemical moiety selected from the group consisting of:

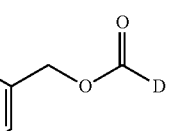

(V)(B)

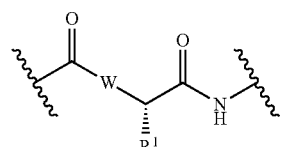

(PM1)

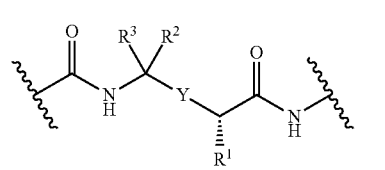

(PM2)

and

-continued

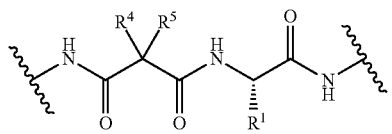
(PM3)

In each of PM1, PM2 and PM3, $R^1$ is independently $C_1$-$C_{10}$alkyl, $C_1$-$C_{10}$alkenyl, ($C_1$-$C_{10}$alkyl)NHC(NH)NH$_2$ or ($C_1$-$C_{10}$alkyl)NHC(O)NH$_2$. In some embodiments, $R^1$ is $C_1$-$C_6$alkyl, ($C_1$-$C_6$alkyl)NHC(NH)NH$_2$ or ($C_1$-$C_6$alkyl)NHC(O)NH$_2$. In some embodiments, $R^1$ is $C_3H_6$NHC(O)NH$_2$ In PM1, W is —NH-heterocycloalkyl- or heterocycloalkyl. In some embodiments, . . .

In PM2, Y is heteroaryl, aryl, —C(O)$C_1$-$C_6$alkylene, $C_1$-$C_6$alkenyl, $C_1$-$C_6$alkylenyl or —$C_1$-$C_6$alkylene-NH—. In some embodiments, Y is heteroaryl. In some of these embodiments, Y is

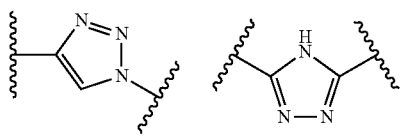 [SMILES: *c1cn(*)nn1 ; *c1nnc(*)[nH]1]

In other embodiments, Y is $C_1$-$C_6$alkylenyl. In some of these embodiments, Y is

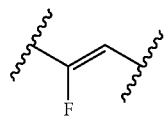 [SMILES: */C=C(/*)F]

In PM2, $R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl (with the carbon atom to which they are attached). In some embodiments, $R^2$ and $R^3$ are each independently H or $C_{1-10}$alkyl. In one such embodiment, $R^2$ is H and $R^3$ is iso-propyl.

In PM3, $R^4$ and R are each independently $C_1$-$C_{10}$alkyl, $C_1$-$C_{10}$alkenyl, arylalkyl, heteroarylalkyl, ($C_1$-$C_{10}$alkyl)OCH$_2$—, or $R^4$ and $R^5$ may form a $C_3$-$C_7$cycloalkyl ring (with the carbon atom to which they are attached). In some of these embodiments, $R^4$ and $R^5$ together form a $C_3$-$C_7$cycloalkyl ring (with the carbon atom to which they are attached). In particular, they may form a cyclobutyl group, such that PM3 is:

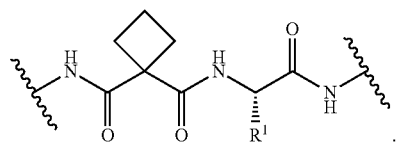

In some embodiments, the PM group may be:

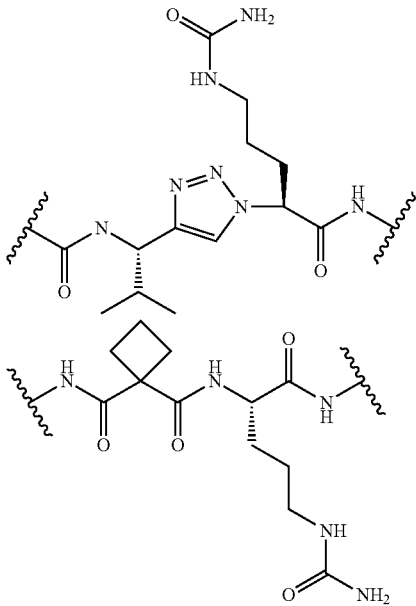

Str

As described above, Str is a stretcher unit covalently attached to Ab.

In some embodiments, Str is a chemical moiety represented by the following formula:

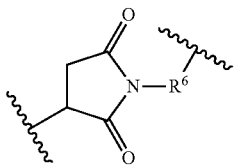
(Str1)

wherein $R^6$ is selected from the group consisting of $C_1$-$C_{10}$alkylene, $C_1$-$C_{10}$alkenyl, $C_3$-$C_8$cycloalkyl, ($C_1$-$C_6$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl, heteroarylalkyl and heteroaryl each $R^a$ is independently H or $C_1$-$C_6$alkyl; Sp is —Ar—$R^b$—, wherein Ar is aryl or heteroaryl, $R^b$ is ($C_1$-$C_{10}$alkylene)O—.

In some of these embodiments. $R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl, heteroarylalkyl and heteroaryl each $R^a$ is independently H or $C_1$-$C_6$alkyl.

In some of these embodiments, $R^6$ is $C_1$-$C_{10}$alkylene, $C_{1-6}$alkylene. In particular embodiments, $R^6$ is $C_5$ alkylene.

In some embodiments Str has the formula:

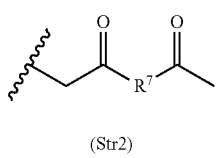

(Ab)

(Str2)

wherein $R^7$ is selected from $C_1$-$C_{10}$alkylene, $C_1$-$C_{10}$alkenyl, ($C_1$-$C_{10}$alkylene)O—, $N(R^c)$—($C_2$-$C_6$ alkylene)-$N(R^c)$ and $N(R^c)$—($C_2$-$C_6$alkylene); where each R is independently H or $C_1$-$C_6$ alkyl. In some of these embodiments, $R^7$ is selected from $C_1$-$C_{10}$alkylene, $C_1$-$C_{10}$alkenyl, ($C_1$-$C_{10}$alkylene)O—, $N(R^c)$—($C_2$-$C_6$ alkylene)-$N(R^c)$ and $N(R^c)$—($C_2$-$C_6$alkylene); where each $R^1$ is independently H or $C_1$-$C_6$ alkyl.

Sp

Sp is a bond or a spacer unit covalently attached to the drug moiety.

In some embodiments, Sp is —Ar—$R^b$—, wherein Ar is aryl or heteroaryl, $R^b$ is ($C_1$-$C_{10}$alkylene)OC(=O)—. In some of these embodiments, $R^b$ is ($C_1$-$C_3$alkylene)OC(=O)—. In further of these embodiments, $R^b$ is —$CH_2$—OC(=O)—. In some embodiments, Ar is phenylene and it may be:

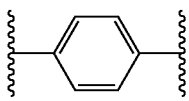

Thus Sp may be:

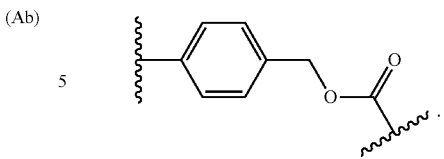

Str, PM, Sp

In some embodiments, -Str-PM-Sp- is selected from:

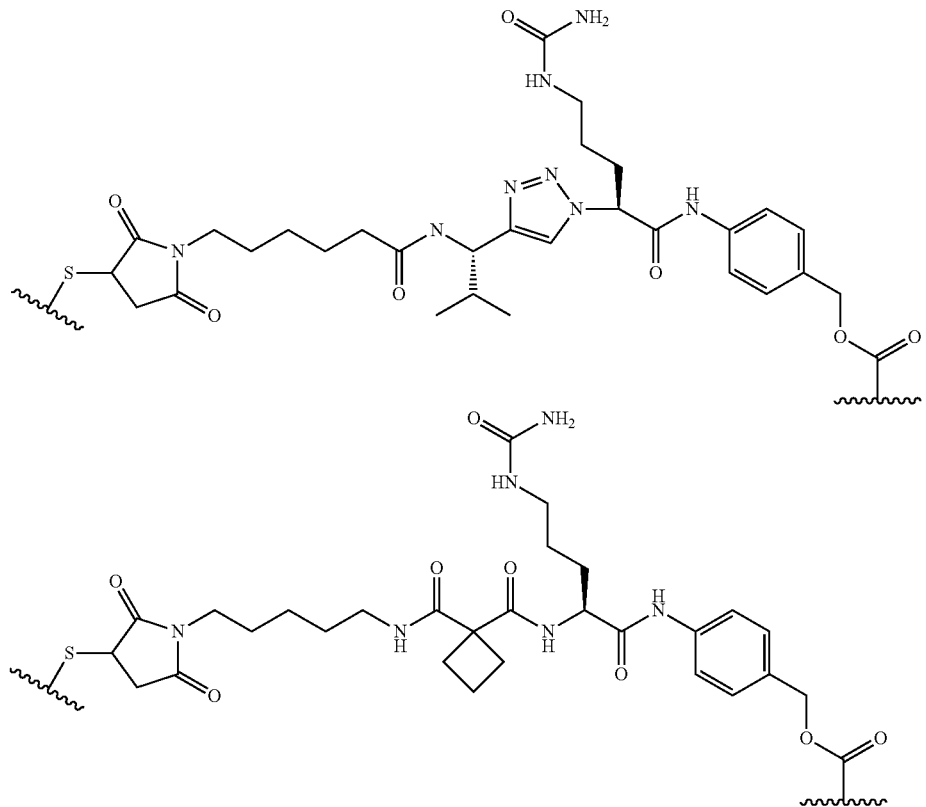

$R^C$

The group $R^C$ is removable from the N10 position of the PBD moiety to leave an N10-C11 imine bond, a carbinolamine, a substituted carbinolamine, where $QR^{11}$ is $OSO_3M$, a bisulfite adduct, a thiocarbinolamine, a substituted thiocarbinolamine, or a substituted carbinalamine.

In one embodiment, $R^C$, may be a protecting group that is removable to leave an N10-C11 imine bond, a carbinolamine, a substituted cabinolamine, or, where $QR^{21}$ is $OSO_3M$, a bisulfite adduct. In one embodiment, $R^C$ is a protecting group that is removable to leave an N10-C11 imine bond.

The group R is intended to be removable under the same conditions as those required for the cleaving of the peptidomimetic linker, for example to yield an N10-C11 imine bond, a carbinolamine and so on. The capping group acts as a protecting group for the intended functionality at the N10 position. The capping group is not reactive towards the antibody, thus, for example, $R^C$ is not Str-(PM)-Sp-.

The capping group may be referred to as a therapeutically removable nitrogen protecting group, as defined in WO 00/12507, which definition is herein incorporated by reference.

In one embodiment, the group $R^C$ is removable under the conditions that cleave the peptidomimetic group, PM. Thus, in one embodiment, the capping group is cleavable by the action of an enzyme.

The capping group may be used as a mask for a N10-C11 imine bond. The capping group may be removed at such time as the imine functionality is required in the compound. The capping group is also a mask for a carbinolamine, a substituted cabinolamine, and a bisulfite adduct, as described above.

In one embodiment, $R^C$ is a carbamate protecting group.

In one embodiment, the carbamate protecting group is selected from:

Alloc, Fmoc, Boc, Troc and Teoc.

In one embodiment, $R^C$ is derived from a linker group Str-(PM)-Sp- lacking the functional group for connection to the antibody.

This application is particularly concerned with those $R^C$ groups which are carbamates.

In one embodiment, $R^C$ is a group:

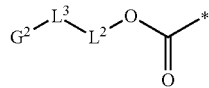

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker. Alternatively, $L^3$ can be PM and $L^2$ together with OC(=O) form Sp.

Where $L^3$ and $L^2$ are both covalent bonds, $G^2$ and OC(=O) together form a carbamate protecting group as defined above.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of $R^{10}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker. In one embodiment, $L^2$ is a substrate for enzymatic activity, thereby allowing release of $R^{10}$ from the N10 position.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from:

—C(=O)NH—,
—C(=O)O—,
—NHC(=O)—,
—OC(=O)—,
—OC(=O)O—,
—NHC(=O)O—,
—OC(O)NH—, and
—NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to L may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids: and (iv) all enantiomers, diastereomers, isomerically enriched, isotopically labelled (e.g. H, $^3$H, $^{14}$C, $^{15}$N), protected forms, and racemic mixtures thereof.

In one embodiment, —C(=O)O— and $L^2$ together form the group:

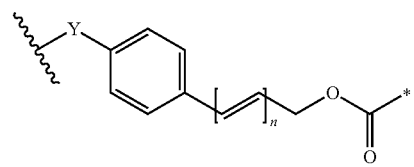

where the asterisk indicates the point of attachment to the N10 position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

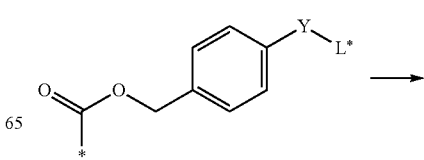

-continued

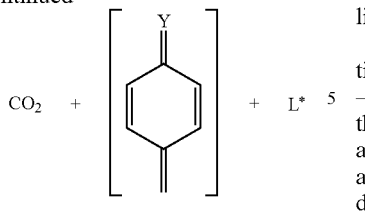

where L* is the activated form of the remaining portion of the linker. These groups have the advantage of separating the site of activation from the compound being protected. As described above, the phenylene group may be optionally substituted.

In one embodiment described herein, the group L* is a linker $L^1$ as described herein, which may include a dipeptide group.

In another embodiment, —C(=O)O— and $L^2$ together form a group selected from:

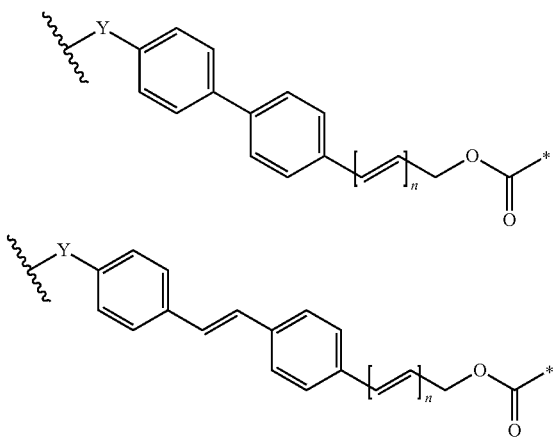

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and $L^2$ together form a group selected from:

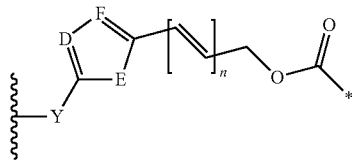

where the asterisk, the wavy line, Y, and n are as defined above, E is O, S or NR, D is N, CH, or CR, and F is N, CH, or CR.
In one embodiment, D is N.
In one embodiment, D is CH.
In one embodiment, E is O or S.
In one embodiment, F is CH.

In a preferred embodiment, the linker is a cathepsin labile linker.

In one embodiment, $L^1$ comprises a dipeptide The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
 -Phe-Lys-,
 -Val-Ala-,
 -Val-Lys-,
 -Ala-Lys-,
 -Val-Cit-,
 -Phe-Cit-,
 -Leu-Cit-,
 -Ile-Cit-,
 -Phe-Arg-,
 -Trp-Cit-
where Cit is citrulline.

Preferably, the group —$X_1$—$X_2$— in dipeptide, —NH—$X_1$—$X_2$—CO—, is selected from:
 -Phe-Lys-,
 -Val-Ala-,
 -Val-Lys-,
 -Ala-Lys-,
 -Val-Cit-.

Most preferably, the group —$X_1$—$X_2$— in dipeptide, —NH—$X_1$—$X_2$—CO—, is -Phe-Lys- or -Val-Ala-.

Other dipeptide combinations may be used, including those described by Dubowchik et al., *Bioconjugate Chemistry*, 2002, 13,855-869, which is incorporated herein by reference.

In one embodiment, the amino acid side chain is derivatised, where appropriate. For example, an amino group or carboxy group of an amino acid side chain may be derivatised.

In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate. The side chain protecting group may be a group as discussed below in relation to the group $R^L$. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
 Arg: Z, Mtr, Tos;
 Asn: Trt, Xan;

Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos. Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the invention, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC(=O)— comprise the group NH—$X_1$—$X_2$—CO-PABC-. The PABC group is connected directly to the N10 position. Preferably, the self-immolative linker and the dipeptide together form the group —NH-Phe-Lys-CO—NH-PABC-, which is illustrated below:

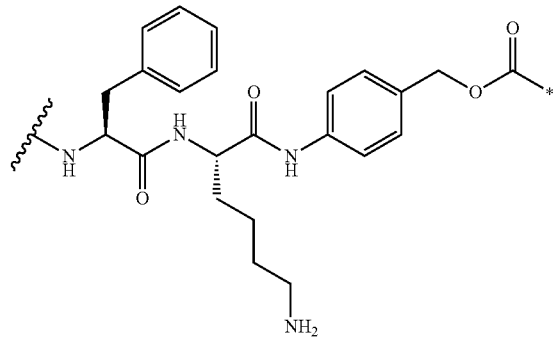 [SMILES: *N[C@@H](Cc1ccccc1)C(=O)N[C@@H](CCCCN)C(=O)Nc1ccc(COC(*)=O)cc1]

where the asterisk indicates the point of attachment to the N10 position, and the wavy line indicates the point of attachment to the remaining portion of the linker $L^1$ or the point of attachment to A. Preferably, the wavy line indicates the point of attachment to A. The side chain of the Lys amino acid may be protected, for example, with Boc, Fmoc, or Alloc, as described above.

Alternatively, the self-immolative linker and the dipeptide together form the group —NH-Val-Ala-CO—NH-PABC-, which is illustrated below:

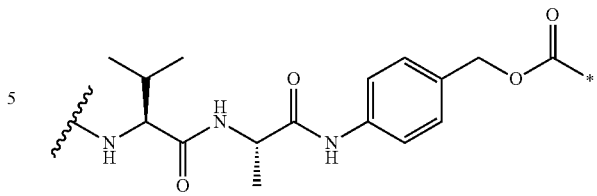

where the asterisk and the wavy line are as defined above.
Alternatively, the self-immolative linker and the dipeptide together form the group —NH-Val-Cit-CO—NH-PABC-, which is illustrated below:

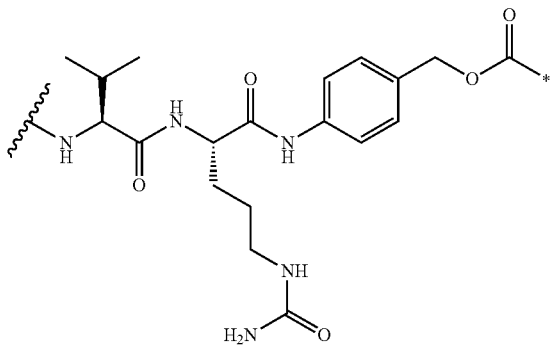 [SMILES: *N[C@H](C(=O)N[C@@H](CCCNC(N)=O)C(=O)Nc1ccc(COC(*)=O)cc1)C(C)C]

where the asterisk and the wavy line are as defined above.
Various terminating groups are described below, including those based on well known protecting groups.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from:

Alloc, Fmoc, Boc, Troc, Teoc, Psec, Cbz and PNZ.

Optionally, the carbamate protecting group is further selected from Moc.

In another embodiment, $G^2$ is an acyl group —C(=O)$G^3$, where $G^3$ is selected from alkyl (including cycloalkyl, alkenyl and alkynyl), heteroalkyl, heterocyclyl and aryl (including heteroaryl and carboaryl). These groups may be optionally substituted. The acyl group together with an amino group of $L^3$ or $L^2$, where appropriate, may form an amide bond. The acyl group together with a hydroxy group of $L^3$ or $L^2$, where appropriate, may form an ester bond.

In one embodiment, $G^3$ is heteroalkyl. The heteroalkyl group may comprise polyethylene glycol. The heteroalkyl group may have a heteroatom, such as O or N, adjacent to the acyl group, thereby forming a carbamate or carbonate group, where appropriate, with a heteroatom present in the group $L^3$ or $L^2$, where appropriate.

In one embodiment, $G^3$ is selected from $NH_2$, NHR and NRR'. Preferably, $G^3$ is NRR'.

In one embodiment $G^2$ is the group:

where the asterisk indicates the point of attachment to $L^1$, n is 0 to 6 and $G^4$ is selected from OH, OR, SH, SR, COOR, $CONH_2$, CONHR, CONRR', $NH_2$, NHR, NRR', $NO_2$, and halo. The groups OH, SH, $NH_2$ and NHR are protected. In one embodiment, n is 1 to 6, and preferably n is 5. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Most preferably $G^4$ is OMe.

In one embodiment, the group $G^2$ is:

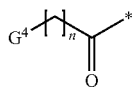

where the asterisk indicates the point of attachment to $L^1$, and n and $G^4$ are as defined above.

In one embodiment, the group $G^2$ is:

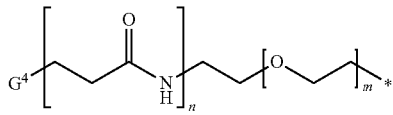

where the asterisk indicates the point of attachment to $L^3$, n is 0 or 1, m is 0 to 50, and $G^4$ is selected from OH, OR, SH, SR, COOR, $CONH_2$, CONHR, CONRR', $NH_2$, NHR, NRR', $NO_2$, and halo. In a preferred embodiment, n is 1 and m is 0 to 10, 1 to 2, preferably 4 to 8, and most preferably 4 or 8. In another embodiment, n is 1 and m is 10 to 50, preferably 20 to 40. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

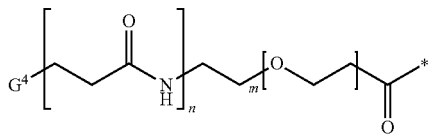

where the asterisk indicates the point of attachment to $L^3$, and n, m and $G^4$ are as defined above.

In one embodiment, the group $G^2$ is:

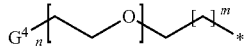

where n is 1-20, m is 0-6, and $G^4$ is selected from OH, OR, SH, SR, COOR, $CONH_2$, CONHR. CONRR', $NH_2$, NHR, NRR'. $NO_2$, and halo. In one embodiment, n is 1-10. In another embodiment, n is 10 to 50, preferably 20 to 40. In one embodiment, n is 1. In one embodiment, m is 1. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

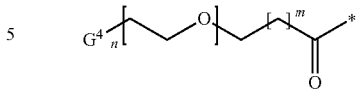

where the asterisk indicates the point of attachment to $L^3$, and n, m and $G^4$ are as defined above.

In each of the embodiments above $G^4$ may be OH, SH, $NH_2$ and NHR. These groups are preferably protected.

In one embodiment, OH is protected with Bzl, TBDMS, or TBDPS.

In one embodiment, SH is protected with Acm, Bzl, Bzl-OMe, Bzl-Me, or Trt.

In one embodiment, $NH_2$ or NHR are protected with Boc, Moc, Z—Cl Fmoc, Z, or Alloc.

In one embodiment, the group $G^2$ is present in combination with a group $L^3$, which group is a dipeptide.

The capping group is not intended for connection to the cell binding agent. Thus, the other monomer present in the dimer serves as the point of connection to the cell binding agent via a linker. Accordingly, it is preferred that the functionality present in the capping group is not available for reaction with a cell binding agent. Thus, reactive functional groups such as OH, SH, $NH_2$, COOH are preferably avoided. However, such functionality may be present in the capping group if protected, as described above.

In some embodiments of the invention, D is a drug moiety of formula A

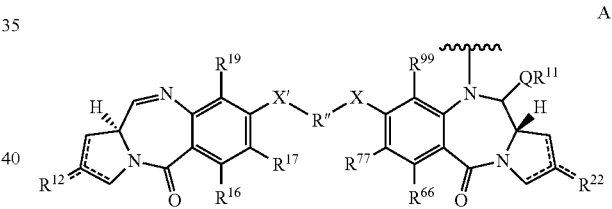

A and salts and solvates thereof, wherein:
the wavy line indicates the covalent attachment site to the linker;
the dotted lines indicate the optional presence of a double bond between C1 and C2 or C2 and C3;
$R^{22}$ is independently selected from H, OH, =O, $=CH_2$, CN, $R^m$, O $R^m$, $=CH-R^D$, $=C(R^D)_2$, $O-SO_2-R^m$, $CO_2 R^m$ and CO $R^m$, and optionally further selected from halo or dihalo, wherein $R^D$ is independently selected from $R^m$, $CO_2 R^m$, CO $R^m$, CHO, $CO_2H$, and halo;
$R^{66}$ and $R^{99}$ are independently selected from H, $R^m$, OH, O $R^m$, SH, S $R^m$, $NH_2$, NH $R^m$, N $R^m$ $R^p$, $NO_2$, $Me_3Sn$ and halo;
$R^{77}$ is independently selected from H, $R^m$, OH, O $R^m$, SH, S $R^m$, $NH_2$, NH $R^m$, N $R^m$ $R^p$, $NO_2$, $Me_3Sn$ and halo;
Q is independently selected from O, S and NH;
$R^{11}$ is either H, or $R^m$ or, where Q is O, $SO_3M$, where M is a metal cation;
$R^m$ and $R^p$ are each independently selected from optionally substituted $C_1$-$C_5$ alkyl, $C_3$-$C_8$ heterocyclyl and $C_5$-$C_{20}$ aryl groups, and optionally in relation to the group N $R^m$ $R^p$, $R^m$ and $R^p$ together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^{22}$, $R^{66}$, $R^{99}$ and $R^{77}$ respectively;

R" is a $C_3$-$C_{12}$ alkylene group, which chain may be interrupted by one or more heteroatoms, e.g. O, S, N(H), NMe and/or aromatic rings, e.g. benzene or pyridine, which rings are optionally substituted;

X and X' are independently selected from O, S and N(H).

This invention also relates to any one of the above antibody-drug conjugates, wherein p is 2.

This invention also relates to any one of the above antibody-drug conjugates, wherein the antibody binds to one or more of polypeptides selected from the group consisting of:

BMPR1B;
E16;
STEAP1;
0772P;
MPF;
Napi3b;
Sema 5b;
PSCA hlg;
ETBR;
MSG783;
STEAP2;
TrpM4;
CRIPTO;
CD21;
CD79b;
FcRH2;
HER2;
NCA;
MDP;
IL20Rα;
Brevican;
EphB2R;
ASLG659;
PSCA;
GEDA;
BAFF-R;
CD22;
CD79a;
CXCR5;
HLA-DOB;
P2X5;
CD72;
LY64;
FcRH1;
IRTA2;
TENB2;
PMEL17;
TMEFF1;
GDNF-Ra1;
Ly6E;
TMEM46;
Ly6G6D;
LGR5;
RET;
LY6K;
GPR19;
GPR54;
ASPHD1;
Tyrosinase;
TMEM18;
GPR172A;
MUC16 and
CD33.

This invention also relates to methods of treating a disease in a human in need thereof, comprising administering to said human an effective amount of an Antibody-drug conjugate of claim 1.

This invention also relates to pharmaceutical compositions comprising a compound of claim 1 and a pharmaceutically acceptable carrier thereof.

This invention also relates to any one of the above antibody-drug conjugates, wherein the antibody binds to one or more of polypeptides selected from the group consisting of:

STEAP1;
Napi3b;
STEAP2;
TrpM4;
CRIPTO;
CD21;
CD79b;
FcRH2;
HER2;
CD22;
CD79a;
CD72;
LY64;
Ly6E;
MUC16; and
CD33.

This invention also relates to any one of the above antibody-drug conjugates, wherein the antibody binds to CD33.

This invention also relates to any one of the above antibody-drug conjugates, wherein the antibody binds to CD33 and the anti-CD33 antibody comprise an HVR-L1 comprising the amino acid sequence of SEQ ID NO: 11, an HVR-L2 comprising the amino acid sequence of SEQ ID NO:12, an HVR-L3 comprising the amino acid sequence of SEQ ID NO:13, an HVR-H1 comprising the amino acid sequence of SEQ ID NO: 14, an HVR-H2 comprising the amino acid sequence of SEQ ID NO:15, and an HVR-H3 comprising the amino acid sequence of SEQ ID NO: 16.

This invention also relates to any one of the above antibody-drug conjugates, wherein the antibody binds to CD33 and the anti-CD33 antibody comprises a VL domain comprising the amino acid sequence of SEQ ID NO:17 and a VH domain comprising the amino acid sequence of SEQ ID NO:18.

In some embodiments, the antibody of the antibody-drug conjugate binds CD33. In some embodiments, the antibody of the antibody-drug conjugate comprises (a) HVR-H1 comprising the amino acid sequence of SEQ ID NO:22; (b) HVR-H2 comprising the amino acid sequence of SEQ ID NO:23; (c) HVR-H3 comprising the amino acid sequence of SEQ ID NO:24; (d) HVR-L1 comprising the amino acid sequence of SEQ ID NO:19; (e) HVR-L2 comprising the amino acid sequence of SEQ ID NO:20; and (f) HVR-L3 comprising an amino acid sequence selected from SEQ ID NO:21.

In some embodiments, the antibody comprises a VH as in any of the embodiments provided above, and a VL as in any of the embodiments provided above. In one embodiment, the antibody comprises the VL and VH sequences in SEQ ID NO:25 and SEQ ID NO:26, respectively, including post-translational modifications of those sequences.

This invention also relates to any one of the above antibody-drug conjugates, wherein the antibody binds to NaPi3b.

This invention also relates to any one of the above antibody-drug conjugates, wherein the antibody binds to NaPi3b and the NaPi3b antibody comprise an HVR-L1 comprising the amino acid sequence of SEQ ID NO: 1, an HVR-L2 comprising the amino acid sequence of SEQ ID NO:2, an HVR-L3 comprising the amino acid sequence of SEQ ID NO:3, an HVR-H1 comprising the amino acid sequence of SEQ ID NO:4, an HVR-H2 comprising the amino acid sequence of SEQ ID NO:5, and an HVR-H3 comprising the amino acid sequence of SEQ ID NO: 6.

This invention also relates to any one of the above antibody-drug conjugates, wherein the antibody binds to NaPi3b and the NaPi3b antibody comprise s a VL domain comprising the amino acid sequence of SEQ ID NO:7 and a VH domain comprising the amino acid sequence of SEQ ID NO:8.

This invention also relates to any one of the above antibody-drug conjugates, wherein the antibody binds to NaPi3b and the NaPi3b antibody comprises an amino acid sequence of SEQ ID NO:9 and an amino acid sequence of SEQ ID NO: 10.

Definitions

Unless stated otherwise, the following terms and phrases as used herein are intended to have the following meanings: when trade names are used herein, applicants intend to independently include the trade name product formulation, the generic drug, and the active pharmaceutical ingredient(s) of the trade name product.

The term "peptidomimetic" or PM as used herein means a non-peptide chemical moiety. Peptides are short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A peptidomimetic chemical moiety includes non-amino acid chemical moieties. A peptidomimetic chemical moiety may also include one or more amino acid that are separated by one or more non-amino acid chemical units. A peptidomimetic chemical moiety does not contain in any portion of its chemical structure two or more adjacent amino acids that are linked by peptide bonds.

The term "amino acid" as used herein means glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, glutamine or citrulline.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "antibody fragment(s)" as used herein comprises a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules, and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature, 256:495, or may be made by recombinant DNA methods (see for example: U.S. Pat. Nos. 4,816,567; and 5,807,715). The monoclonal antibodies may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

The term "intact antibody" as used herein is one that comprises a VL and VH domains, as well as a light chain constant domain (CL) and heavy chain constant domains, CH₁, CH₂ and CH₃. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" as used herein means a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

The term "framework" or "FR" as used herein refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4. Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310).

The term "human antibody" as used herein refers to an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "human consensus framework" as used herein refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

The term "humanized antibody" as used herein refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "variable region" or "variable domain" as used herein refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "free cysteine amino acid" as used herein refers to a cysteine amino acid residue which has been engineered into a parent antibody, has a thiol functional group (—SH), and is not paired as an intramolecular or intermolecular disulfide bridge.

The term "Linker", "Linker Unit", or "link" as used herein means a chemical moiety comprising a chain of atoms that covalently attaches a drug moiety to an antibody. In various embodiments, a linker is a divalent radical, specified as L.

The term "drug moiety" as used herein means a substance that that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; and the various antitumor or anticancer agents disclosed below.

As used herein, unless defined otherwise in a claim, the term "acyl" refers to the group —C(O)R', where R' is alkyl, $C_3$-$C_6$cycloalkyl, or heterocyclyl, as each is defined herein.

As used herein, unless defined otherwise in a claim, the term "alkoxy" refers to the group —OR', where R' is $C_1$-$C_4$alkyl or $C_3$-$C_6$cycloalkyl as defined above. Examples of "alkoxy" include methoxy, ethoxy, isopropoxy, propoxy, butoxy, t-butoxy, isobutoxy, cyclopropoxy, and cyclobutoxy, and halogenated forms thereof, e.g. fluoromethoxy and difluoromethoxy.

As used herein, unless defined otherwise in a claim, the term "alkyl" refers to a straight or branched, monovalent or divalent hydrocarbon chain radical having from one to twelve ($C_1$-$C_{12}$) carbon atoms, which may be unsubstituted or substituted with multiple degrees of substitution, for example one, two, three, four, five or six included within the present invention. Examples of substituents are selected from the group consisting of halo, trifluoromethyl, difluoromethyl, amino, alkylamino, cyano, sulfonyl, sulfonamide, sulfoxide, hydroxy, alkoxy, ester, carboxylic acid and alkylthio. Examples of "alkyl" as used herein include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, as well as the divalent ("alkylene") and substituted versions thereof.

Examples of substituted alkyl include but are not limited to, hydroxymethyl, difluoromethyl and trifluoromethyl.

As used herein unless otherwise defined in a claim, the term "alkenyl" means a linear or branched, monovalent or divalent hydrocarbon chain radical of any length from two to eight carbon atoms ($C_2$-$C_{10}$) with at least one site of unsaturation, i.e., a carbon-carbon, sp$^2$ double bond, wherein the alkenyl radical may be optionally substituted independently with one or more substituents described above in the definition of "alkyl", and includes radicals having "cis" and "trans" orientations, or alternatively, "E" and "Z" orientations. Examples of alkenyl include, but are not limited to, ethenyl or vinyl (—CH═CH$_2$), prop-1-enyl (—CH═CHCH$_3$), prop-2-enyl (—CH$_2$CH═CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl as well as the divalent ("alkenylene") and substituted versions thereof.

As used herein unless otherwise defined in a claim, the term "alkynyl" refers to a linear or branched, monovalent or divalent hydrocarbon radical of any length from two to eight carbon atoms ($C_2$-$C_{10}$) with at least one site of unsaturation, i.e., a carbon-carbon, sp triple bond, wherein the alkynyl radical may be optionally substituted independently with one or more substituents described above in the definition of alkyl, examples of alkynyl includes, but not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl, as well as the divalent ("alkynylene") and substituted versions thereof.

As used herein, unless defined otherwise in a claim, the term "alkylamino" refers to the group —NR'R", wherein R' is H, $C_1$-$C_6$alkyl or $C_3$-$C_6$cycloalkyl, and R" is $C_1$-$C_6$alkyl or $C_3$-$C_6$cycloalkyl, examples of alkylamino include, but are not limited to, methylamino, dimethylamino, ethylamino, diethylamino, propylamino and cyclopropylamino.

As used herein, unless defined otherwise in a claim, the term "amide" refers to the group —C(O)NR'R", wherein R' and R" are each independently H, $C_1$-$C_6$alkyl, or $C_3$-$C_6$cycloalkyl; examples of amide include, but are not limited to, —C(O)NH$_2$, —C(O)NHCH$_3$, and —C(O)N(CH$_3$)$_2$.

As used herein, unless defined otherwise in a claim, the term "aryl" refers to an aromatic, hydrocarbon, ring system. The ring system may be monocyclic or fused polycyclic (e.g., bicyclic, tricyclic, etc.), substituted or unsubstituted. In various embodiments, the monocyclic aryl ring is $C_5$-$C_{10}$, or $C_5$-$C_7$, or $C_5$-$C_6$, where these carbon numbers refer to the number of carbon atoms that form the ring system. A $C_6$ ring system, i.e. a phenyl ring, is an aryl group. In various embodiments, the polycyclic ring is a bicyclic aryl group, where examples of bicyclic aryl groups include are $C_8$-$C_{12}$, or $C_9$-$C_{10}$. A naphthyl ring, which has 10 carbon atoms, is a polycyclic aryl group. Examples of substituents for aryl are described below in the definition of "optionally substituted".

As used herein, unless defined otherwise in a claim, the term "cyano" refers to the group —CN.

As used herein, unless defined otherwise in a claim, "cycloalkyl" refers to a non-aromatic, substituted or unsubstituted, saturated or partially unsaturated hydrocarbon ring group. Examples of substituents are described in the definition of "optionally substituted". In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane.

As used herein, unless defined otherwise in a claim, the term "ester" refers to the group —C(O)OR', where R' is $C_1$-$C_6$alkyl, or $C_3$-$C_6$cycloalkyl.

As used herein, unless defined otherwise in a claim, the term "heterocycle" "heterocycloalkyl" or "heterocyclyl" refers to unsubstituted and substituted mono- or polycyclic non-aromatic ring system containing 2 to 12 ring carbon atoms and 1 to 3 ring hetero atoms. Polycyclic ring systems can be fused bi- or tri-cyclic, spiro or bridged. Examples of heteroatoms include N, O, and S, including N-oxides, sulfur oxides, and dioxides. In one embodiment, the ring is three to eight-membered and is either fully saturated or has one or more degrees of unsaturation. Multiple degrees of substitution are included within the present definition. Examples of substituents are defined hereunder. Examples of "heterocyclic" groups include, but are not limited to tetrahydrofuranyl, pyranyl, 1,4-dioxanyl, 1,3-dioxanyl, oxolanyl, oxetanyl, 2-oxa-6-azaspiro[3.3]heptan-6-yl, piperidinyl, pyrrolidinyl, morpholinyl, azetidinyl, piperazinyl, pyrrolidinonyl, piperazinonyl, pyrazolidinyl, imidazolinyl, imidazolidinyl, and their various tautomers.

As used herein, unless defined otherwise in a claim, the term "heteroaryl", unless defined otherwise in a claim, refers to an aromatic ring system containing 1 to 9 carbon(s) and at least one heteroatom. Examples of heteroatoms include N, O, and S. Heteroaryl may be monocyclic or polycyclic, substituted or unsubstituted. A monocyclic heteroaryl group may have 2 to 6 ring carbon atoms and 1 to 3 ring hetero atoms in the ring, while a polycyclic heteroaryl may contain 3 to 9 ring carbon atoms and 1 to 5 ring hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuranyl, benzothiophenyl, furanyl, imidazolyl, indolyl, azaindolyl, azabenzimidazolyl, benzoxazolyl, benzthiazolyl, benzothiadiazolyl, benzotriazolyl, benzoimidazolyl, tetrazinyl, tetrazolyl, isothiazolyl, oxazolyl, isoxazolyl, pyrazinyl, pyrazolyl, pyridazinyl, pyridinyl, pyrimidinyl, pyrrolyl, quinolinyl, quinazolinyl, quinoxalinyl, triazinyl, triazolyl, thiazolyl and thiophenyl. Examples of substituents for heteroaryl are described below in the definition of "optionally substituted".

As used herein, unless defined otherwise in a claim, the term "heteroarylalkyl" means the group (heteroaryl)$C_1$-$C_3$alkyl.

As used herein, unless defined otherwise in a claim, the term "arylalkyl" means the group (aryl)$C_1$-$C_3$alkyl.

As used herein, unless defined otherwise in a claim, the term "urea" refers to the group —NR'C(O)NR", wherein R' and R" are each independently H, $C_1$-$C_6$alkyl, or $C_3$-$C_6$cycloalkyl.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two or three. The phrase should not be interpreted as duplicative of the substitutions herein described and depicted. Exemplary optional substituent groups include acyl, $C_1$-$C_6$alkyl, sulfonyl, amino, sulfonamide, sulfoxide, alkoxy, cyano, halo, urea, ester, carboxylic acid, amide, hydroxy, oxo, and nitro.

Halo: F, Cl, Br, and I.

Hydroxy: OH.

Alkoxy: OR, wherein R is an alkyl group, for example, a $C_{1-8}$ alkyl group. Examples of $C_{1-8}$ alkoxy groups include, but are not limited to, —OMe (methoxy), -OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): =O.

Acyl (keto): —C(=O)R, wherein R is an acyl substituent, for example, a $C_{1-8}$ alkyl group (also referred to as $C_{1-8}$alkylacyl or $C_{1-8}$ alkanoyl), a $C_{2-8}$ alkenyl group (also referred to as $C_{2-8}$alkenylacyl), a $C_{2-8}$ alkynyl group (also referred to $C_{2-8}$ alkynylacyl), a $C_{3-8}$ cycloalkyl group (also referred to as $C_{3-8}$-cycloalkylacyl), a $C_{3-8}$ heterocyclyl group (also referred to as $C_{3-20}$ heterocyclylacyl), a $C_{5-20}$ aryl group (also referred to as $C_{5-20}$ arylacyl), or a $C_{5-20}$ heteroaryl group (also referred to as $C_{5-20}$ heteroarylacyl), preferably a $C_{1-8}$alkyl group. Examples of acyl groups include, but are not limited to, —C(=O)$CH_3$ (acetyl), —C(=O)$CH_2CH_3$ (propionyl), —C(=O)C($CH_3$)$_3$ (t-butyryl), and —C(=O)Ph (benzoyl, phenone).

Carboxy (carboxylic acid): —C(=O)OH.

Ester (carboxylate, carboxylic acid ester, oxycarbonyl): —C(=O)OR, wherein R is an ester substituent, for example, a $C_1$-$C_8$ alkyl, $C_2$-$C_8$ alkenyl, $C_2$-$C_8$ alkynyl, $C_3$-$C_8$ cycloalkyl, $C_3$-$C_8$ heterocyclyl, $C_5$-$C_{20}$ aryl or $C_{5-20}$ heteroaryl group, preferably a $C_{1-8}$alkyl group. Examples of ester groups include, but are not limited to, —C(=O)O$CH_3$, —C(=O)O$CH_2CH_3$, —C(=O)OC($CH_3$)$_3$, and —C(=O)OPh.

Amino: —$NR^1R^2$, wherein $R^1$ and $R^2$ are independently amino substituents, for example, hydrogen, a $C_1$-$C_8$ alkyl, $C_2$-$C_8$ alkenyl, $C_2$-$C_8$ alkynyl, $C_3$-$C_8$ cycloalkyl, $C_3$-$C_8$ heterocyclyl, $C_5$-$C_{20}$ aryl or $C_{5-20}$ heteroaryl group, preferably H or a $C_{1-8}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—$NH_2$), secondary (—$NHR^1$), or tertiary (—$NHR^1R^2$), and in cationic form, may be quaternary (—$^+NR^1R^2R^3$). Examples of amino groups include, but are not limited to, —$NH_2$, —$NHCH_3$, —$NHC(CH_3)_2$, —$N(CH_3)_2$, —$N(CH_2CH_3)_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Nitro: —NO$_2$.

Cyano (nitrile, carbonitrile): —CN.

Sulfine (sulfinyl, sulfoxide): —S(O)R, wherein R is a sulfine substituent, for example, a $C_1$-$C_8$ alkyl, $C_2$-$C_8$ alkenyl, $C_2$-$C_8$ alkynyl, $C_3$-$C_8$ cycloalkyl, $C_3$-$C_8$ heterocyclyl, $C_5$-$C_{20}$ aryl or $C_{5-20}$ heteroaryl group, preferably a $C_{1-8}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_1$-$C_8$ alkyl, $C_2$-$C_8$ alkenyl, $C_2$-$C_8$ alkynyl, $C_3$-$C_8$ cycloalkyl, $C_3$-$C_8$ heterocyclyl, $C_5$-$C_{20}$ aryl or $C_{5-20}$ heteroaryl group, preferably a $C_{1-8}$ alkyl group, including, for example, a fluorinated or perfluorinated $C_{1-8}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH; (esyl), —S(=O)$_2$C$_4$F$_9$ (nonaflyl), —S(O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

As used herein, unless defined otherwise in a claim, the term "treatment" refers to alleviating the specified condition, eliminating or reducing one or more symptoms of the condition, slowing or eliminating the progression of the condition As used herein, unless defined otherwise in a claim, the term "effective amount" means that amount of a drug or pharmaceutical agent that will elicit the biological or medical response of a tissue, system, animal, or human that is being sought, for instance, by a researcher or clinician.

As used herein, unless defined otherwise in a claim, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts thereof, may be administered as the raw chemical. Additionally, the active ingredient may be presented as a pharmaceutical composition.

This invention also relates to any one of the examples in the Experimental section.

The phrase "pharmaceutically acceptable salt," as used herein, refers to pharmaceutically acceptable organic or inorganic salts of an antibody-drug conjugate (ADC) or a linker-drug moiety. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

Compounds of the present invention may exist in solid or liquid form. In the solid state, it may exist in crystalline or noncrystalline form, or as a mixture thereof. The skilled artisan will appreciate that pharmaceutically acceptable solvates may be formed for crystalline or noncrystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds of the present invention or a salt thereof may exist in stereoisomeric forms (e.g., it contains one or more asymmetric carbon atoms). The individual stereoisomers (enantiomers and diastereomers) and mixtures of these are included within the scope of the present invention.

Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled forms of the compounds of the present invention, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are commonly used for their ease of preparation and detectability. 11C and 18F isotopes are useful in PET (positron emission tomography), and 125I isotopes are useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Pharmaceutical Composition of ADCS

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Cysteine Engineered Antibodies

The compounds of the invention include antibody-drug conjugates comprising cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0:0.7 to 1.0; or 0.8 to 1.0. To prepare a cysteine engineered antibody by mutagenesis, DNA encoding an amino acid sequence variant of the starting polypeptide is prepared by a variety of methods known in the art. These methods include, but are not limited to, preparation by site-directed (or oligonucleotide-mediated) mutagenesis. PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993. Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114(13):2721-2729; U.S. Pat. Nos. 7,521,541; 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the linker-drug intermediates of the present invention which have thiol-reactive, electrophilic groups such as maleimide or alpha-halo amides to form ADC with cysteine engineered antibodies (ThioMabs) and the drug (D) moiety. The location of the drug moiety can thus be designed, controlled, and known. The drug loading can be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A drug loading near 2 can be achieved and near homogeneity of the conjugation product ADC.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other moleculesiantigens that have a distinct characteristic (with respect to the antigen of interest). Cysteine engineered antibodies are prepared for conjugation with linker-drug intermediates by reduction and reoxidation of intrachain disulfide groups.

Tumor-Associated Antigens:

Antibodies, including but not limited to cysteine engineered antibodies, which may be useful in the antibody-drug conjugates of the invention in the treatment of cancer include, but are not limited to, antibodies against cell surface receptors and tumor-associated antigens (TAA). Certain tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to more specifically target cancer cells for destruction via antibody-based therapies. Examples of tumor-associated antigens TAA include, but are not limited to, those listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA listed below are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, and/or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

(1) BMPR1B (bone morphogenetic protein receptor-type IB, Genbank accession no. NM_001203)
ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4)
NP_001194 bone morphogenetic protein receptor, type IB/pid=NP_001194.1–
Cross-references: MIM:603248; NP_001194.1; AY065994

(2) E16 (LAT1, SLC7A5, Genbank accession no. NM_003486)
Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5: Page 133-136); US2003224454 (FIG. 3); WO2003025138 (Claim 12; Page 150);
NP_003477 solute carrier family 7 (cationic amino acid transporter, y+ system), member 5/pid=NP_003477.3—*Homo sapiens*
Cross-references: MIM:600182; NP_003477.3; NM_015923; NM_003486_1

(3) STEAP1 (six transmembrane epithelial antigen of prostate, Genbank accession no. NM_012449)
Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);
NP_036581 six transmembrane epithelial antigen of the prostate
Cross-references: MIM:604415; NP_036581.1; NM_012449_1

(4) 0772P (CA125, MUC16, Genbank accession no. AF361486)
J. Biol. Chem. 276 (29):27371-27375 (2001)); WO2004045553 (Claim 14); WO200292836 (Claim 6: FIG. 12); WO200283866 (Claim 15; Page 116-121); US2003124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823)
Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13: Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424)
J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV): WO200175177 (Claim 24; Page 139-140);
Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane Domain™ and short cytoplasmic domain, (semaphorin) 5B, Genbank accession no. AB040878)
Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11);

Accession: Q9P283; EMBL; AB040878; BAA95969.1. Genew; HGNC: 10737;

(8) PSCA hlg (2700050C12Rik, C530008016Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);
Cross-references: GI:37182378; AAQ88991.1: AY358628_1

(9) ETBR (Endothelin type B receptor, Genbank accession no. AY275463);
Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992: Arai H., et al J. Biol. Chem. 268, 3463-3470, 1993: Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attic T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206: WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF 124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);
Cross-references: LocusID:54894: NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)
Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);
Cross-references: GI:22655488; AAN04080.1; AF455138_1

(12) TrpM4 (BR22450. FLJ20041. TRPM4, TRPM4B, transient receptor potential cation channel, subfamily M, member 4, Genbank accession no. NM_017636)
Xu. X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);
Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212)
Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);
Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004)
Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674)
Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);
Cross-references: MIM: 147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130)
Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25);
Cross-references: MIM:606509; NP 110391.2; NM_030764_1

(17) HER2 (ErbB2. Genbank accession no. MI 1730)
Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (Claim 9); WO2003016475 (Claim 1); US200318592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2);
Accession: P40199: Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33: Page 85-87): JP05003790 (FIG. 6-8); WO9946284 (FIG. 9):
Cross-references: MIM: 179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053)
Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442)
Chan, J, and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)): WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42);
Cross-references: MIM:600997; NP_004433.2; NM_004442_1

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436)
Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788: WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10: Page 94): WO9840403 (Claim 2; FIG. 1B);
Accession: 043653; EMBL; AF043498; AAC39607.1.

(25) GEDA (Genbank accession No. AY260763);
AAP14954 lipoma HMGIC fusion-partner-like protein/pid=AAP14954.1—*Homo sapiens*
Species: *Homo sapiens* (human)
WO2003054152 (Claim 20); WO2003000842 (Claim 1); WO2003023013 (Example 3, Claim 20); US2003194704 (Claim 45);
Cross-references: GI:30102449; AAP14954.1; AY260763_1

(26) BAFF-R (B cell-activating factor receptor, BLyS receptor 3. BR3, Genbank accession No. AF116456); BAFF receptor ipid=NP_443177.1—*Homo sapiens*
Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616): WO200294852 (Col 136-137); WO200238766 (Claim 3; Page 133); WO200224909 (Example 3: FIG. 3);
Cross-references: MIM:606269; NP_443177.1; NM_052945_1; AF132600 (27) CD22 (B-cell receptor CD22-B isoform, BL-CAM, Lyb-8, Lyb8, SIGLEC-2, FLJ22814. Genbank accession No. AK026467);
Wilson et al (1991) J. Exp. Med. 173:137-146; WO2003072036 (Claim 1; FIG. 1);
Cross-references: MIM:107266; NP 001762.1: NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10)

WO2003088808, US20030228319; WO2003062401 (claim 9); US2002150573 (claim 4, pages 13-14); WO9958658 (claim 13, FIG. 16): WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1): 141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1)

WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class 11 molecule (1a antigen) that binds peptides and presents them to CD4+ T lymphocytes); 273 aa, pI: 6.56 MW: 30820 TM: 1 [P] Gene Chromosome: 6p21.3, Genbank accession No. NP_002111.1)

Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766: Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2)

Le et al (1997) FEBS Lett. 418(1-2):195-199; WO2004047749; WO2003072035 (claim 10); Touchman et al (2000) Genome Res. 10:165-173: WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1)

WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al (1996) Genomics 38(3):299-304: Miura et al (1998) Blood 92:2815-2822: WO2003083047 WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1)

WO2003077836; WO200138490 (claim 6, FIG. 18E-1-18-E-2); Davis et al (2001) Proc. Natl. Acad. Sci USA 98(17): 9772-9777; WO2003089624 (claim 8): EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse:AK089756, AY158090, AY506558; NP_112571.1 WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPPI, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2): 178-84;

(37) PMEL17 (silver homolog; SILV; D12S53E; PMEL17; (SI); (SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer. M. P. et al (2009) J. Biol. Chem. 284 (4), 2296-2306;

(38) TMEFF1 (transmembrane protein with EGF-like and two follistatin-like domains 1; Tomoregulin-1; H7365; C9orf2; C9ORF2; U19878; X83961) NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1; U95847; BC014962;

NM_145793) NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E; Ly67, RIG-E, SCA-2, TSA-1) NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;

(41) TMEM46 (shisa homolog 2 (*Xenopus laevis*); SHISA2) NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D1); Ly6-D, MEGT1) NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67) NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; (PTC); CDHF12; Hs.168114; RET51; RET-ELE1) NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226) NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19: Mm.4787) NP_006134.1; NM_006143.2; Montpetit, A, and Sinnett, D. (1999) Hum. Genet. 105 (1-2):162-164; O'Dowd, B. F. et al (1996) FEBS Lett. 394 (3):325-329;

(47) GPR54 (KISS1 receptor; KISS1R; GPR54; HOT7T 175; AXOR12) NP_115940.2; NM_032551.4; Navenot. J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing 1: LOC253982) NP_859069.2; NM_181718.3; Gerhard, D. S. et al (2004) Genome Res. 14 (10B):2121-2127;

(49) Tyrosinase (TYR; OCA1A; OCA1A; tyrosinase; SHEP3) NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627) NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A: GPCR41; FLJ11856; D15Ertd747e) NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

In one embodiment, the antibody binds to one or more of the following polypeptides: BMPR1B; E16; STEAP1; 0772P; MPF; Napi3b; Sema 5b; PSCA hlg; ETBR; MSG783; STEAP2; TrpM4; CRIPTO; CD21; CD79b; FcRH2; HER2; NCA; MDP; IL20Rα; Brevican; EphB2R; ASLG659; PSCA; GEDA; BAFF-R; CD22; CD79a; CXCR5; HLA-DOB; P2X5; CD72; LY64; FcRH1; IRTA2; TENB2; PMEL17; TMEFF1; GDNF-Ra1; Ly6E; TMEM46; Ly6G6D; LGR5; RET; LY6K; GPR19; GPR54; ASPHD1; Tyrosinase; TMEM118; GPR172A; and CD33.

In one embodiment, the antibody binds to BMPR1B;
In one embodiment, the antibody binds to E16;
In one embodiment, the antibody binds to STEAP1;
In one embodiment, the antibody binds to 0772P;
In one embodiment, the antibody binds to MPF;
In one embodiment, the antibody binds to Napi3b;
In one embodiment, the antibody binds to Sema 5b;
In one embodiment, the antibody binds to PSCA hlg;
In one embodiment, the antibody binds to ETBR;
In one embodiment, the antibody binds to MSG783;
In one embodiment, the antibody binds to STEAP2;
In one embodiment, the antibody binds to TrpM4;
In one embodiment, the antibody binds to CRIPTO;
In one embodiment, the antibody binds to CD21;
In one embodiment, the antibody binds to CD79b; In one embodiment, the antibody binds to FcRH2;
In one embodiment, the antibody binds to HER2;
In one embodiment, the antibody binds to NCA;
In one embodiment, the antibody binds to MDP;
In one embodiment, the antibody binds to IL20Rα;
In one embodiment, the antibody binds to Brevican;
In one embodiment, the antibody binds to EphB2R;
In one embodiment, the antibody binds to ASLG659;
In one embodiment, the antibody binds to PSCA;
In one embodiment, the antibody binds to GEDA;
In one embodiment, the antibody binds to BAFF-R;
In one embodiment, the antibody binds to CD22;
In one embodiment, the antibody binds to CD79a;
In one embodiment, the antibody binds to CXCR5;
In one embodiment, the antibody binds to HLA-DOB;
In one embodiment, the antibody binds to P2X5;
In one embodiment, the antibody binds to CD72;
In one embodiment, the antibody binds to LY64;
In one embodiment, the antibody binds to FcRH1;
In one embodiment, the antibody binds to IRTA2;
In one embodiment, the antibody binds to TENB2;
In one embodiment, the antibody binds to PMEL17;
In one embodiment, the antibody binds to TMEFF1;
In one embodiment, the antibody binds to GDNF-Ra1;
In one embodiment, the antibody binds to Ly6E;
In one embodiment, the antibody binds to TMEM46;
In one embodiment, the antibody binds to Ly6G6D;
In one embodiment, the antibody binds to LGR5;
In one embodiment, the antibody binds to RET;
In one embodiment, the antibody binds to LY6K;
In one embodiment, the antibody binds to GPR19;
In one embodiment, the antibody binds to GPR54;
In one embodiment, the antibody binds to ASPHD1;
In one embodiment, the antibody binds to Tyrosinase;
In one embodiment, the antibody binds to TMEM118;
In one embodiment, the antibody binds to GPR172A;
In one embodiment, the antibody binds to CD33.

The parent antibody may also be a fusion protein comprising an albumin-binding peptide (ABP) sequence (Dennis et al. (2002) "Albumin Binding As A General Strategy For Improving The Pharmacokinetics Of Proteins" J Biol Chem. 277:35035-35043; WO 01/45746). Antibodies of the invention include fusion proteins with ABP sequences taught by: (i) Dennis et al (2002) J Biol Chem. 277:35035-35043 at Tables III and IV, page 35038; (ii) US 20040001827 at [0076]; and (iii) WO 01/45746 at pages 12-13, and all of which are incorporated herein by reference. Antibodies may be produced using recombinant methods and compositions, e.g., as described in U.S. Pat. No. 4,816,567 and known in the art. In some embodiments, the antibody is produced in a eukaryotic host cell (e.g., mammalian host cell). In some embodiments, the antibody is produced in a prokaryotic host cell (e.g., *E. coli*).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability.

Drug Loading of ADC

The drug loading is the average number of drug moieties per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties is conjugated to an antibody during a conjugation reaction. An antibody may contain, for example, many lysine residues that do not react with the linker-drug intermediate (X-L-D) or linker reagent. Only the most reactive lysine groups may react with an amine-reactive linker reagent. Also, only the most reactive cysteine thiol groups may react with a thiol-reactive linker reagent or linker-drug intermediate. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio, "DAR") of an ADC may be controlled in several different manners, including: (i) limiting the molar excess of linker-drug intermediate or linker reagent relative to antibody, (ii) limiting the conjugation reaction time or temperature, and (iii) partial or limiting reductive conditions for cysteine thiol modification.

Where more than one nucleophilic or electrophilic group of the antibody reacts with a linker-drug intermediate, or linker reagent followed by dimer drug moiety reagent, then the resulting product is a mixture of Antibody-drug conjugate s with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody. Thus the antibody-drug conjugate compositions of the invention include mixtures of antibody-drug conjugate compounds where the antibody has one or more drug moieties and where the drug moieties may be attached to the antibody at various amino acid residues.

Thus, the present invention also comprises a collection of conjugates where each conjugate is of the same formula except for p.

Exemplary Drug Moieties

Non-limiting exemplary PBD dimer components of ADCs are of Formula A or B:

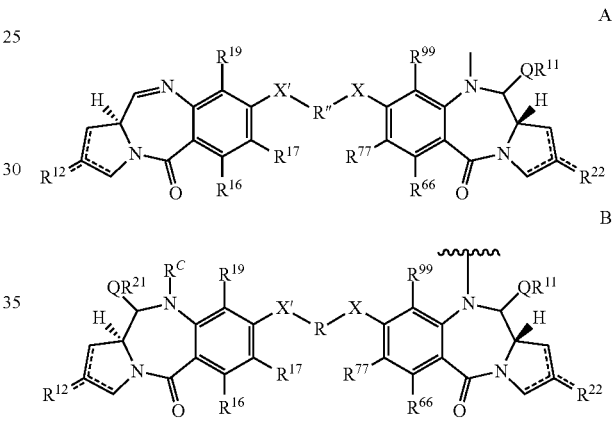

and salts and solvates thereof, wherein:

the wavy line indicates the covalent attachment site to the linker;

the dotted lines indicate the optional presence of a double bond between C1 and C2 or C2 and C3;

$R^{22}$ is independently selected from H, OH, =O, =CH$_2$, CN, $R^m$, O $R^m$, =CH—$R^D$, =C($R^D$)$_2$, O—SO$_2$—$R^m$, CO: $R^m$ and CO $R^m$, and optionally further selected from halo or dihalo, wherein $R^D$ is independently selected from $R^m$, CO$_2$ $R^m$, CO $R^m$, CHO, CO$_2$H, and halo;

$R^{66}$ and $R^{99}$ are independently selected from H, $R^m$, OH, O $R^m$, SH, S $R^m$, NH$_2$, NH $R^m$, N $R^m$ $R^p$, NO$_2$, Me$_3$Sn and halo;

$R^{77}$ is independently selected from H, $R^m$, OH, O $R^m$, SH, S $R^m$, NH$_2$, NH $R^m$, N $R^m$ $R^p$, NO$_2$, Me$_3$Sn and halo;

Q is independently selected from O, S and NH;

$R^{11}$ is either H, or $R^m$ or, where Q is O, SO$_3$M, where M is a metal cation;

$R^m$ and $R^p$ are each independently selected from optionally substituted C$_1$-C$_8$ alkyl, C$_2$-C$_8$ alkenyl, C$_2$-C$_8$ alkynyl, C$_3$-C$_8$ cycloalkyl, C$_{3-8}$ heterocyclyl, C$_5$-C$_{20}$ aryl and C$_5$-C$_{20}$ heteroaryl groups, and optionally in relation to the group N $R^m$ $R^p$, $R^m$ and $R^p$ together with the nitrogen atom to which they are attached form an optionally substituted 4-, 5-, 6- or 7-membered heterocyclic ring;

$R^{12}$, $R^{16}$, $R^{19}$, $R^{21}$ and $R^{17}$ are as defined for $R^{22}$, $R^{66}$, $R^{99}$, $R^{11}$ and $R^{77}$ respectively;

R" is a C$_3$-C$_{12}$ alkylene group, which chain may be interrupted by one or more heteroatoms. e.g. O, S, N(H), NMe and/or aromatic rings, e.g. benzene or pyridine, which rings are optionally substituted; and X and X' are independently selected from O, S and N(H); $R^C$ is a capping group.

In some embodiments, $R^{99}$ and $R^{19}$ are H.

In some embodiments, $R^{66}$ and $R^{16}$ are H.

In some embodiments, $R^{77}$ are $R^{17}$ are both $OR^{7A}$, where $R^{7A}$ is optionally substituted $C_1$-$C_4$ alkyl.

In some embodiments, $R^{7A}$ is Me. In other embodiments, $R^{7A}$ is $CH_2Ph$.

In some embodiments, X is O.

In some embodiments, $R^{11}$ is H. In other embodiments, $R^{11}$ is $SO_3M$, where M is a metal cation. The cation may be $Na^+$.

In some embodiments, there is no double bond present between C1 and C2, and C2 and C3.

In some embodiments, there is a double bond between C2 and C3 in each monomer unit.

In some embodiments, a double bond is present between C2 and C3 when $R^{12}$ and/or $R^{22}$ is $C_{5-20}$ aryl or $C_{1-8}$ alkyl.

In some embodiments, there is a double bond between C1 and C2, in each monomer unit.

In some embodiments, a double bond is present between C1 and C2 when $R^{12}$ and/or $R^{22}$ is $C_{5-20}$ aryl or $C_{1-8}$ alkyl.

In some embodiments, $R^{22}$ and $R^{12}$ are independently selected from H, =O, =CH$_2$, R$^m$, =CH—R$^D$, and =C(R$^D$)$_2$.

In some embodiments, $R^{22}$ and $R^{12}$ are independently selected from H and R$^m$, In some embodiments, $R^{22}$ and $R^{12}$ are H.

In some embodiments, $R^{22}$ and $R^{12}$ are independently R$^m$,

In some embodiments, $R^{22}$ and $R^{12}$ are independently optionally substituted $C_5$-$C_{20}$ aryl. In some embodiments, $R^{22}$ and $R^{12}$ are independently optionally substituted $C_{5-7}$ aryl. In some embodiments, $R^{22}$ and $R^{12}$ are independently optionally substituted $C_{8-10}$ aryl. In some embodiments, $R^{22}$ and $R^{12}$ are independently optionally substituted phenyl.

In some embodiments, $R^{22}$ and $R^{12}$ independently bear one to three substituent groups, with 1 and 2 being more preferred, and singly substituted groups being most preferred. The substituents may be any position.

Where $R^{22}$ and/or $R^{12}$ is a $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^{22}$ and/or $R^{12}$ are an optionally substituted $C_5$-$C_{20}$ aryl, the substituents may be selected from: Halo, Hydroxyl, Ether, Formyl, Acyl, Carboxy, Ester, Acyloxy, Amino, Amido, Acylamido, Aminocarbonyloxy, Ureido, Nitro, Cyano and Thioether.

In some embodiments, $R^{22}$ and $R^{12}$ are independently selected from =O, =CH$_2$, =CH—R$^D$, and =C(R$^D$)$_2$. Within the PBD compound, the group =CH—R$^D$ may have either configuration shown below:

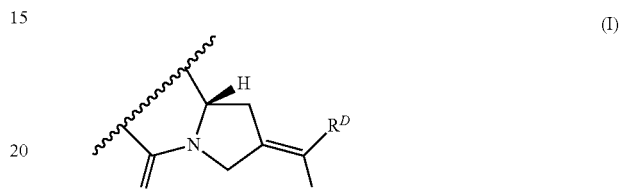

(I)

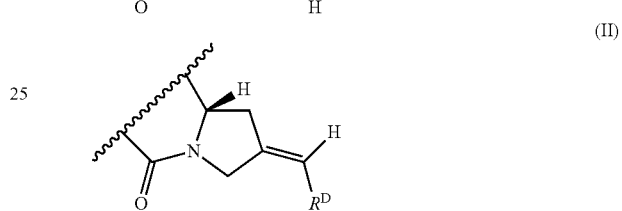

(II)

In some embodiments, the configuration is configuration (I).

In some embodiments, $R^{22}$ and $R^{12}$ are =CH$_2$.

In some embodiments, R" is selected from a $C_3$, $C_5$, $C_7$, $C_9$ and a $C_{11}$ alkylene group.

In some embodiments, R" is selected from a $C_3$, $C_5$ and a $C_7$ alkylene group.

In some embodiments, R" is a $C_3$ alkylene group or a $C_5$ alkylene group.

In some embodiments, an exemplary PBD dimer component of an ADC has the structure of Formula A(I):

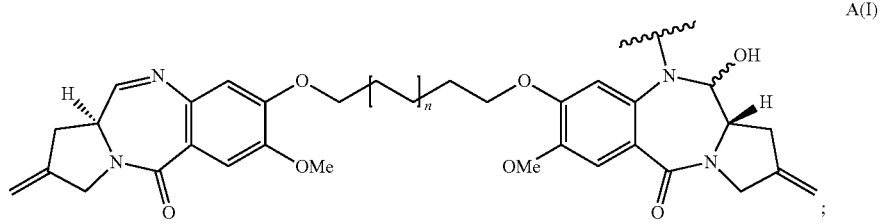

A(I)

wherein n is 0 or 1.

In some embodiments, an exemplary PBD dimer component of an ADC has the structure of Formula B(I):

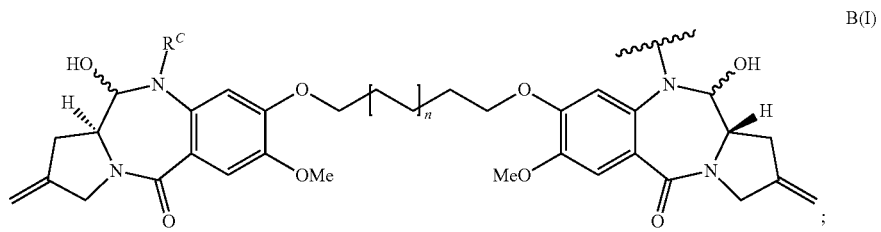

B(I)

wherein n is 0 or 1.

In some embodiments, an exemplary PBD dimer component of an ADC has the structure of Formula A(II):

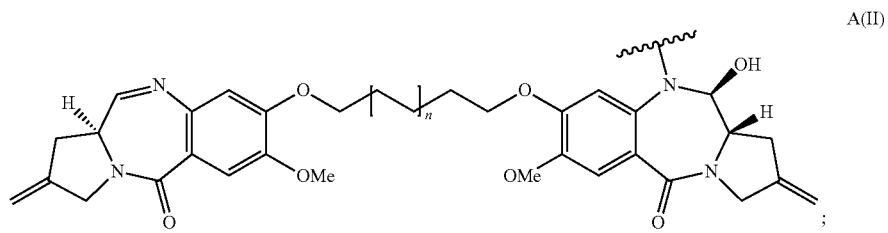

A(II)

wherein n is 0 or 1.

In some embodiments, an exemplary PBD dimer component of an ADC has the structure of Formula B(II):

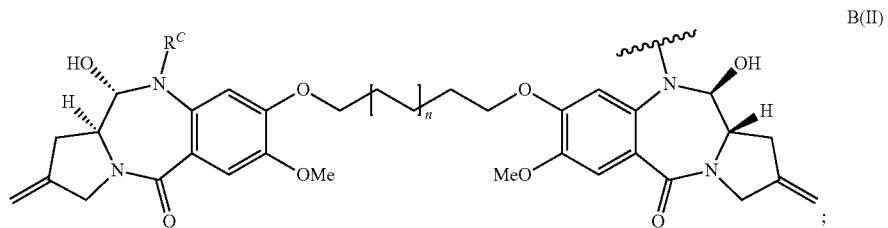

B(II)

wherein n is 0 or 1.

Further non-limiting exemplary PBD dimer components of ADCs are of Formula A(III):

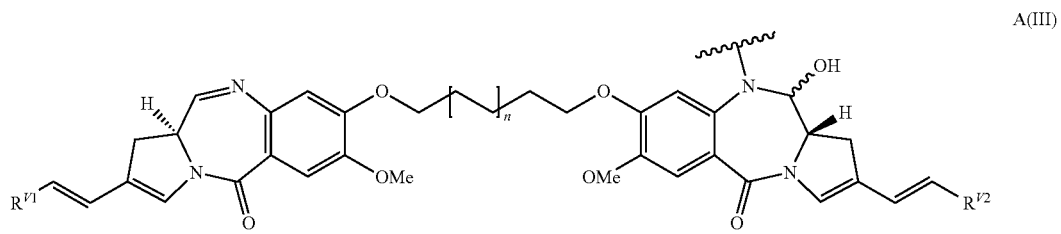

A(III)

wherein:
the wavy line indicates the covalent attachment site to the linker;
the wavy line connected to the OH indicates the S or R configuration;
$R^{V1}$ and $R^{V2}$ are independently selected from H, methyl, ethyl and phenyl (which phenyl may be optionally substituted with fluoro, particularly in the 4 position) and $C_{5-6}$ heterocycloalkyl; and
n is 0 or 1.

In some embodiments, $R^{V1}$ and $R^{V2}$ are independently selected from H, phenyl, and 4-fluorophenyl.

Further non-limiting exemplary PBD dimer components of ADCs are of Formula B(III):

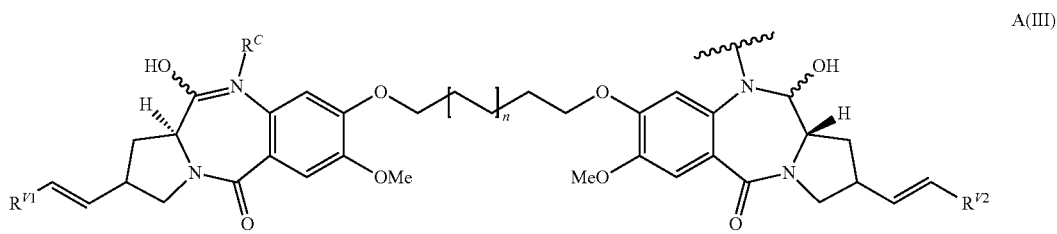

A(III)

wherein:
the wavy line indicates the covalent attachment site to the linker;
the wavy line connected to the OH indicates the S or R configuration;
$R^{V1}$ and $R^{V2}$ are independently selected from H, methyl, ethyl and phenyl (which phenyl may be optionally substituted with fluoro, particularly in the 4 position) and $C_{5-6}$ heterocycloalkyl; and
n is 0 or 1.

In some embodiments, $R^{V1}$ and $R^{V2}$ are independently selected from H, phenyl, and 4-fluorophenyl.

In some embodiments, an exemplary PBD dimer component of an ADC has the structure of Formula A(IV):

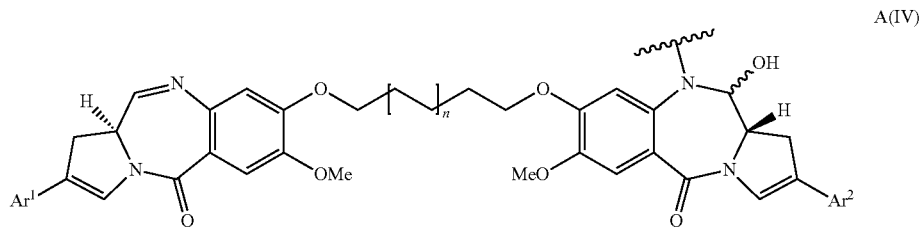

A(IV)

wherein $Ar^1$ and $Ar^2$ are each independently optionally substituted $C_{5-20}$ aryl or $C_{5-20}$ heteroaryl, and n is 0 or 1. $Ar^1$ and $Ar^2$ may be the same or different.

In some embodiments, an exemplary PBD dimer component of an ADC has the structure of Formula B(IV):

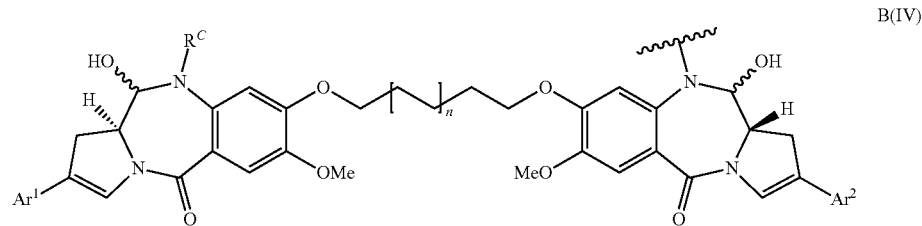

B(IV)

wherein $Ar^1$ and $Ar^2$ are each independently optionally substituted $C_{5-20}$ aryl or $C_{5-20}$ heteroaryl, and n is 0 or 1. $Ar^1$ and $Ar^2$ may be the same or different.

In one embodiment, $Ar^1$ and $Ar^2$ in each of the embodiments above are each independently selected from optionally substituted phenyl, furanyl, thiophenyl and pyridyl.

In one embodiment, $Ar^1$ and $Ar^2$ in each of the embodiments above is optionally substituted phenyl.

In one embodiment, $Ar^1$ and $Ar^2$ in each of the embodiments above is optionally substituted thien-2-yl or thien-3-yl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Non-limiting exemplary PBD dimer components of ADCs include Formulas C(I) and C(II):

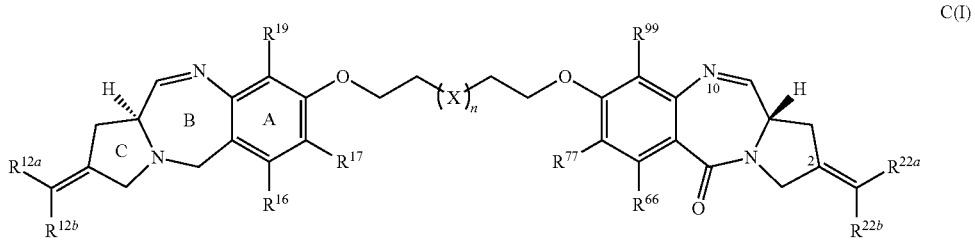

C(I)

-continued

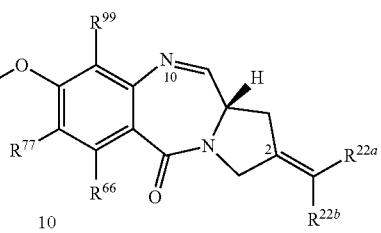

C(II)

Formulas C(I) and C(II) are shown in their N10-C11 imine form. Exemplary PBD drug moieties also include the carbinolamine and protected carbinolamine forms as well, as shown in the table below:

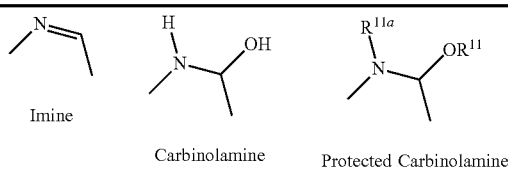

| Imine | Carbinolamine | Protected Carbinolamine | wherein:
$X$ is $CH_2$ (n=1 to 5), N, or O;
$R^{77}$ and $R^{17}$ are independently selected from $OR^m$ and $NR^{22b}$, where $R^m$ is a primary, secondary or tertiary alkyl chain containing 1 to 5 carbon atoms:
$R^{22a}$, $R^{12a}$, $R^{22b}$ and $R^{12b}$ are each independently selected from H, $C_1$-$C_8$ alkyl, $C_2$-$C_8$ alkenyl, $C_2$-$C_8$ alkynyl, $C_5$-$C_{20}$ aryl (including substituted aryls), $C_5$-$C_{20}$ heteroaryl groups, —$NH_2$, —NHMe, —OH, and —SH, where, in some embodiments, alkyl, alkenyl and alkynyl chains comprise up to 5 carbon atoms;

$R^{66}$ and $R^{16}$ are independently selected from H, OR, NHR, and $NR^{22b}$, where R is a primary, secondary or tertiary alkyl chain containing 1 to 5 carbon atoms;
$R^{99}$ and $R^{19}$ are independently selected from H, Me, and OMe;
$R^{11a}$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_5$-$C_{20}$ heteroaryl groups, where, in some embodiments, alkyl, alkenyl and alkynyl chains comprise up to 5 carbon atoms;
$R^{11}$ is H, $C_1$-$C_6$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);
$R^{11a}$ is H, $C_1$-$C_8$ alkyl, or a protecting group;
wherein a hydrogen of one of $R_1$, $R^{22a}$, $R^{12a}$, $R^{22b}$, $R^{12b}$ or $R^{11a}$ or a hydrogen of the —$OCH_2CH_2(X)_nCH_2CH_2O$— spacer between the A rings is replaced with a bond connected to the linker of the ADC.

Exemplary PDB dimer portions of ADC include, but are not limited to (the wavy line indicates the site of covalent attachment to the linker):

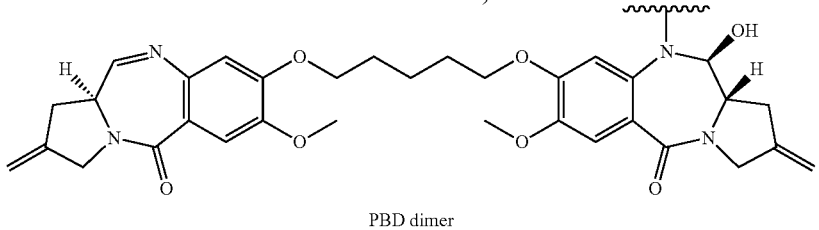

PBD dimer

Non-limiting exemplary embodiments of ADCs comprising PBD dimers and peptidomimetic linker include the following structures:

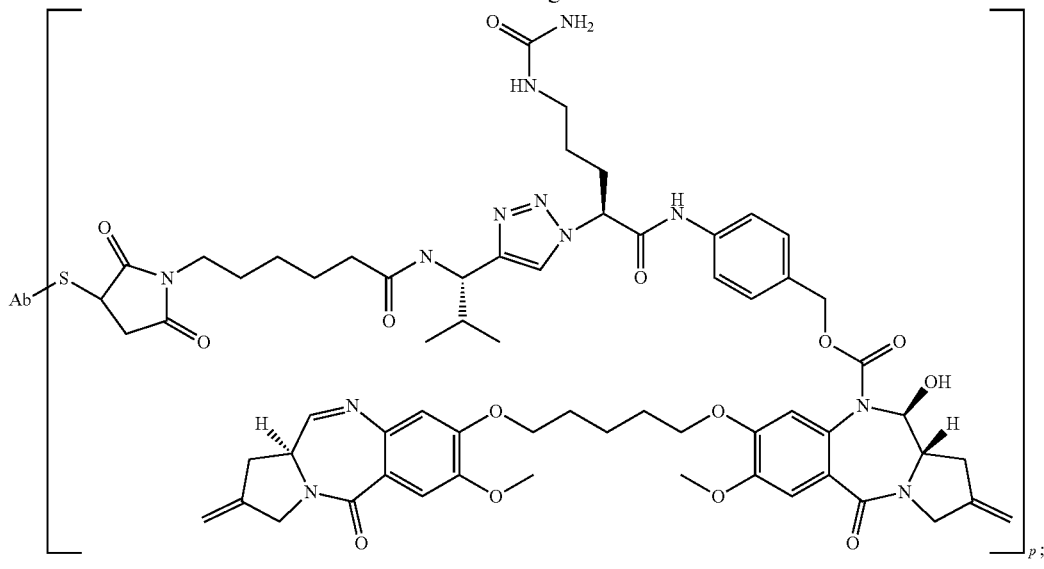

PBD dimer-PML-PAB-Ab

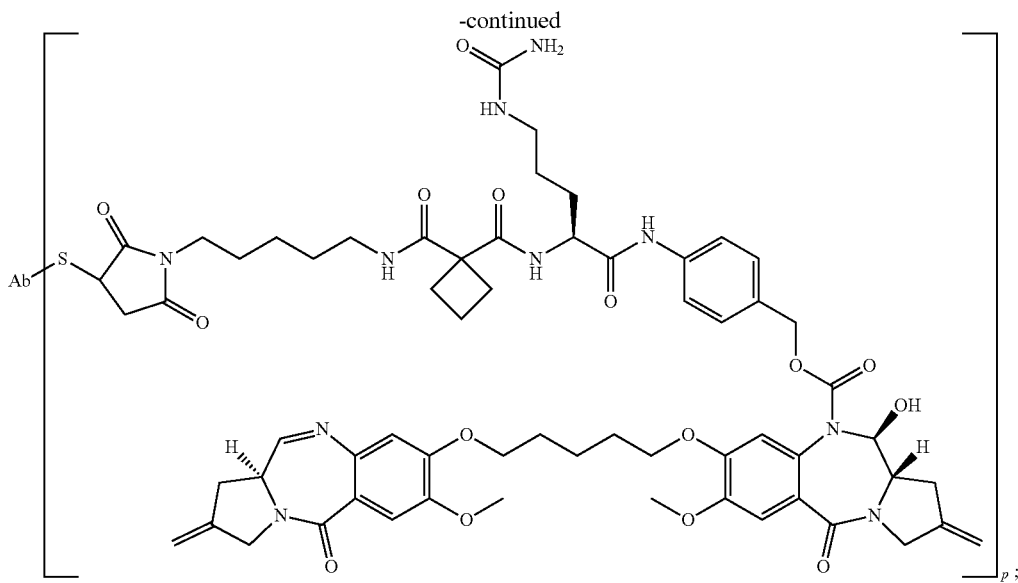
PBD dimer-PML-PAB-Ab
PBD dimers and ADC comprising PBD dimers may be prepared according to methods known in the art. See. e.g., WO 2009/016516: US 2009/304710; US 2010/047257; US 2009/036431: US 2011/0256157; WO 2011/130598; WO 2013/055987.
Synthesis
One possible synthesis route to a dimer intermediate of formula VIII is shown below:
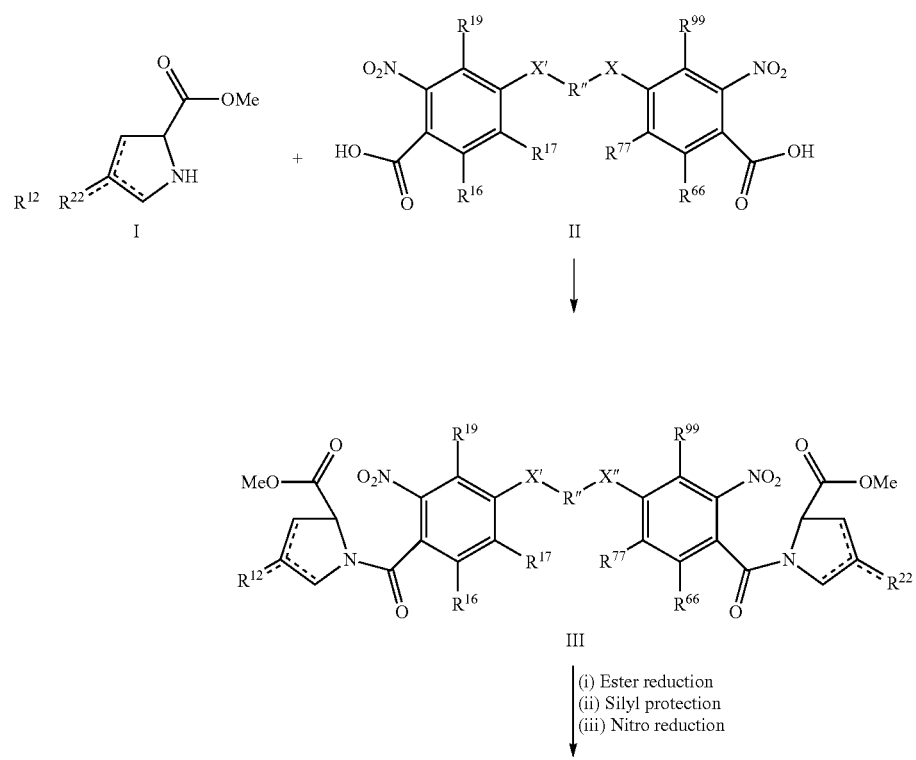

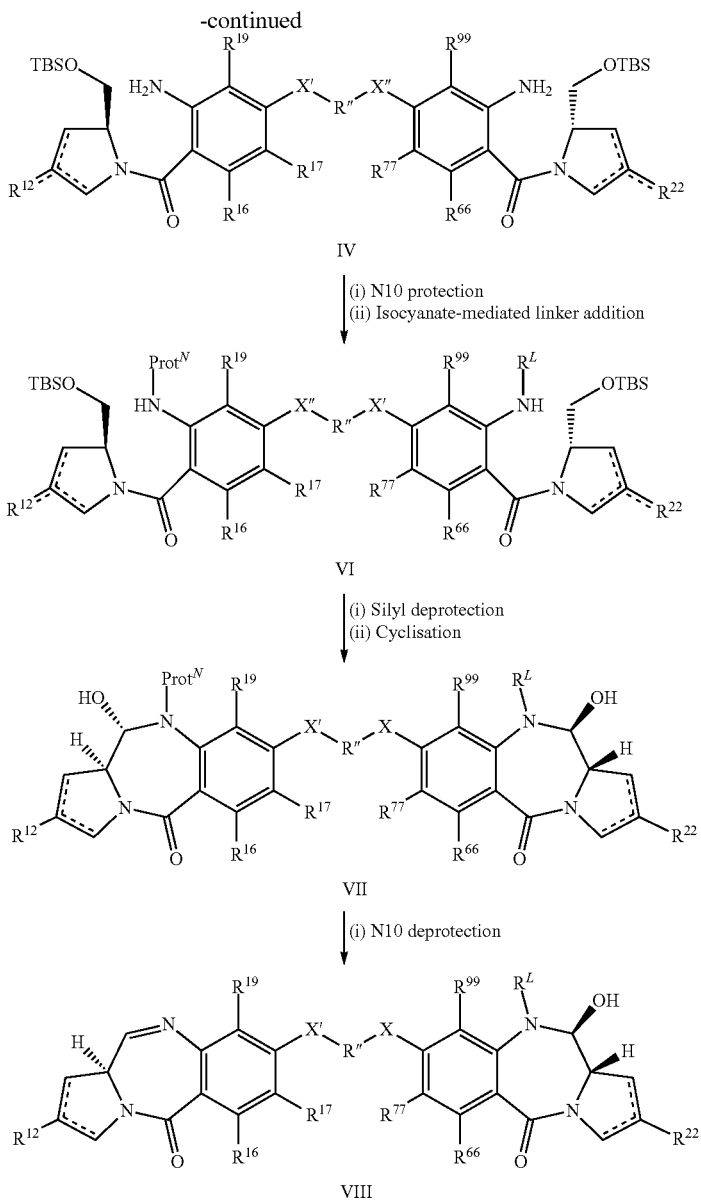

In the above scheme, $R^L$ represents the group that links to the antibody, i.e. L/Str-PM-Sp-, or a precursor of that group. In some methods of synthesis, the initial group added may be a protected version of PM-Sp- to which the Str group is added following deprotection.

Compounds where the non-bound PBD unit has $R^C$ at the N10 position may be made by a variation of the approach above, where $Prot^N$ is replaced by $R^C$ (or a precursor, with subsequent transformation).

In general, unsymmetrical dimers, with respect to their N10-C11 bonds, may be prepared by treating bis-amino compounds of formula IV with one equivalent of a chloroformate reagent in order to break the symmetry of the molecules. The remaining free amine can then be functionalised independently to introduce the linking group precursor (RL). Further functional group manipulation to close the PBD B-ring, remove protecting groups affords the target molecule.

Compounds of formula IV are typically prepared by coupling a suitably functionalised C-ring fragment (1) to an A-ring containing dimer core of formula II. C-ring fragments may be prepared from known carbamate protected methyl 4-oxoprolinate building blocks. Olefination under Wittig or Horner-Emmons conditions can be employed to furnish endo- or exo-unsaturated alkenes. C-ring and A-ring fragments can be coupled under standard conditions in the presence of triethylamine, using acid chloride derivatives of the A-ring fragments to give molecules of formula III. Symmetry may also be broken at this stage by introducing different C-rings. Compounds of type III can be reduced, without affecting endo or exo C-ring unsaturation, with zinc in acetic or formic acid to afford molecules of formula IV.

Alternatively, a suitable 4-hydroxy pyrrolidine building block may be coupled to a dimer core of formula II. The hydroxyl groups can be oxidized to ketones and then convened to enol triflates. Suzuki coupling can be used to introduce the pro C2 substituents (e.g. aryl, alkenyl etc). The nitro groups can then be reduced to amines, one amine is protected leaving the other free to bear the linker group.

Unsymmetrical carbamates of type VI can be prepared by treating bis-amines of type IV with a single equivalent of a commercially available (or readily prepared) chloroformates in the presence of pyridine or triethylamine. Chloroformates may be selected to afford appropriate carbamate based nitrogen protecting groups ($Prot^N$) which are orthogonal to those used in the pro-linker group ($R^L$). The RL carbamate may be introduced by converting the remaining amino group to an isocyanate and quenching it with the $R^L$ alcohol. Alternatively the $R^L$ alcohol can be converted to a chloroformate or functional equivalent (fluoroformate, p-nitrocarbonate, pentafluorocarbonate or hydroxybenzotriazole carbonate). Finally, the remaining amino group can be converted to a reactive p-nitrocarbamate, pentafluorocarbamate or hydroxybenzotriazole carbamate which can be displaced with the $R^L$ alcohol to afford molecules of formula VI.

Molecules of formula VII can be prepared from molecules of formula VI by removing the silyl protecting groups, with, for example, aqueous acetic acid. Oxidation with Dess-Martin periodinane (or alternatively TPAP/NMO, PDC or under Swern conditions) affords the ring closed product.

Conjugates of formula V may be prepared from molecules of formula VII by removal of the carbamate based nitrogen protection group.

Compound II

The synthesis of compounds of formula (II) is described in WO 2006/111759 and is also described by Gregson et al. (*J. Med. Chem.* 2001, 44, 1161-1174). The preparation of compound (II) as described therein is specifically incorporated by reference herein.

Reference is also made to the known methods of synthesising PBD dimers, including those reviewed in Antonow, D, and Thurston, D. E., *Chem. Rev.* 2011 111 (4), 2815-2864.

Further relevant disclosure may be found in WO 2010/091150. The intermediate compounds described in WO 2010/091150 may also be employed in the methods described above.

Indications and Methods of Treatment

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders. In certain embodiments, an ADC of the invention comprising an anti-NaPi3b antibody, such as those described above, is used in a method of treating solid tumor, e.g., ovarian, In another embodiment, an ADC of the invention comprising an anti-CD33 antibody, such as those described herein, is used in a method of treating hematological malignancies such as non-Hodgkin's lymphoma (NHL), diffuse large hematopoietic lymphoma, follicular lymphoma, mantle cell lymphoma, chronic lymphocytic leukemia, multiple myeloma, acute myeloid leukemia (AML), and myeloid cell leukemia (MCL), and including B-cell related cancers and proliferative disorders. See: U.S. Pat. No. 8,226,945; Li et al (2013) Mol. Cancer. Ther. 12(7): 1255-1265; Polson et al (2010) Leukemia 24:1566-1573; Poison et al (2011) Expert Opin. Investig. Drugs 20(1):75-85, the contents of which are incorporated by reference.

In another embodiment, an ADC of the invention comprising an anti-MUC16 antibody, such as those described herein, is used in a method of treating ovarian, breast and pancreatic cancers. The cancer may be associated with the expression or activity of a MUC16/CA125/O0772P polypeptide. See: WO 2007/001851: U.S. Pat. Nos. 7,989,595; 8,449,883; 7,723,485; Chen et al (2007) Cancer Res. 67(10): 4924-4932; Junutula, et al., (2008) Nature Biotech., 26(8): 925-932, the contents of which are incorporated by reference.

In certain embodiments, an ADC of the invention comprising an anti-HER2 antibody, such as those described above, is used in a method of treating cancer, e.g., breast or gastric cancer, more specifically HER2+breast or gastric cancer, wherein the method comprises administering such ADC to a patient in need of such treatment. In one such embodiment, the ADC comprises the anti-HER2 antibody trastuzumab or pertuzumab.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the Antibody-drug conjugate s may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

EXPERIMENTALS

General Experimental Methods
Analytical HPLC method

LC/MS (Shimadzu LCMS-2020) using a mobile phase of water (A) (formic acid 0.1%) and acetonitrile (B) (formic acid 0.1%). Gradient: initial composition 5% B held over 0.25 minutes, then increase from 5% B to 100% B over a 2 minutes period. The composition was held for 0.50 minutes at 100% B, then returned to 5% B in 0.05 minutes and hold there for 0.05 minutes. Total gradient run time equals 3 minutes. Flow rate 0.8 mL/min. Wavelength detection range: 190 to 800 nm. Oven temperature: 50° C. Column: Waters Acquity UPLC BEH Shield RP18 1.7 µm 2.1×50 mm.
Preparative HPLC Method Reverse-phase ultra-high-performance liquid chromatography (UPLC) was carried out on a Phenomenex Gemini NX 5µ C-18 150×21.20 mm column for preparative work. All experiments were performed with gradient conditions: initial fixed composition 13% B to 75% B over 15 min, held for 2.0 min at 75% B, then 75% B to 13% B within 0.10 min held at 13% for 2.90 min. Total duration of gradient run was 20.00 min. Eluents used were solvent A ($H_2O$ with 0.1% Formic acid) and solvent B ($CH_3CN$ with 0.1% Formic acid). Flow rate used was 20.0 ml/min for preparative HPLC. Detection was at 254 and 280 nm.
Synthesis of Intermediates a) Allyl 1-[[(1S)-11-[[4-(hydroxymethyl)phenyl]carbamoyl]-4-ureido-butyl]carbamoyl]cyclobutanecarboxylate (18)

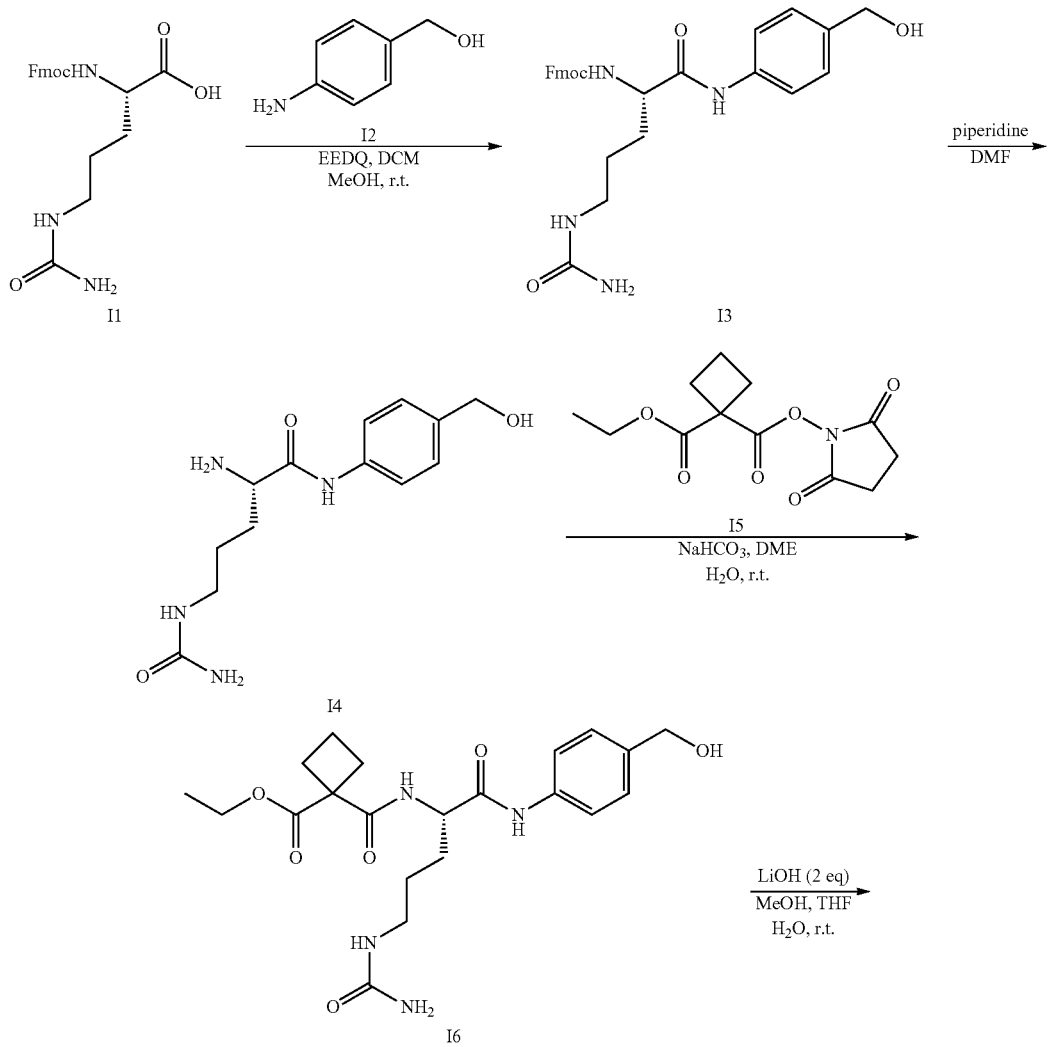

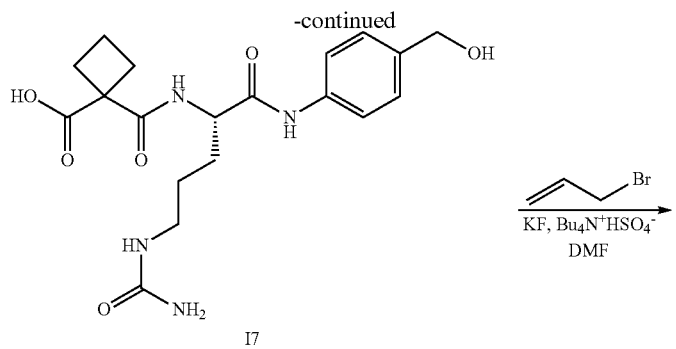

-continued

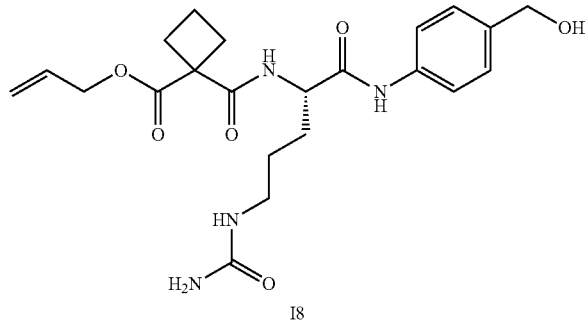

(i) To a solution of compound I1 (4.0 g, 10.0 mmol) in misture of DCM and McOH (100 mL/50 mL) were added 4-amino-phenyl-methanol (I2) (1.60 g, 13 mmol, 1.3 eq) and EEDQ (3.2 g, 13 mmol, 1.3 eq). After the mixture was stirred at room temperature for 16 hours under $N_2$, LCMS showed compound I1 was consumed. The mixture was concentrated to give a brown solid, and MTBE (200 mL) was added and the mixture was stirred at 15° C. for 2 hours. The solid was collected and washed with MTBE (50 mL×2) to give I3 (4.2 g, 84%) as an orange solid. LCMS (ESI, 5-95/1.5 min): RT=0.807 min, M+H$^+$=503.0; $^1$H NMR (400 MHz, DMSO-d$_6$) δ 9.98 (s, 1H), 7.89 (d, J=7.2 Hz, 2 H), 7.73 (d, J=4.8 Hz, 2 H), 7.70-7.65 (m, 1 H), 7.56 (d, J=8.4 Hz, 2 H), 7.41 (d, J=7.2 Hz, 2 H), 7.33-7.32 (m, 2 H), 7.24 (d, J=8.4 Hz, 2 H), 5.99 (m, 1 H), 5.42 (s, 2 H), 5.11-5.08 (t, J=5.6 Hz, 1 H), 4.36 (d, J=5.6 Hz, 2 H), 4.27 (s, 2 H), 4.26-4.18 (m, 2H), 3.33-2.94 (m, 2 H), 1.67-1.59 (m, 2 H), 1.47-1.40 (m, 2H).

(ii) To a stirred solution of compound I3 (4.2 g, 8.3 mmol) in dry DMF (20 mL) was added piperidine (1.65 mL, 17 mmol, 2.0 eq) dropwise at room temperature. The mixture was stirred at room temperature for 30 minutes, and solid start to precipitate. Dry DCM (50 mL) was added, and the mixture became transparent immediately. The mixture was stirred at r.t. for another 30 min, LCMS showed compound I3 consumed. It was concentrated under reduced pressure to remove piperidine, and the residue was partitioned between EtOAc and H$_2$O (50 mL/20 mL). Aqueous phase was washed with EtOAc (50 mL×2) and concentrated to give compound I4 (2.2 g, 94%) as a oil (contained small amount of DMF). $^1$H NMR (400 MHz, DMSO-d$_6$) δ 7.95 (s, 1H), 7.58 (d, J=8.4 Hz, 2 H), 7.23 (d, J=8.4 Hz, 2 H), 5.96-5.93 (m, 1 H), 5.37 (s, 2 H), 5.15-5.05 (m, 1 H), 4.42 (s, 2 H), 3.25 (m, 1 H), 3.0-2.9 (m, 2 H), 1.65-1.35 (m, 4 H).

(iii) To a solution of compound I5 (8.0 g, 29.7 mmol) in DME (50 mL) was added a solution of compound I4 (6.0 g, 21.4 mmol) and NaHCO$_3$ (7.48 g, 89.0 mmol) in water (30 mL). The mixture was stirred at room temperature for 16 hours. The mixture was concentrated to dryness under reduced pressure, and the residue was purified by column chromatography (DCM:MeOH=10:1) to give crude compound I6 (6.4 g, 68.7%) as a white solid. LCMS (ESI, 5-95/1.5 min): RT=0.692 min, M+H$^+$=435.0.

(iv) To a stirred solution of compound I6 (6.4 g, 14.7 mmol) in THF/McOH (20 mL/10 mL) was added a solution of LiOH.H$_2$O (1.2 g, 28.6 mmol) in H$_2$O (20 mL) at room temperature. After the reaction mixture was stirred at room temperature for 16 hours, solvent was removed under reduced pressure, and the residue was purified by pre-HPLC to give compound I7 (3.5 g, 58.5%). LCMS (ESI, 5-95/1.5 min): RT=0.575 min, M+H$^+$=406.9. $^1$H NMR (400 MHz, Methanol-d$_4$) δ 8.86 (d, J=8.4 Hz, 2 H), 8.51 (d, J=8.4 Hz, 2 H), 5.88-5.86 (m, 2 H), 5.78 (s, 2 H), 4.51-4.49 (m, 3H), 4.38-4.36 (m, 1 H), 3.86-3.84 (m, 1 H), 3.84-3.82 (m, 2 H), 3.82-3.80 (m, 1 H), 3.30-3.06 (m, 3 H), 2.96-2.91 (m, 1 H), 2.82-2.74 (m, 2 H).

(v) To a mixture of compound I7 (1.30 g, 3.2 mmol) in DMF (10 mL) was added KF (0.557 g, 9.6 mmol) and Bu$_4$N$^+$HSO$^-_4$ (0.101 g, 0.9 mmol). Compound I8 (0.50 mL, excess) was added dropwise. The mixture was stirred at 13° C. for 2 hours, and LCMS showed formation of compound I8 (86%) at 254 nm. The mixture was concentrated and purified by column chromatography (10%~15% MeOH in DCM) to give the product as an oil (1.1 g). The oil was dissolved in water and dried by lyophilization to give I8 as a powder (1.0 g, 70%). SFC analysis showed 89.4% ee. LCMS (ESI, 5-95/1.5 min): RT=0.721 min, M+H$^+$=447.0. $^1$H NMR (400 MHz, Methanol-d$_4$) δ 7.58 (d, J=8.8 Hz, 2 H), 7.31 (d, J=8.0 Hz, 2 H), 6.01-5.93 (m, 1 H), 5.35 (dd, J=16.8 Hz, 1H), 5.24-5.21 (m, J=9.6 Hz, 1 H), 4.69-4.68 (d, J=5.6 Hz, 1 H), 4.56-4.53 (m, 3 H), 3.25-3.05 (m, 2 H), 2.70-2.50 (m, 4 H), 2.10-2.00 (m, 1 H), 2.00-1.89 (m, 2 H), 1.76-1.58 (m, 1H), 1.58-1.49 (m, 2H).

b) (2S)-2-[4-[(1S)-1-amino-2-methyl-propyl]triazol-1-yl]-N-[4-(hydroxymethyl)phenyl]-5-ureido-pentanamide (10)

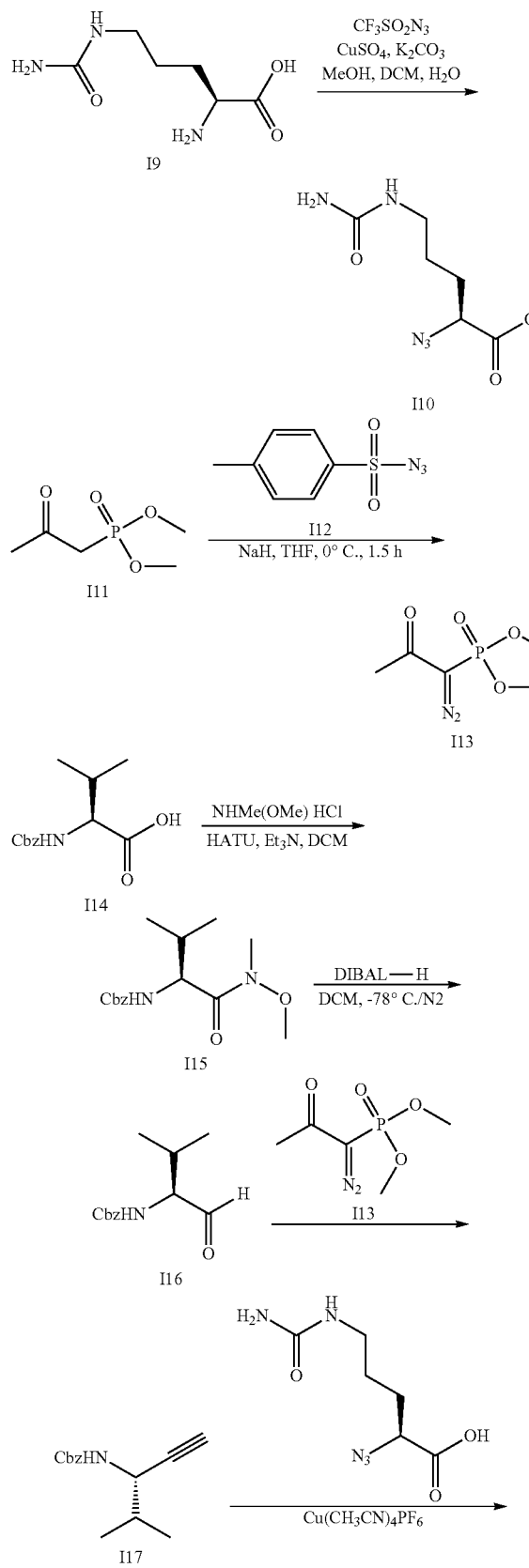

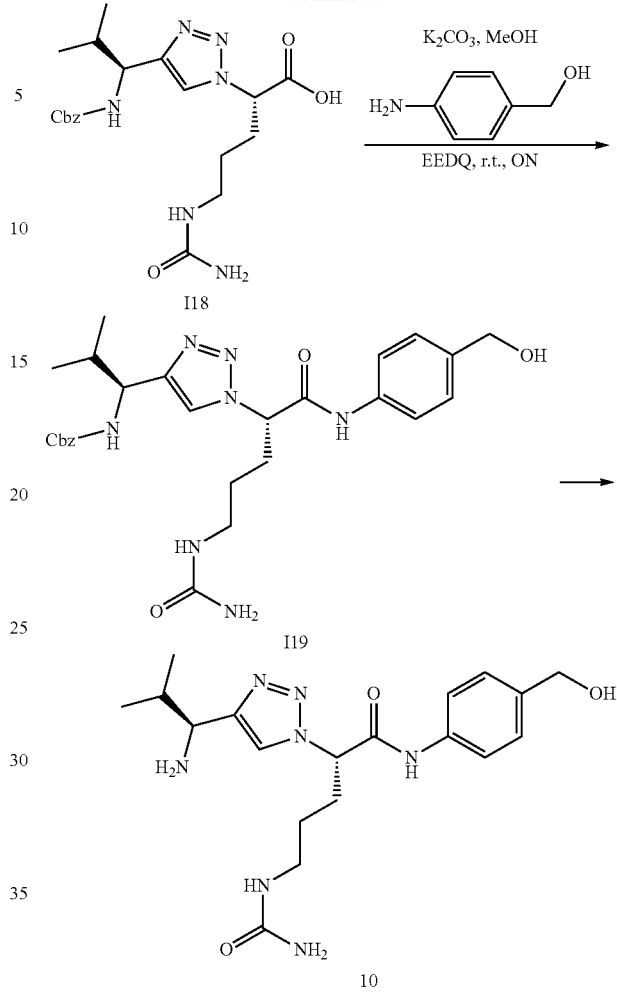

(i) A solution of $NaN_3$ (20 g, 285.7 mmol) was dissolved in distilled $H_2O$ (75 mL) and DCM (100 mL) was added. It was cooled in an ice bath and $Tf_2O$ (19.2 mL, 114.28 mmol) was added slowly over 30 min while stirring continued for 3 h. The mixture was place in a separation funnel and the $CH_2Cl_2$ phase collected. The aqueous portion was extracted with $CH_2Cl_2$ (50 mL×2). The organic fractions, containing the triflyl azide were pooled and washed once with saturated $Na_2CO_3$ (150 mL) and used without further purification. Compound I9 (10 g, 57.14 mmol) was combined with $K_2CO_3$ (11.83 g, 85.7 mmol) and $CuSO_4.5H_2O$ (1.43 g, 5.71 mmol) distilled $H_2O$ (50 mL) and MeOH (100 mL). The triflyl azide in $CH_2Cl_2$ (120 mL) generated above was added and the mixture was stirred at room temperature, overnight. Subsequently, the organic solvents were removed under reduced pressure and the aqueous slurry was diluted with $H_2O$ (100 mL). It was acidified to pH 6 with conc. HCl and diluted with 0.2 M pH 6.2 phosphate buffer (150 mL) and washed with EtOAC (100 mL×3) to remove sulfonamide byproduct. The aqueous phase was then acidified to pH 2 with conc. HCl. It was extracted with EtOAc/MeOH (20:1) (100 mL×4). The EtOAc/MeOH extractions were combined, dried over $Na_2SO_4$ and evaporated to give compound I10 without further purification (10 g, 87%).

(ii) To a solution of compound I11 (18.00 g, 108.36 mmol) in anhydrous THF (300 mL) was added NaH (5.2 g, 130.03 mmol) at 0° C. The mixture was stirred at 0° C. for 1 hour, then compound I12 (25.64 g, 130.03 mmol) was added slowly into the mixture. The reaction mixture was stirred at 0° C. for 0.5 hour. The mixture was filtered, concentrated, and purified by column chromatography on silica gel (PE: EtOAc=1:1) to give the desired product I13 (20 g, 96%). $^1$H NMR (400 MHz, CDCl$_3$) δ 3.84 (s, 3H), 3.81 (s, 3H), 2.25 (s, 3H).

(iii) To a mixture of compound 114 (20.0 g, 79.59 mmol) in anhydrous DCM (150 mL) was added Et$_3$N (24.16 g, 238.77 mmol) and HATU (45.40 g, 119.39 mmol). The mixture was stirred at room temperature for 15 minutes, then NHMe(OMe) HCl (11.65 g, 119.39 mmol) was added. The reaction mixture was stirred at room temperature overnight. The mixture was diluted with DCM, washed with saturated aq. Na$_2$CO$_3$ (100 mL×3), saturated citric acid (100 mL×3) and brine (100 mL). The organic layer was dried, concentrated, and purified by column chromatography on silica gel (PE: EtOAc=10:1) to give the desired product I15 (20.0 g, 85.4%). $^1$H NMR (400 MHz, DMSO-d$_6$) δ 7.97 (s, 1H), 7.73 (d, J=9.2 Hz, 1H), 7.36-7.29 (m, 5H), 6.01 (s, 1H), 5.40 (dd, J=5.2 Hz, 1H), 5.08-4.99 (m, 2H), 4.58 (dd, J=2.8 Hz, 1H), 2.99-2.94 (m, 2H), 2.21-2.02 (m, 4H), 1.02-1.33 (m, 2H), 0.86-0.77 (m, 6H).

(iv) Compound I15 (12 g, 40.77 mmol) was dissolved in anhydrous DCM (40 mL) and the resulting solution was cooled to −78° C. with a dry ice/acetone bath. DIBAL-H (122.3 mL, 122.3 mmol, 1.0 M in toluene) was added dropwise and the resulting solution was stirred at −78° C. for 4 hours. Excess hydride was quenched by the addition of MeOH (40 mL) at −78° C. and the resulting solution was warmed to room temperature. The solution was evaporated to give the compound I16 (~9.2 g, 96%) without further purification.

(v) To a solution of compound I16 (crude, ~9.2 g, 39.1 mmol) and compound I13 (11.27 g, 58.65 mmol) in MeOH (150 mL) was added K$_2$CO$_3$ (16.2 g, 117.3 mmol). The reaction mixture was stirred at room temperature overnight. The mixture was concentrated in vacuum, and purified by column chromatography on silica gel (PE: EtOAc=50:1) to give the desired product I17 (4 g, 44%).

(vi) To the solution of compound I17 (4.0 g, 17.29 mmol) and Compound I10 (4.17 g, 20.75 mmol) in DMF (15 mL) was added Cu(CH$_3$CN)$_4$PF$_6$ (1.29 g, 3.46 mmol). The reaction mixture was stirred at 60° C. for 2 hours. The mixture was purified to give compound I18 (5.0 g, 66.8%). $^1$H NMR (400 MHz, DMSO-d$_6$) δ 7.97 (s, 1H), 7.73 (d, J=9.2 Hz, 1H), 7.36-7.29 (m, 5H), 6.01 (s, 1H), 5.40 (dd, J=5.2 Hz, 1H), 5.08-4.99 (m, 2H), 4.58 (dd, J=2.8 Hz, 1H), 2.99-2.94 (m, 2H), 2.21-2.02 (m, 4H), 1.02-1.33 (m, 2H), 0.86-0.77 (m, 6H).

(vii) To a solution of compound I18 (crude, ~3.8 g, 8.79 mmol) in DMF (15 mL) was added EEDQ (4.34 g, 17.58 mmol) and compound I19 (1.62 g, 13.18 mmol) at 0° C. The reaction mixture was stirred at room temperature, under N$_2$ overnight. The mixture was purified by prep-HPLC to give compound I20 (650 mg, 13.7%). $^1$H NMR (400 MHz, DMSO-d$_6$) δ 10.52 (d, J=6.8 Hz, 1H), 8.05 (s, 1H), 7.72 (d, J=9.2 Hz, 2H), 7.33-7.23 (m, 7H), 6.01 (s, 1H), 5.47-5.43 (m, 3H), 5.04-4.96 (m, 2H), 4.59-4.54 (m, 1H), 4.41 (s, 2H), 3.04-2.94 (m, 3H), 2.09-1.97 (m, 4H), 1.24 (t, J=6.4 Hz, 2H), 0.82-0.74 (m, 6H).

(viii) To the reaction of compound I20 (650 mg, 1.21 mmol) in MeOH (15 mL) was added Pd/C (300 mg). The reaction mixture was stirred at room temperature under H$_2$ for 2 hours. The reaction mixture was filtered and the filtrate was concentrated to give I10 (450 mg, 92%). LCMS (ESI): RT=0.611 min, M+H+=404.0, method=5-95/1.5 min. $^1$H NMR (400 MHz, DMSO-d$_6$) δ 10.55 (s, 1H), 8.03 (d, J=7.6 Hz, 1H), 7.51 (d, J=8.4 Hz, 2H), 7.23 (d, J=8.4, 2H), 6.05 (t, J=5.6 Hz, 1H), 5.46-5.42 (m, 3H), 5.14 (s, 1H), 4.40 (s, 2H), 3.76 (d, J=5.2 Hz, 2H), 3.00-2.93 (m, 3H), 2.09-2.04 (m, 2H), 1.90-1.87 (m, 1H), 1.25-1.21 (m, 2H), 0.82-0.77 (m, 6H).

(c) Allyl N-[(1S)-1-[1-[(1S)-1-[[4-(hydroxymethyl)phenyl]carbamoyl]-4-ureido-butyl]triazol-4-yl]-2-methyl-propyl]carbamate (2)

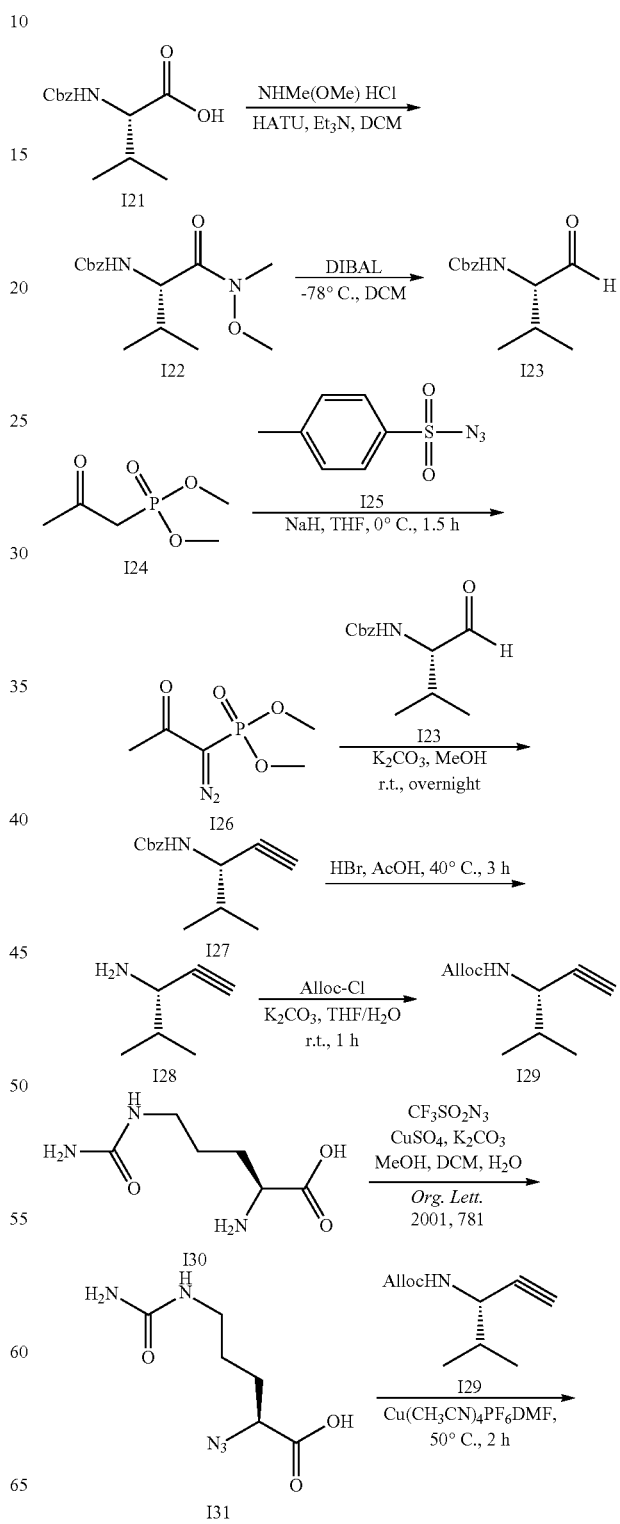

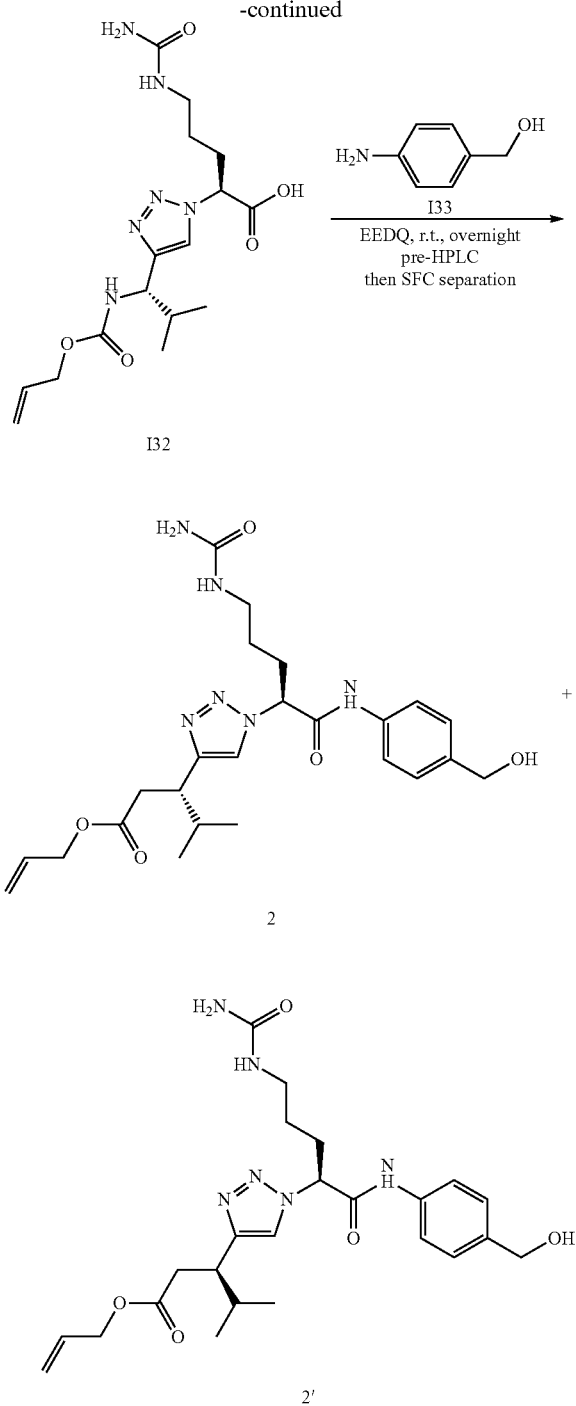

(i) To a mixture of compound I21 (20.0 g, 79.59 mmol) in anhydrous DCM (150 mL) was added Et₃N (24.16 g, 238.77 mmol) and HATU (45.40 g, 119.39 mmol). After the mixture was stirred at room temperature for 15 minutes, NHMe(OMe)·HCl (11.65 g, 119.39 mmol) was added. The reaction mixture was stirred at r.t. overnight. The mixture was diluted with DCM, and washed with saturated aq. Na₂CO₃ (100 mL×3), saturated citric acid (100 mL×3) and brine (100 mL). The organic layer was dried, concentrated, and purified by column chromatography on silica gel (PE: EtOAc=2:1) to give the desired product I22 (20.0 g, 85.4%).

(ii) Compound I22 (5.0 g, 16.99 mmol) was dissolved in anhydrous CH₂Cl₂ (20 mL) and the resulting solution was cooled to −78° C. in a dry ice/acetone bath. DIBAL-H (51.0 mL, 51.00 mmol, 1.0 M in toluene) was added dropwise and the resulting solution was stirred at −78° C. for 4 hours. Excess hydride was quenched by the addition of MeOH (10 mL) at −78° C. and the resulting solution was warmed to room temperature. The solution was evaporated to give compound I23 (~3.2 g, 80%) without further purification.

(iii) To a solution of compound I24 (6.00 g, 36.12 mmol) in anhydrous THF (200 mL) was added NaH (1.73 g, 43.34 mmol) at 0° C. The mixture was stirred at 0° C. for 1 hour, then compound I25 (7.12 g, 36.12 mmol) was added slowly. The resulting mixture was stirred at 0° C. for 0.5 hours. The mixture was filtered, concentrated, and purified by column chromatography on silica gel (EtOAc) to give the desired product (6.0 g, 86.5%). ¹H NMR (400 MHz, DMSO-d₆) δ 3.76 (s, 3H), 3.73 (s, 3H), 2.22 (s, 3H).

(iv) To a solution of compound I23 (crude, ~3.20 g, 13.60 mmol) and compound I26 (5.23 g, 27.20 mmol) in MeOH (50 mL) was added K₂CO₃ (5.64 g, 40.80 mmol). The reaction mixture was stirred at room temperature overnight. The mixture was concentrated in vacuum, and purified by column chromatography on silica gel (PE: EtOAc=5:1) to give the desired product I27 (2.00 g, 63.6%). ¹H NMR (400 MHz, DMSO-d₆) δ 7.77 (d, J=8.8 Hz, 1H), 7.39-7.30 (m, 5H), 5.04 (s, 2H), 4.12-4.07 (m, 1H), 3.19 (d, J=2.4 Hz, 1H), 1.83-1.74 (m, 1H), 0.94 (d, J=6.8 Hz, 3H), 0.90 (d, J=6.8 Hz, 3H).

(v) To a solution of compound I27 (2.90 g, 12.54 mmol) in HOAc (20 mL) was added aq. HBr solution (30 mL, 148.31 mmol). After the reaction mixture was stirred at 40° C. for 3 hours, it was concentrated in vacuum to remove the solvent. The residue was taken up by H₂O (40 mL), and washed with EtOAc (20 mL×3). Aqueous layer was adjusted to pH 10 by a Na₂CO₃ solution, and extracted with EtOAc again (20 mL×3). The combined organic layer was dried over Na₂SO₄, filtered, adjusted to pH 5 by HCOOH, and concentrated to give the desired product I28 as a salt (1.20 g, 66.8%). ¹H NMR (400 MHz, DMSO-d₆) δ 3.89 (dd, J=5.2 Hz, 2.0 Hz, 1H), 3.59 (d, J=2.4 Hz, 1H), 1.83-1.74 (m, 1H), 0.96 (dd, J=6.4, 4.8 Hz, 6H).

(vi) To a solution of compound I28 (1.30 g, 9.08 mmol) in THF/H₂O (20 mL/4 mL) was added K₂CO₃ (3.76 g, 27.24 mmol). Alloc-Cl (1.64 g, 13.62 mmol) was added dropwise into the mixture at 0° C. The reaction mixture was stirred at room temperature for 0.5 hours. The mixture was extracted with EtOAc (20 mL×3) and washed with H₂O (20 mL). The combined organic layer was dried over Na₂SO₄, filtered and concentrated. The residue was purified by column chromatography on silica gel (PE: EtOAc=5:1) to give compound I29 (1.3 g, 79.0%). ¹H NMR (400 MHz, DMSO-d₆) δ 7.71 (d, J=8.8 Hz, 1H), 5.96-5.86 (m, 1H), 5.31-5.26 (m, 1H), 5.20-5.16 (m, 1H), 4.48 (d, J=5.2 Hz, 2H), 4.09-4.04 (m, 1H), 3.19 (d, J=2.0 Hz, 1H), 1.82-1.73 (m, 1H), 0.94 (d, J=6.8 Hz, 3H), 0.89 (d, J=6.8 Hz, 3H).

(vii) A solution of NaN₃ (7.80 g, 119.98 mmol) was dissolved in distilled H₂O (20 mL) and CH₂Cl₂ (40 mL) was added. It was cooled in an ice bath and Tf₂O (3.0 mL, 19.65 mmol) was added slowly over 5 min and stirred for additional 2 hours. The mixture was place in a separation funnel and the CH$_2$Cl$_2$ phase collected. The aqueous portion was extracted with CH$_2$Cl$_2$ (30 mL×2). The organic fractions, containing the triflyl azide were pooled and washed once with saturated Na$_2$CO$_3$ (40 mL) and used without further purification. Compound I30 (1.80 g, 10.27 mmol), K$_2$CO$_3$ (2.13 g, 15.41 mmol) and CuSO$_4$.5H$_2$O (257 mg, 1.03 mmol) was mixed in distilled H$_2$O (40 mL) and MeOH (80 mL). The triflyl azide in CH$_2$Cl$_2$ (100 mL) generated above was added and the mixture was stirred at room temperature overnight. Subsequently, the organic solvents were removed under reduced pressure and the aqueous slurry was diluted with H$_2$O (50 mL). It was acidified to pH 6 with conc. HCl and diluted with 0.2 M pH 6.2 phosphate buffer (50 mL) and washed with EtOAc (100 mL×3) to remove sulfonamide byproduct. The aqueous phase was then acidified to pH 2 with conc. HCl. It was extracted with EtOAc/MeOH (20:1) (100 mL×4). These EtOAc/MeOH extractions were combined, dried over Na$_2$SO$_4$ and evaporated to giving compound I31 without further purification (1.6 g, 77.4%).

(viii) To the solution of compound I31 (1.70 g, 8.45 mmol) and compound I29 (1.23 g, 6.76 mmol) in DMF (10 mL) was added Cu(CH$_3$CN)$_4$PF$_6$ (315 mg, 0.85 mmol). The reaction mixture was stirred at 50° C. for 2 hours, and the mixture was used directly for next step.

(ix) To the mixture of compound I32 (crude, ~2.50 g, 6.54 mmol) in DMF (15 mL) was added EEDQ (2.42 g, 9.81 mmol) and compound 133 (1.21 g, 9.81 mmol). The reaction mixture was stirred at 0° C.~r.t under N$_2$ protection overnight. The mixture was purified by pre-HPLC (FA) to give the crude product, then washed with MTBE to give the pure product. After SFC separation, 2 (1.10 g, 34.5%) and 2' (220 mg, 6.9%) were obtained.

2: LCMS (ESI): RT=0.973 min, M+H+=488.0, method=10-80/2 min. $^1$H NMR (400 MHz, DMSO-d$_6$) δ 10.53 (s, 1H), 8.08 (s, 1H), 7.66 (d, J=9.6 Hz, 1H), 7.54 (dd, J=6.8, 2.0 Hz, 2H), 7.26 (d, J=8.4 Hz, 2H), 6.02 (t, J=5.6 Hz, 1H), 5.94-5.87 (m, 1H), 5.48 (dd, J=8.8, 6.8 Hz, 1H), 5.41 (s, 2H), 5.28 (dd, J=17.2, 1.6 Hz, 1H), 5.16 (d, J=10.4, 1.2 Hz, 1H), 5.13 (t, J=5.6 Hz, 1H), 4.58 (dd, J=9.2, 6.8 Hz, 1H), 4.49-4.46 (m, 2H), 4.44 (d, J=5.6 Hz, 2H), 3.04-2.97 (m, 2H), 2.14-2.01 (m, 3H), 1.29-1.23 (m, 2H), 0.85 (d, J=6.8 Hz, 3H), 0.78 (d, J=6.8 Hz, 3H).

2': LCMS (ESI): RT=0.980 min, M+H+=488.0, method=10-80/2 min. $^1$H NMR (400 MHz, DMSO-d$_6$) δ 10.52 (s, 1H), 8.07 (s, 1H), 7.64 (d, J=9.2 Hz, 1H), 7.54 (d, J=8.4 Hz, 2H), 7.27 (d, J=8.8 Hz, 2H), 6.02 (t, J=5.6 Hz, 1H), 5.95-5.86 (m, 1H), 5.47 (dd, J=8.8, 6.8 Hz, 1H), 5.42 (s, 2H), 5.28 (dd, J=16.8, 1.2 Hz, 1H), 5.16 (d, J=11.6 Hz, 1H), 5.13 (t, J=6.0 Hz, 1H), 4.57 (dd, J=9.2, 7.2 Hz, 1H), 4.49-4.46 (m, 2H), 4.44 (d, J=5.6 Hz, 2H), 3.06-2.94 (m, 2H), 2.16-2.02 (m, 3H), 1.29-1.25 (m, 2H), 0.85 (d, J=6.8 Hz, 3H), 0.78 (d, J=6.8 Hz, 3H).

HPLC separation condition (2 & 2'):
Instrument: SHIMADZU LC-8A
Column: synergi-10 μm, 250×50 mmI.D.
Mobile phase: A for H$_2$O (Add 2‰ FA, v/v) and B for MeCN
Gradient: B 10-50%
Flow rate: 80 mL/min
Monitored Wavelength: 220 nm/254 nm
Run length: 22 min/25 min
SFC separation condition (2 & 2'):
Instrument: Thar SFC 80
Column: Chiral PAK AD, 5 μm, Daicel Chemical Industries, Ltd
250×30 mmI.D.
Mobile phase: A: Supercritical C02, B:EtOH (contained 0.1% NH3H2O), A:B=70:30 at 60 ml/min
Column Temp: 38° C.
Nozzle Pressure: 100 Bar
Nozzle Temp: 60° C.
Evaporator Temp: 20° C.
Trimmer Temp: 25° C.
Wavelength: 220 nm Example 1

Preparation of [4-[[(2S)-2-[4-[(1S)-1-[6-(2,5-dioxopyrrol-1-yl)hexanoylamino]-2-methyl-propyl]triazol-1-yl]-5-ureido-pentanoyl]amino]phenyl]methyl (6S,6aS)-3-[5-[[(6aS)-2-methoxy-8-methylene-11-oxo-7,9-dihydro-6aH-pyrrolo [2,1-c][1,4]benzodiazepin-3-yl]oxy]pentoxy]-6-hydroxy-2-methoxy-8-methylene-11-oxo-6,6a,7,9-tetrahydropyrrolo[2, 1-c][1.4]benzodiazepine-5-carboxylate (PBD-LD2)

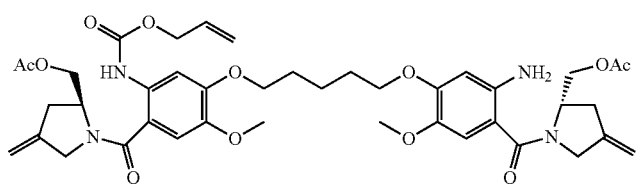

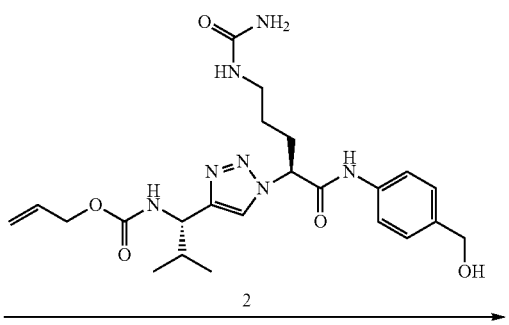

-continued
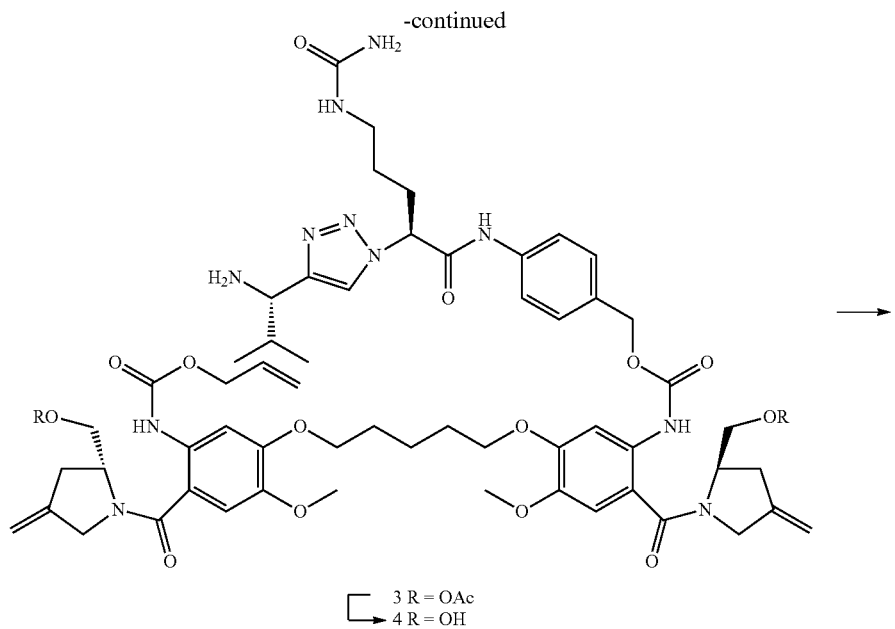
3 R = OAc
4 R = OH

-continued

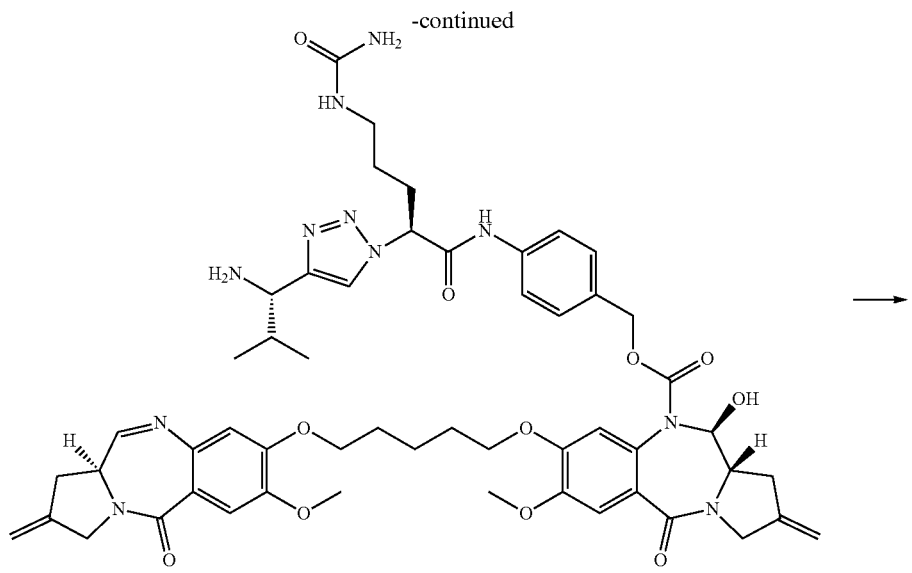

6

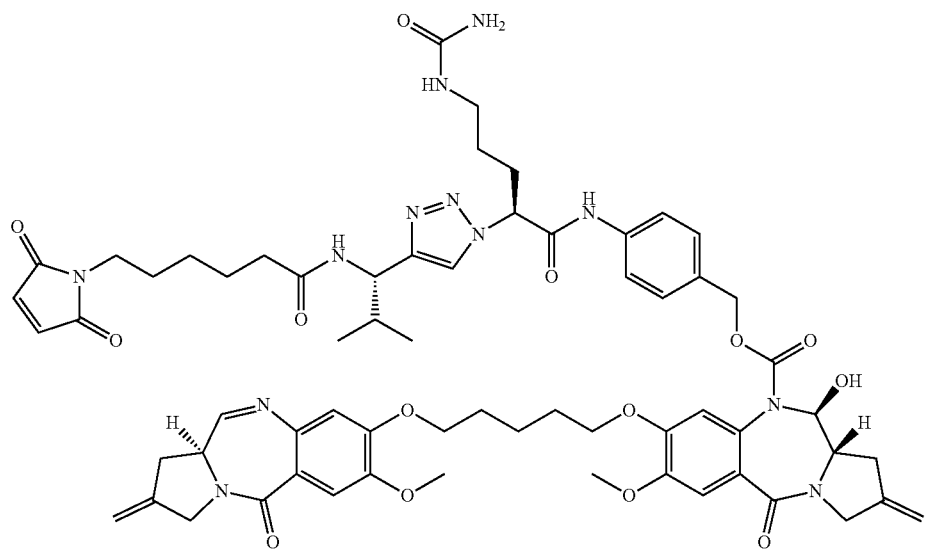

7

Compound 1 is compound 6 of WO 2011/130598

(i) 4-((S)-2-(4-((S)-1-amino-2-methylpropyl)-1H-1,2,3-triazol-1-yl)-5-ureidopentanamido)benzyl (5-((5-(5-(((allyloxy)carbonyl)amino)-4-((R)-2-(acetoxymethyl)-4-methylenepyrrolidine-1-carbonyl)-2-methoxyphenoxy)pentyl)oxy)-2-((R)-2-(acetoxymethyl)-4-methylenepyrrolidine-1-carbonyl)-4-methoxyphenyl)carbamate (3)

Triethylamine (0.55 g, 0.76 mL 5.5 mmol, 2.2 eq.) was added to a stirred solution of the mono-alloc protected bis-aniline 1 (1.98 g, 2.5 mmol, 1.0 eq.) and triphosgene (0.27 g, 0.9 mmol, 0.36 eq.) in dry THF (25 mL) under an argon atmosphere at room temperature. The reaction mixture was heated to 40° C., a sample was treated with methanol and analysed by LCMS as the methyl carbamate.

A solution of benzyl alcohol 2 (1.58 g, 3.24 mmol, 1.3 eq.) in dry THF/DMF (40 mL/5 mL) was added drop-wise to the freshly prepared isocyanate. The reaction mixture was monitored by LCMS and was complete after 4.5 hours at 40° C. The reaction mixture was filtered and the filtrate evaporated under reduced pressure. The residue was purified by flash column chromatography [gradient elution $CHCl_3$/MeOH 3% to 6% in 1% increments] to give the product as a white foam (1.83 g, 56%). Analytical Data: RT 1.72 min; MS (ES$^+$) m/z (relative intensity) 1306 ([M+H]$^{+\cdot}$, 40).

(ii) 4-((S)-2-(4-((S)-1-amino-2-methylpropyl)-1H-1, 2,3-triazol-1-yl)-5-ureidopentanamido)benzyl (5-((5-(5-(((allyloxy)carbonyl)amino)-4-((R)-2-(hydroxymethyl)-4-methylenepyrrolidine-1-carbonyl)-2-methoxyphenoxy)pentyl)oxy)-2-((R)-2-(hydroxymethyl)-4-methylenepyrrolidine-1-carbonyl)-4-methoxyphenyl)carbamate (4)

A solution of $K_2CO_3$ (0.96 g, 7.0 mmol, 5.0 eq.) in $H_2O$ (7 mL) was added to a solution of the acetate 3 (1.82 g, 1.39 mmol, 1.0 eq.) in MeOH (40 mL). The reaction mixture was stirred at room temperature for 1 hour. The methanol was evaporated under reduced pressure, the residue was diluted with $H_2O$ (100 mL) and acidified to pH3 with 1M citric acid. The mixture was extracted with DCM (5×100 mL). The combined extracts were washed with saturated brine (200 mL), dried ($MgSO_4$) and evaporated under reduced pressure to give the product as a white foam (1.51 g, 88%). Analytical Data: RT 1.57 min; MS ($ES^+$) m/z (relative intensity) 1222 ($[M+H]^+$, 45).

(iii) Allyl (11S,11aS)-8-((5-(((11S,11aS)-10-(((4-((S)-2-(4-((S)-1-(((allyloxy)carbonyl)amino)-2-methylpropyl)-1H-1,2,3-triazol-1-yl)-5-ureidopentanamido)benzyl)oxy)carbonyl)-11-hydroxy-7-methoxy-2-methylene-5-oxo-2,3,5,10,11,11a-hexahydro-1H-pyrrolo[2,1-c][1,4]benzodiazepin-8-yl)oxy)pentyl)oxy)-1-hydroxy-7-methoxy-2-methylene-5-oxo-2,3,11,11a-tetrahydro-1H-pyrrolo[2,1-c][1,4]benzodiazepine-10(5H)-carboxylate (5)

Stabilised 45 wt % 2-iodoxybenzoic acid (IBX) (1.78 g, 2.9 mmol, 2.4 eq.) was added in one portion to a solution of the bis-alcohol 4 (1.46 g, 1.19 mmol, 1.0 eq.) in dry DMSO (90 mL). The solution was stirred at 30° C. for 32 hours. The reaction mixture was added to $H_2O$ (500 mL) which was extracted with DCM (5×150 mL). The combined extracts were washed with saturated aqueous sodium bicarbonate solution (300 mL), $H_2O$ (300 mL), brine (300 mL) and dried ($MgSO_4$). The solvent was removed by rotary evaporation under reduced pressure to give the crude product. Purification by flash column chromatography [gradient elution $CHCl_3$/MeOH 0% to 8% in 1% increments] gave the product as a white solid (0.8 g, 55%). Analytical Data: RT 1.52 min; MS ($ES^+$) m/z (relative intensity) 1218 ($[M+H]^+$, 100).

(iv) 4-((S)-2-(4-((S)-1-amino-2-methylpropyl)-1H-12, 3-triazol-1-yl)-5-ureidopentanamido)benzyl (11S,11aS)-1-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]benzodiazepine-10(5H)-carboxylate (6)

$Pd(PPh_3)_4$ (14 mg, 12.4 mol 0.05 eq.) was added to a solution of the bis-alloc compound 5 (0.30 g, 0.25 mmol, 1.0 eq.) and pyrrolidine (39 mg, 45 µL, 0.86 mmol, 2.2 eq.) in dry DCM (20 mL) under an argon atmosphere. The solution was stirred at room temperature for 30 min to give a cloudy suspension. The solvent was evaporated by half under reduced pressure and then diluted with diethyl ether. The precipitated product was collected by filtration, washing with diethyl ether (×2). This afforded the product as a white powder which was used without further purification (0.25 g, 100%). Analytical Data: RT 1.15 min; MS (ES) m/z (relative intensity) 1032 ($[M+H]^+$, 10).

(v) 4-((S)-2-(4-((S)-1-(6-(2,5-dioxo-2,5-dihydro-1H-pyrrol-1-yl)hexanamido)-2-methylpropyl)-1H-1,2,3-triazol-1-yl)-5-ureidopentanamido)benzyl (11S, 11aS)-11-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]benzodiazepine-10 (5H)-carboxylate (7)

EEDQ (12.6 mg, 51 µmol, 1.5 eq.) was added to a solution of amine/imine 6 (35 mg, 34 µmol, 1.0 eq.) and maleimide caproic acid (7.2 mg, 34 mol 1.0 eq.) in dry DCM/MeOH (5 mL/1 mL). The solution was stirred at room temperature for 18 hours. A further portion of EEDQ (12.6 mg, 51 µmol, 1.5 eq.) was added and the reaction was stirred for a further 18 hours. The solvent was evaporated under reduced pressure and the residue was purified by prep HPLC to give the product as a white foam after lyophilisation (5.5 mg, 13%). Analytical Data: RT 1.41 min; MS (ES) m/z (relative intensity) 1225 ($[M+H]^+$, 60).

Example 2

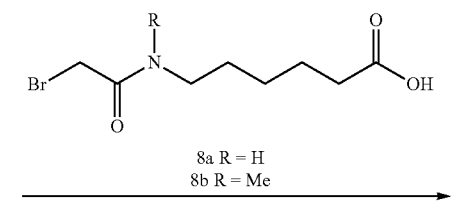

8a R = H
8b R = Me

6

-continued

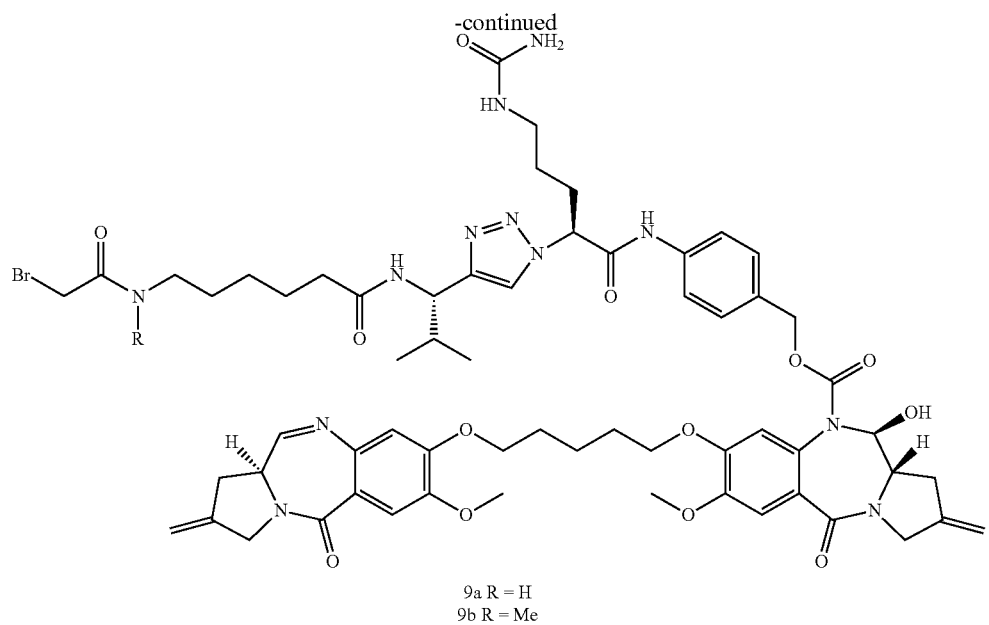

9a R = H
9b R = Me (a) 4-((S)-2-(4-((S)-1-(6-(2-bromoacetamido)hexanamido)-2-methylpropyl)-1H-1,2,3-triazol-1-yl)-5-ureidopentanamido)benzyl (11S,11aS)-11-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]benzodiazepine-10(5H)-carboxylate (9a)

EEDQ (36 mg, 0.15 mmol, 1.5 eq.) was added to a solution of amine/imine 6 (101 mg, 98 µmol, 1.0 eq.) and bromoacetamidocaproic acid 8a (30 mg, 0.12 mmol 1.2 eq.) in dry DCM/MeOH (6 mL/3 mL). The solution was stirred at room temperature for 5 days. The solvent was evaporated under reduced pressure and the residue purified by prep HPLC to give, on lyophilisation, the product as a white foam (25 mg, 20%). Analytical Data: RT 1.42 min; MS (ES+) m/z (relative intensity) 1267 ([M+H]+,20).

(b) 4-((S)-2-(4-((S)-1-(6-(2-bromo-N-methylacetamido)hexanamido)-2-methylpropyl)-1H-1,2,3-triazol-1-yl)-5-ureidopentanamido)benzyl (11S,11aS)-11-hydroxy-7-methoxy-8-((5-(((S)-7-methoxy-2-methylene-5-oxo-2,3, 5,11a-tetrahydro-1H-pyrrolo[2,1-c][1,4]benzodiazepin-8-yl)oxy)pentyl)oxy)-2-methylene-5-oxo-2,3,11,111a-tetrahydro-1H-pyrrolo[2,1-c][1,4]benzodiazepine-10(SH)-carboxylate (9b)

EEDQ (36 mg, 0.15 mmol, 1.5 eq.) was added to a solution of amine/imine 6 (100 mg, 98 µmol, 1.0 eq.) and N methylbromoacetamidocaproic acid 8b (30 mg, 0.12 mmol 1.2 eq.) in dry DCM/MeOH (6 mL/3 mL). The solution was stirred at room temperature for 5 days. The solvent was evaporated under reduced pressure and the residue was purified by prep HPLC to give, on lyophilisation, the product as a white foam (16 mg, 13%). Analytical Data: RT 1.44 min; MS (ES+) m/z (relative intensity) 1280 ([M+H]+., 20).

Example 3

Alternative preparation of [4-[[(2S)-2-[4-[(1S)-1-[6-(2,5-dioxopyrrol-1-yl)hexanoylamino]-2-methylpropyl]triazol-1-yl]-5-ureido-pentanoyl]amino]phenyl]methyl (6S,6aS)-3-[5-[[(6aS)-2-methoxy-8-ox-8-methylene-11-oxo-7,9-dihydro-6aH-pyrrolo[2,1-c][1,4]benzodiazepin-3-yl]oxy]pentoxy]-6-hydroxy-2-methoxy-8-methylene-11-oxo-6,6a,7,9-tetrahydropyrrolo[2,1-c][1,4]benzodiazepine-5-carboxylate (PBD-LD2)

(a) 6-(2, 5-dioxo-2, 5-dihydro-1H-pyrrol-1-yl)-N—((S)-1-(1-((S)-1-((4-(hydroxymethyl)phenyl)amino)-1-oxo-5-ureidopentan-2-yl)-1H-1,2,3-triazol-4-yl)-2-methylpropyl)hexanamide (12)

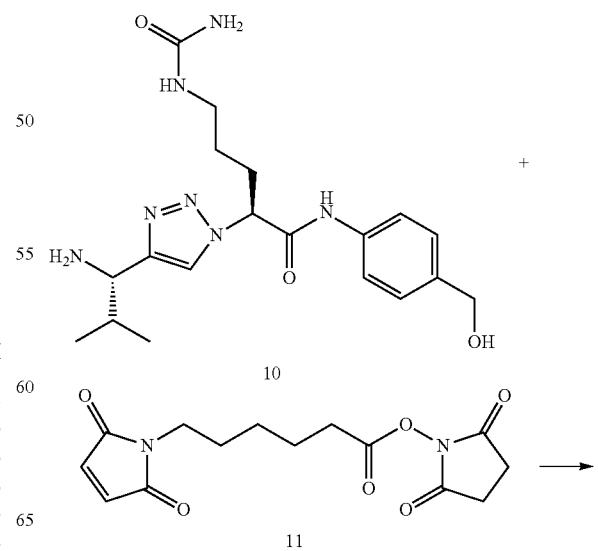

-continued

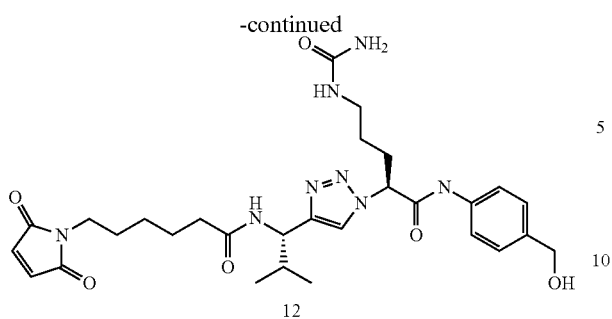
12

Amine 10 (4.37 g, 10.8 mmol, 1.0 eq) and 2,5-dioxopyrrolidin-1-yl 6-(2,5-dioxo-2,5-dihydro-1H-pyrrol-1-yl) hexanoate 11 (3.67 g, 11.9 mmol, 1.1 eq) were dissolved in anhydrous DMF (100 mL) with stirring. The reaction mixture was stirred at room temperature for 2 hours. The solvent was evaporated under reduced pressure to give the product 12 as a viscous yellow oil (6.0 g, 92%). Analytical Data: RT 1.20 min; MS (ES) m/z (relative intensity) 597 ([M+H]$^{+\cdot}$, 100).

(b) [4-[[(2S)-2-[4-[(JS)-1-[6-(2,5-dioxopyrrol-1-yl) hexanoylamino]-2-methyl-propyl]triazol-1-yl]-5-ureido-pentanoyl]amino]phenyl]methyl (6S,6aS)-3-[5-[[(6aS)-2-methoxy-8-methylene-11-oxo-7,9-dihydro-6aH-pyrrolo[2,1-c][1,4]benzodiazepin-3-yl]oxy]pentoxy]-6-hydroxy-2-methoxy-8-methylene-11-oxo-6,6a, 7,9-tetrahydropyrrolo[2,1-c][1,4]benzodiazepine-5-carboxylate (7, PBD-LD2)

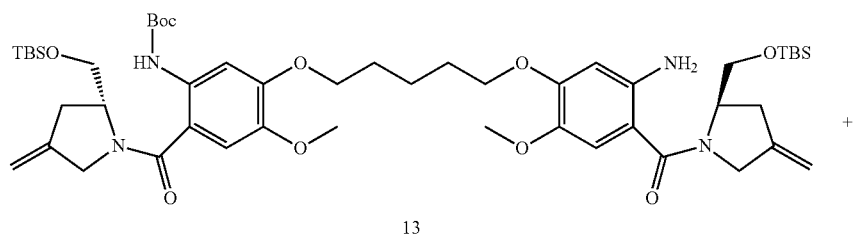
13

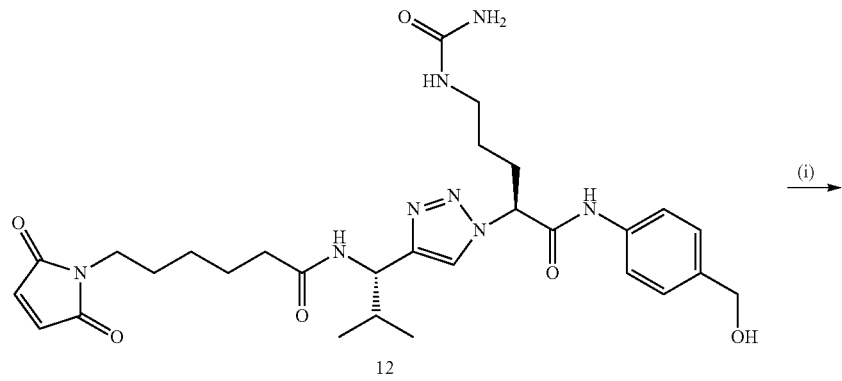
12

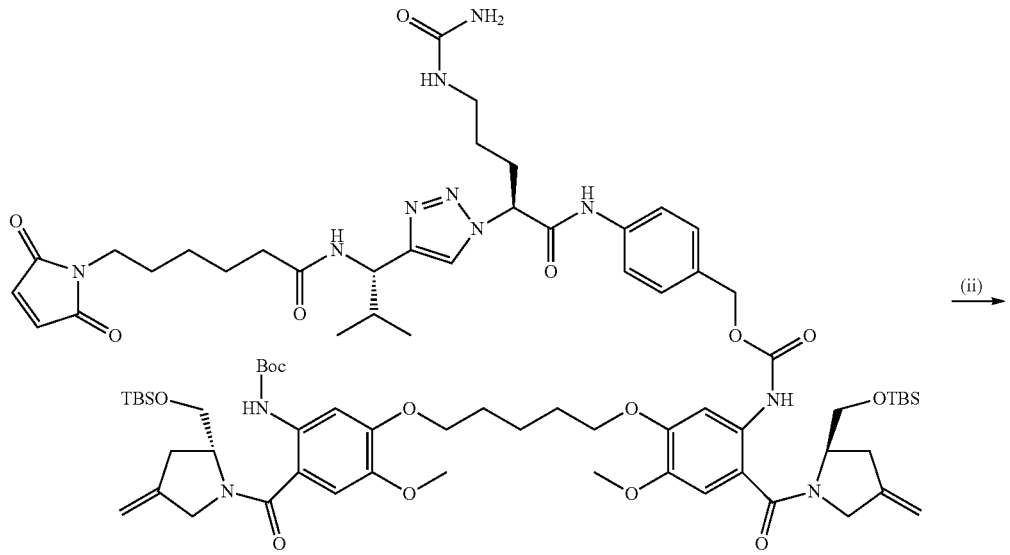
14

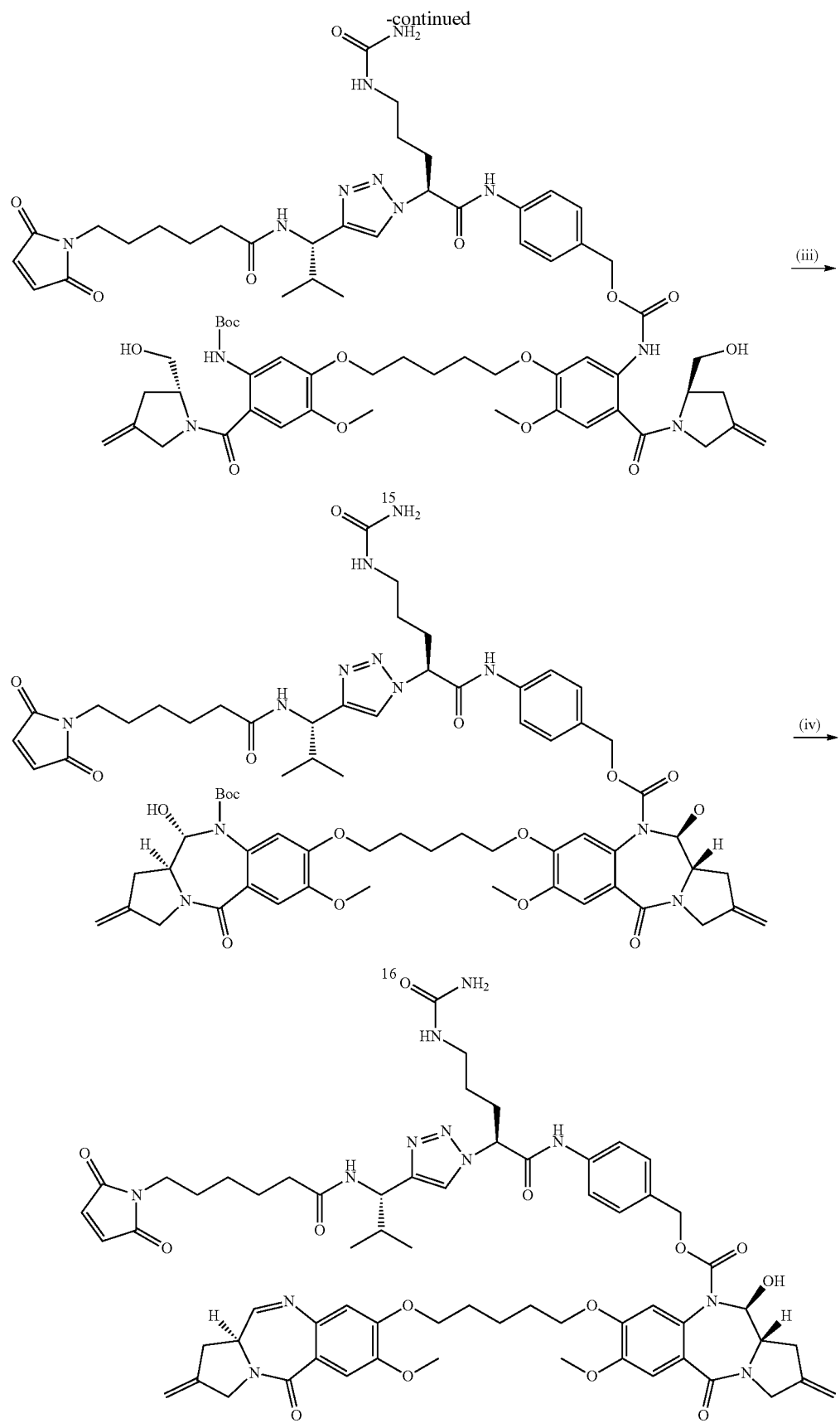

Summary
(i) triphosgene, pyridine, THF
(ii) AcOH, THF, H$_2$O
(iii) IBX, DMSO
(iv) 95% TFA Compound 13 is Compound 9 of WO 2013/055987.

(i) 4-((S)-2-(4-((S)-1-(6-(2,5-dioxo-2,5-dihydro-1H-pyrrol-1-yl)hexanamido)-2-methylpropyl)-1H-1,2,3-triazol-1-yl)-5-ureidopentanamido)benzyl (5-((5-(5-((tert-butoxycarbonyl)amino)-4-((R)-2-(((tert-butyldimethylsilyl)oxy)methyl)-4-methylenepyrrolidine-1-carbonyl)-2-methoxyphenoxy)pentyl)oxy)-2-((R)-2-(((tert-butyldimethylsilyl)oxy)methyl)-4-methylenepyrrolidine-1-carbonyl)-4-methoxyphenyl) carbamate (14)

Triethylamine (0.13 g, 0.18 mL 1.3 mmol, 2.2 eq.) was added to a stirred solution of the mono-boc protected bis-aniline 13 (0.555 g, 0.58 mmol, 1.0 eq.) and triphosgene (0.062 g, 0.21 mmol, 0.36 eq.) in dry THF (15 mL) under an argon atmosphere at room temperature. The reaction mixture was heated to 40° C., a sample was treated with methanol and analysed by LCMS as the methyl carbamate.

A solution of benzyl alcohol 12 (0.51 g, 0.85 mmol, 1.45 eq.) in dry THF/pyridine (3 mL/3 mL) was added drop-wise to the freshly prepared isocyanate. The reaction mixture was monitored by LCMS and was complete after 4 hours at 40° C. The reaction mixture was filtered and the filtrate evaporated under reduced pressure. The residue was taken up in CHCl$_3$ (100 mL) and this was washed with saturated CuSO$_4$ solution (2×150 mL), saturated brine (150 mL), dried (MgSO$_4$) and evaporated under reduced pressure to give a yellow foam. Purification by flash column chromatography [gradient elution CHCl$_3$/2% MeOH to 5% MeOH in 1% increments] gave the product as a white foam (0.26 g, 29%). Analytical Data: RT 2.23 min; MS (ES$^+$) m/z (relative intensity) 1577 ([M+H]$^+$, 100).

(ii) 4-((S)-2-(4-((S)-1-(6-(2, 5-dioxo-2, 5-dihydro-1H-pyrrol-1-yl)hexanamido)-2-methylpropyl)-1H-1,2,3-triazol-1-yl)-5-ureidopentanamido)benzyl (5-((5-(5-(((tert-butoxycarbonyl)amino)-4-((R)-2-(hydroxymethyl)-4-methylenepyrrolidine-1-carbonyl)-2-methoxyphenoxy)pentyl)oxy)-2-((R)-2-(hydroxymethyl)-4-methylenepyrrolidine-1-carbonyl)-4-methoxyphenyl)carbamate (15)

AcOH/H$_2$O (1.5/1) (42 mL) was added to a solution of compound 14 (0.934 g, 0.6 mmol, 1.0 eq) in THF (17 mL) and the resultant solution was stirred at room temperature for 72 hours. The reaction mixture was basified to pH8 with saturated sodium hydrogen carbonate solution. The mixture was extracted with DCM (4×100 mL) and the combined extracts were washed with saturated sodium hydrogen carbonate solution (300 mL), H$_2$O (200 mL), saturated brine (250 mL), dried (MgSO$_4$) and evaporated under reduced pressure. Purification of the residue by flash column chromatography [gradient elution CHCl$_3$/MeOH 2% to 9% in 1% increments] gave the product as a white foam (0.573 g, 72%). Analytical Data: RT 1.6 min; MS (ES$^+$) m/z (relative intensity) 1347 ([M+H]$^+$, 100).

(iii) tert-butyl (11S,11aS)-8-((5-(((11,11aS)-10-(((4-((S)-2-(4-((S)-1-(6-(2, 5-dioxo-2, 5-dihydro-1H-pyrrol-1-yl)hexanamido)-2-methylpropyl)-1H-1,2,3-triazol-1-yl)-5-ureidopentanamido)benzyl)oxy)carbonyl)-11-hydroxy-7-methoxy-2-methylene-5-oxo-2,3,5,10,11,11a-hexahydro-1H-pyrrolo[2,1-c][1,4]benzodiazepin-8-yl)oxy)pentyl)oxy)-1-hydroxy-7-methoxy-2-methylene-5-oxo-2,3,11,11a-tetrahydro-1H-pyrrolo[2,1-c][1,4]benzodiazepine-10(5H)-carboxylate (16)

Stabilised 45 wt % 2-iodoxybenzoic acid (IBX) (0.635 g, 1.02 mmol, 2.4 eq.) was added in one portion to a solution of the bis alcohol (15) (0.573 g, 0.425 mmol, 1.0 eq.) in dry DMSO (30 mL). The solution was stirred at 30° C. for 21 hours. A further portion of IBX (26 mg, 42.5 mol, 0.1 eq) was added and the reaction was continued for a further 24 h. The reaction mixture was added to brine solution (500 mL) which was extracted with DCM (5×100 mL). The combined extracts were washed with saturated aqueous sodium bicarbonate solution (300 mL), H$_2$O (200 mL), brine (300 mL) and dried (MgSO$_4$). The solvent was removed by rotary evaporation under reduced pressure to give the crude product. Purification by flash column chromatography [gradient elution CHCl$_3$/MeOH 0% to 6% in 1% increments] gave the product as a white solid (0.35 g, 61%). Analytical Data: RT 1.53 min; MS (ES) m/z (relative intensity) 1343 ([M+H]$^-$, 97).

(iv) 4-((S)-2-(4-((S)-1-(6-(2, 5-dioxo-2, 5-dihydro-1H-pyrrol-1-yl)hexanamido)-2-methylpropyl)-1H-1,2,3-triazol-1-yl)-5-ureidopentanamido)benzyl (11S,11aS)-11-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]benzodiazepine-10(5H)-carboxylate (7)

A cold (ice bath) solution of 95% trifluoroacetic acid (16 mL) was added to compound 16 which had been cooled in an ice bath. The solution was stirred at 0° C. for 15 minutes when it was shown to be complete by LCMS. The reaction mixture was added dropwise to a mixture of ice and saturated sodium hydrogen carbonate solution to neutralize the trifluoroacetic acid solution. The mixture was extracted with 10% MeOH/CHCl$_3$ (4×100 mL) and the combined extracts were washed with saturated brine (200 mL), dried (MgSO$_4$) and evaporated under reduced pressure to give the product as a yellow solid (0.337 g, 106%). Analytical Data: RT 1.45 min; MS (ES$^+$) m/z (relative intensity) 1225 ([M+H]$^+$, 100).

Example 4

Preparation of [4-[[(2S)-2-[[1-[5-(2,5-dioxopyrrol-1-yl)pentylcarbamoyl]cyclobutanecarbonyl]amino]-5-ureido-pentanoyl]amino]phenyl]methyl (6S,6aS)-3-[5-[[(6aS)-2-methoxy-8-methylene-11-oxo-7,9-dihydro-6aH-pyrrolo[2,1-c][1,4]benzodiazepin-3-yl]oxy]pentoxy]-6-hydroxy-2-methoxy-8-methylene-1-oxo-6,6a,7,9-tetrahydropyrrolo[2,1-c][1,4]benzodiazepine-5-carboxylate (24, PBD-LD3)

(a) Allyl (5-((5-(5-amino-4-((S)-2-(((tert-butyldimethylsilyl)oxy)methyl)-4-methylenepyrrolidine-1-carbonyl)-2-methoxyphenoxy)pentyl)oxy)-2-((S)-2-(((tert-butyldimethylsilyl)oxy)methyl)-4-methylenepyrrolidine-1-carbonyl)-4-methoxyphenyl) carbamate (17)

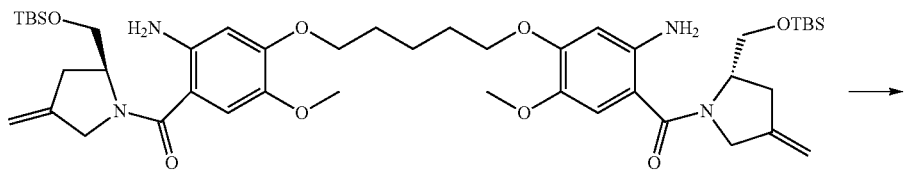

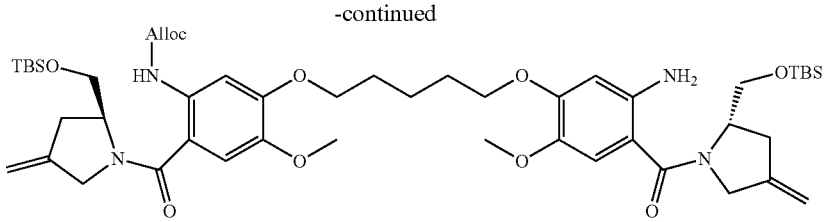

17

Compound 17A is Compound 8 of WO 2013/055987.

A solution of allyl chloroformate 17A (0.38 g, 0.34 mL, 3.2 mmol, 1.0 eq.) in dry DCM (10 mL) was added dropwise to a solution of the bis-aniline (2.72 g, 3.2 mmol, 1.0 eq.) and dry pyridine (0.5 g, 0.52 mL, 6.4 mmol, 2.0 eq.) in dry DCM (30 mL) at −78° C. (dry ice/acetone) under an argon atmosphere. The resultant solution was stirred at −78° C. for 1 hour then allowed to reach room temperature. The reaction mixture was diluted with DCM (50 mL) and washed with saturated copper sulphate solution (2×200 mL), water (200 mL), brine (200 mL), dried (MgSO$_4$) and evaporated under reduced pressure. Purification by flash column chromatography [gradient elution 60% n-hexane/40% EtOAc to 100% EtOAc in 10% increments] gave the product as an off white foam (1.45 g, 48%). Analytical Data: RT 2.25 min; MS (ES$^+$) m/z (relative intensity) 937 ([M+H]$^{+\cdot}$, 100), 959([M+Na]$^{+\cdot}$, 60).

(b) [4-[[(2S)-2-[[1-[5-(2, 5-dioxopyrrol-1-yl)pentylcarbamoyl]cyclobutanecarbonyl]amino]-5-ureidopentanoyl]amino]phenyl]methyl (6S,6aS)-3-[5-[[(6aS)-2-methoxy-8-methylene-11-oxo-7,9-dihydro-6aH-pyrrolo[2,1-c][1,4]benzodiazepin-3-yl]oxy]pentoxy]-6-hydroxy-2-methoxy-8-methylene-11-oxo-6,6a,7,9-tetrahydropyrrolo[2,1-c][1,4]benzodiazepine-5-carboxylate (24)

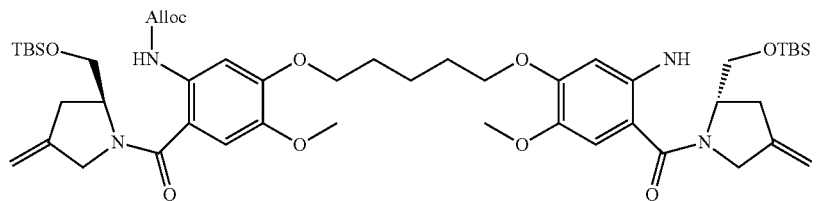

17

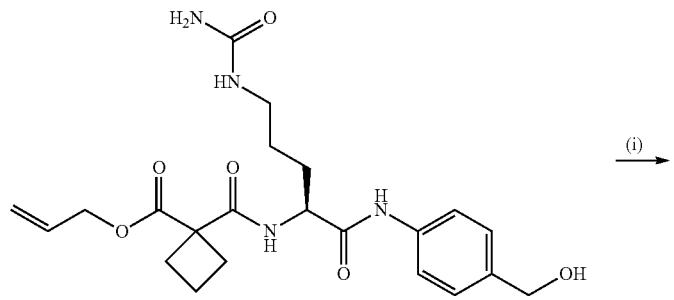

18

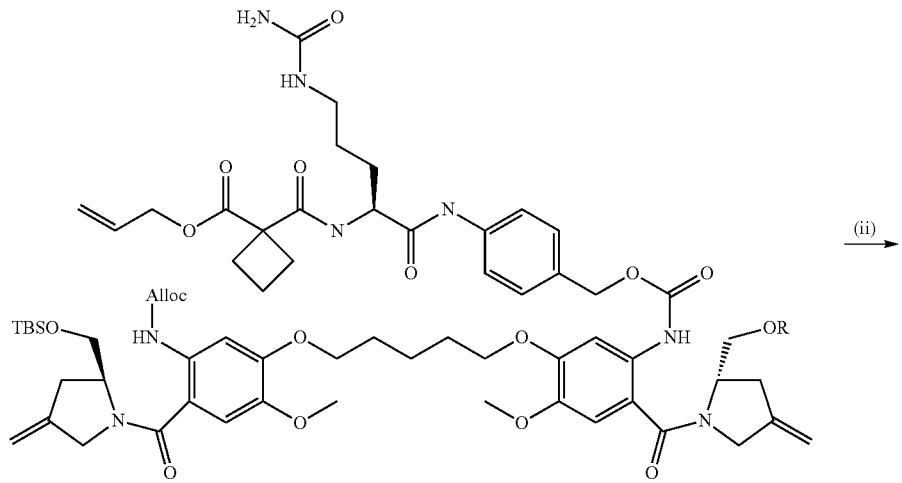

19

-continued
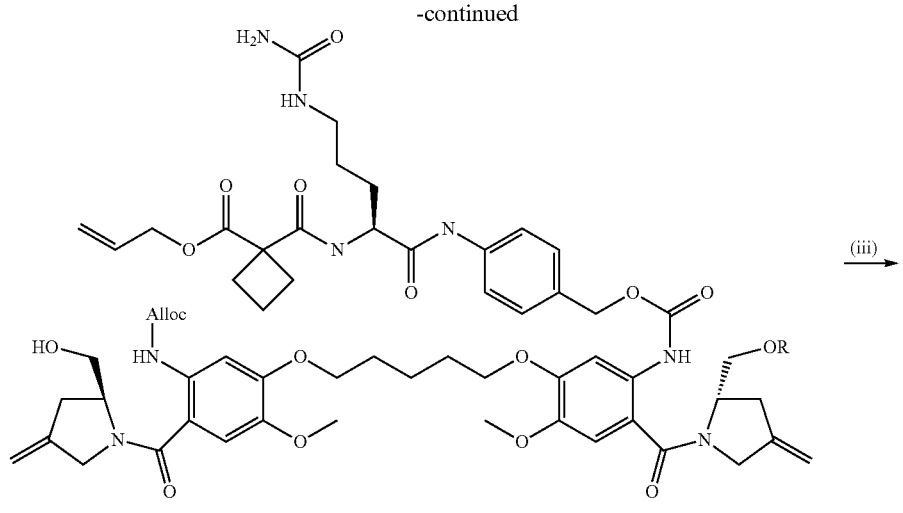
20
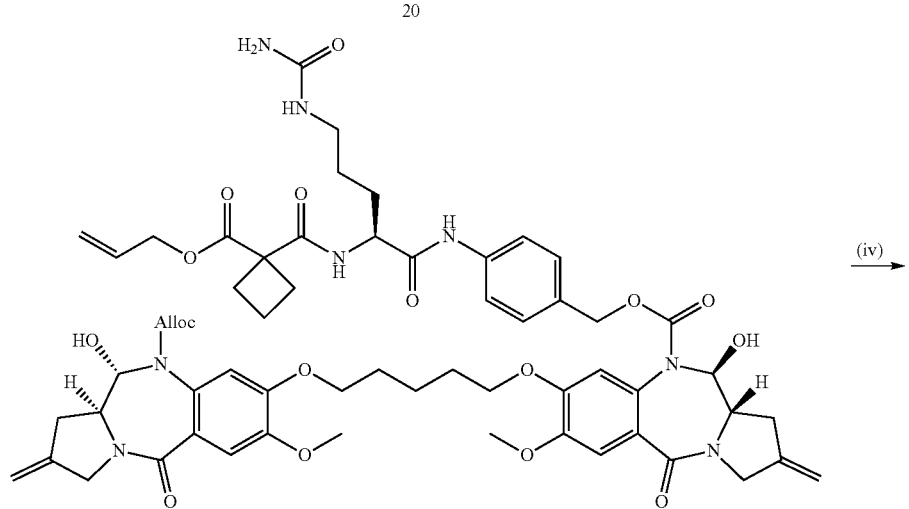
21
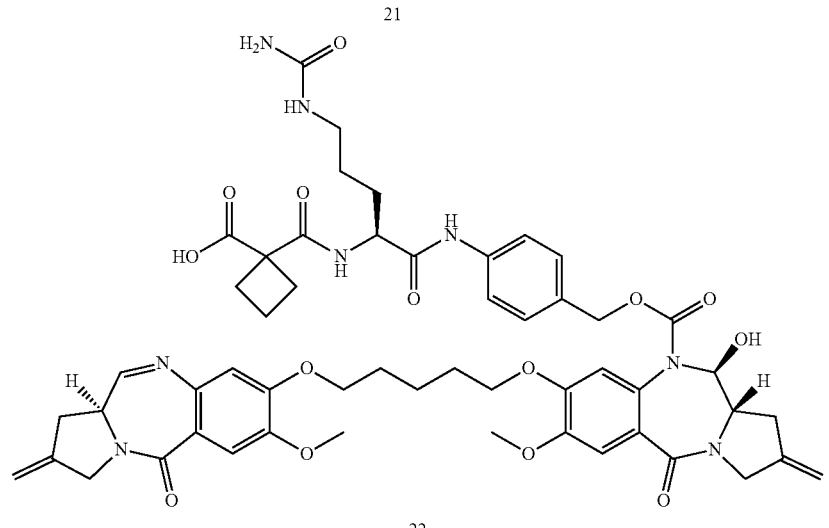
22
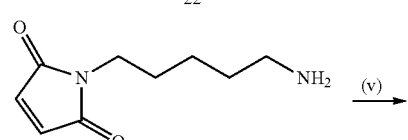
23

-continued

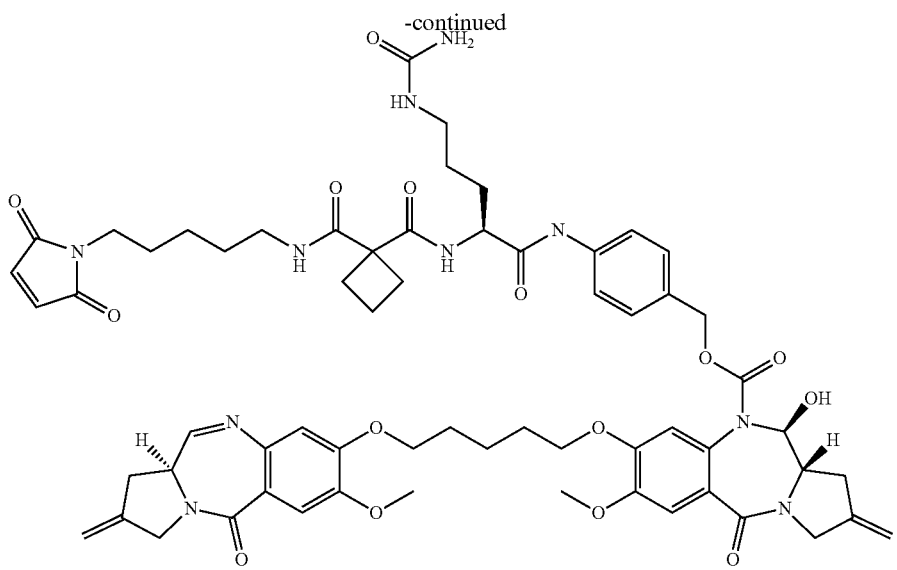

24

Summary
(i) triphosgene, pyridine, THF
(ii) TBAF, THF
(iii) IBX, DMSO
(iv) Pd(PPh$_3$)$_4$, pyrrolidine, CH$_2$Cl$_2$
(v) BOP-Cp, DIEA, DMF (i) Allyl 1-(((S)-1-((4-(((((5-((5-(5-(((allyloxy)carbonyl)amino)-4-((S)-2-(((tert-butyldimethylsilyl)oxy)methyl)-4-methylenepyrrolidine-1-carbonyl)-2-methoxyphenoxy)pentyl)oxy)-2-((S)-2-(((tert-butyldimethylsilyl)oxy)methyl)-4-methylenepyrrolidine-1-carbonyl)-4-methoxyphenyl)carbamoyl)oxy)methyl)phenyl)amino)-1-oxo-5-ureidopentan-2-yl)carbamoyl)cyclobutane-1-carboxylate (19)

Triethylamine (1.85 g, 0.26 mL 1.85 mmol, 2.2 eq.) was added to a stirred solution of the mono-alloc protected bis-aniline 17 (0.79 g, 0.84 mmol, 1.0 eq.) and triphosgene (90 mg, 0.3 mmol, 0.36 eq.) in dry THF (20 mL) under an argon atmosphere at room temperature. The reaction mixture was heated to 40° C., a sample was treated with methanol and analysed by LCMS as the methyl carbamate.

A solution of benzyl alcohol 18 (0.49 g, 1.1 mmol, 1.3 eq.) in dry THF (20 mL) was added drop-wise to the freshly prepared isocyanate. The reaction mixture was monitored by LCMS and was complete after 5 hours at 40° C. The reaction mixture was filtered and the filtrate evaporated under reduced pressure. Purification by flash column chromatography [gradient elution EtOAc/0% MeOH to 6% MeOH in 1% increments] gave the product as a white foam (0.73 g, 61%). Analytical Data: RT 2.20 min; MS (ES) m/z (relative intensity) 1410 ([M+H]$^-$, 50), 1431 ([M+Na]$^+$, 50).

(ii) Allyl 1-(((S)-1-((4-(((((5-((5-(5-(((allyloxy)carbonyl)amino)-4-((S)-2-(hydroxymethyl)-4-methylenepyrrolidine-1-carbonyl)-2-methoxyphenoxy)pentyl)oxy)-2-((S)-2-(hydroxymethyl)-4-methylenepyrrolidine-1-carbonyl)-4-methoxyphenyl)carbamoyl)oxy)methyl)phenyl)amino)-1-oxo-5-ureidopentan-2-yl)carbamoyl)cyclobutane-1-carboxylate (20)

Tetra-N-butylammonium fluoride (1.0 M in THF, 1.1 mL, 2.2 eq) was added to a solution of bis-TBS compound 19 (0.7 g, 0.5 mmol, 1.0 eq) in dry THF (20 mL) under an argon atmosphere. The reaction mixture was stirred at room temperature for 15 min. The solvent was evaporated under reduced pressure and the residue re-dissolved in DCM, washed with brine (×1), dried (MgSO$_4$) and evaporated to give a pale yellow oil. Purification by flash column chromatography [gradient elution EtOAc/MeOH 5% to 15% in 2.5% increments] gave the product as a white foam (0.46 g, 79%). Analytical Data: RT 1.55 min; MS (ES$^+$) m/z (relative intensity) 1181 ([M+H]$^+$, 100).

(iii) Allyl (11S,11aS)-8-((5-(((11S,11aS)-10-(((4-((S)-2-(1-((allyloxy)carbonyl)cyclobutane-1-carboxamido)-5-ureidopentanamido)benzyl)oxy)carbonyl)-11-hydroxy-7-methoxy-2-methylene-5-oxo-2,3,5,10,11,11a-hexahydro-1H-pyrrolo[2,1-c][1,4]benzodiazepin-8-yl)oxy)pentyl)oxy)-1-hydroxy-7-methoxy-2-methylene-5-oxo-2,3,11,11a-tetrahydro-1H-pyrrolo[2,1-c][1,4]benzodiazepine-10(5H)-carboxylate (21)

Stabilised 45 wt % 2-iodoxybenzoic acid (IBX) (0.545 g, 0.88 mmol, 2.4 eq.) was added in one portion to a solution of the bis alcohol 20 (0.43 g, 0.365 mmol, 1.0 eq.) in dry DMSO (31 mL). The solution was stirred at 30° C. for 18 hours. The reaction mixture was added to brine solution which was extracted with DCM (5×75 mL). The combined extracts were washed with saturated aqueous sodium bicarbonate solution (200 mL), water (200 mL), brine (200 mL) and dried (MgSO$_4$). The solvent was removed by rotary evaporation under reduced pressure to give the crude product. Purification by flash column chromatography [gradient elution CHCl$_3$/MeOH 0% to 6% in 1% increments] gave the product as a white foam (0.21 g, 48%). Analytical Data: RT 1.48 min; MS (ES$^+$) m/z (relative intensity) 1177 ([M+H]$^+$, 100).

(iv) 1-(((S)-1-((4-((((11S,11aS)-1-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,5,10,11,11a-hexahydro-1H-pyrrolo[2,1-c][,4]benzodiazepine-10-carbonyl)oxy)methyl)phenyl)amino)-1-oxo-5-ureidopentan-2-yl)carbamoyl)cyclobutane-1-carboxylic acid (22)

Pd(PPh$_3$)$_4$ (6 mg, 5.1 µmol 0.06 eq.) was added to a solution of compound 21 (0.1 g, 85 µmol, 1.0 eq.) and pyrrolidine (15 mg, 17 µL, 0.21 mmol, 2.5 eq.) in dry DCM (5 mL) under an argon atmosphere. The solution was stirred at room temperature for 35 minutes. The reaction mixture was diluted with diethyl ether (xs) to precipitate the product which was collected by filtration, washing with diethyl ether (x2). This afforded the product as a white powder which was used without further purification. Analytical Data: RT 1.34 min; MS (ES$^+$) m/z (relative intensity) 1035 ([M+H]$^+$, 100).

(v) 4-((S)-2-(1-((5-(2,5-dioxo-2,5-dihydro-1H-pyrrol-1-yl)pentyl)carbamoyl)cyclobutane-1-carboxamido)-5-ureidopentanamido)benzyl (11S,11aS)-11-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]benzodiazepine-10(5H)-carboxylate (24)

N,N-Diisopropylethylamine (15 mg, 20 µL, 116 µmol, 3.0 eq) was added to a solution of bis(2-oxo-3-oxazolidinyl)phosphinic chloride (12 mg, 46.4 µmol, 1.2 eq) and acid 22 (40 mg, 39.1 µmol, 1.0 eq) in dry DMF (5 mL) under an argon atmosphere with stirring. 5-(2,5-Dioxo-2,5-dihydro-1H-pyrrol-1-yl)pentan-1-aminium chloride 23 (9 mg, 39.1 mol, 1.0 eq) was added and the mixture was stirred overnight at room temperature. The mixture was quenched with citric acid and extracted with DCM (3×50 mL). The combined extracts were washed with saturated brine (100 mL), dried (MgSO$_4$) and evaporated under reduced pressure to give a yellow solid. Purified by prep HPLC to give the product as a white foam on lyophilisation (4.5 mg, 10%). Analytical Data: RT 1.42 min; MS (ES$^+$) m/z (relative intensity) 1199 ([M+H]$^+$, 60).

Method of Preparing ADCs

Preparation of Cysteine Engineered Antibodies for Conjugation by Reduction and Reoxidation Under certain conditions, the cysteine engineered antibodies may be made reactive for conjugation with linker-drug intermediates of the invention, such as those in Table 4, by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Full length, cysteine engineered monoclonal antibodies (ThioMabs) expressed in CHO cells (Gomez et al (2010) Biotechnology and Bioeng. 105(4):748-760; Gomez et al (2010) Biotechnol. Prog. 26:1438-1445) were reduced, for example with about a 50 fold excess of DTT overnight at room temperature to reduce disulfide bonds which may form between the newly introduced cysteine residues and the cysteine present in the culture media.

Light chain amino acids are numbered according to Kabat (Kabat et al., *Sequences of proteins of immunological interest*, (1991) 5th Ed., US Dept of Health and Human Service, National Institutes of Health, Bethesda, Md.). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (ThioMabs) expressed in CHO cells bear cysteine adducts (cystines) or glutathionylated on the engineered cysteines due to cell culture conditions. To liberate the reactive thiol groups of the engineered cysteines, the ThioMabs are dissolved in 500 mM sodium borate and 500 mM sodium chloride at about pH 8.0 and reduced with about a 50-100 fold excess of 1 mM TCEP (tris(2-carboxyethyl)phosphine hydrochloride (Getz et al (1999) Anal. Biochem. Vol 273: 73-80; Soltec Ventures, Beverly, Mass.) for about 1-2 hrs at 37° C. Alternatively, DTT can be used as reducing agent. The formation of inter-chain disulfide bonds was monitored either by non-reducing SDS-PAGE or by denaturing reverse phase HPLC PLRP column chromatography. The reduced ThioMab is diluted and loaded onto a HiTrap SP FF column in 10 mM sodium acetate, pH 5, and eluted with PBS containing 0.3M sodium chloride, or 50 mM Tris-C1, pH 7.5 containing 150 mM sodium chloride.

Disulfide bonds were reestablished between cysteine residues present in the parent Mab by carrying out reoxidation. The eluted reduced ThioMab is treated with 15× or 2 mM dehydroascorbic acid (dhAA) at pH 7 for 3 hours or for 3 hrs in 50 mM Tris-C1, pH 7.5, or with 2 mM aqueous copper sulfate (CuSO$_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Liquid chromatography/Mass Spectrometric Analysis was performed on a TSQ Quantum Triple Quadrupole™ mass spectrometer with extended mass range (Thermo Electron, San Jose Calif.). Samples were chromatographed on a PRLP-S®, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluent was directly ionized using the electrospray source. Data were collected by the Xcalibur® data system and deconvolution was performed using ProMass® (Novatia, LLC, New Jersey). Prior to LC/MS analysis, antibodies or drug conjugates (50 micrograms) were treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 micron particle size, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody. Cysteine engineered antibodies of the present invention can be prepared according the general method described above.

Conjugation of Linker-drug Intermediates to Antibodies (Procedure 1)

Engineered antibody cysteines were blocked as mixed disulfides with glutathione and/or cysteine as expressed in CHO cells. These cysteines had to be "deblocked" prior to conjugation.

Deblocked antibody (5-12 mg/mL) in 20 mM succinate, 150 mM NaCl, 2 mM EDTA was brought to 75-100 mM Tris, pH 7.5-8 (using 1M Tris). Co-solvent (DMSO, DMF, or DMA) was added to the antibody solution, followed by linker-drug (in DMSO or DMF) to give a final %-organic solvent of 10-13% and final concentration of linker-drug 2.5-10× relative to antibody concentration. Reactions were allowed to proceed at room temperature for 1-12 hours (until maximum conjugation was achieved). Conjugation reactions were purified via cation exchange chromatography and/or gel filtration using disposable columns (S maxi or Zeba, respectively). Additional purification by preparative gel filtration (S200 columns) was performed if the crude conjugate was significantly aggregated according to analytical SEC (e.g., >10%). Conjugates were subsequently exchanged into formulation buffer (20 mM His-acetate, pH 5.5, 240 mM sucrose) using either gel filtration or dialysis. Tween-20 was subsequently added to the purified conjugate to reach a final concentration of 0.02%. Final conjugate concentrations ranged from 2.4 to 7.5 mg/mL (% Yield: 34-81% from deblocked antibody). Conjugates were analyzed by LCMS to obtain a measurement of the drug-antibody ratio (DAR), which ranged from 1.3 to 2.1 (average: 1.8). Conjugates were also analyzed for presence of high-molecular weight aggregates using analytical SEC (Zenix or Shodex columns); final, purified conjugates displayed aggregation ranging from 0-10%. Conjugates were also assessed for endotoxin contamination, which, in all cases, did not exceed 1.3 EU/mg. Free, unconjugated drug did not exceed 1% of the final conjugate.

Conjugation of Linker-drug Intermediates to Antibodies (Procedure 2, Alternative Procedure)

After the reduction and reoxidation procedures of the above example, the antibody is dissolved in PBS (phosphate buffered saline) buffer and chilled on ice. An excess, from about 1.5 molar to 20 equivalents of a linker-drug intermediate with a thiol-reactive functional group such as maleimido or bromo-acetamide, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The conjugation mixture may be loaded and eluted through a HiTrap SP FF column to remove excess drug-linker intermediate and other impurities. The reaction mixture is concentrated by centrifugal ultrafiltration and the cysteine engineered antibody drug conjugate is purified and desalted by elution through G25 resin in PBS, filtered through 0.2 μm filters under sterile conditions, and frozen for storage.

The ADCs of the present invention can be prepared according to the procedure described in the above section.

Assays

Select linkers were then tested and found active in in vitro and in vivo assays. The cleavage data is shown in the table below Cathepsin B Cleavage Assay Like peptide linkers, non-peptide linkers for ADC is expect to be cleavable in lysosome in order for proper drug release. As a digestive organelle of the cell, lysosome is enriched with some proteases which show optimal hydrolytic activity at an acidic pH. Cathepsin B is a representative lysosomal protease and has been shown to contribute to the activation of ADC peptide linkers (ref). As an initial screen, an assay was developed using purified cathepsin B to identify cleavable linker-drug constructs that are suitable for conjugation with antibody. Norfloxacin was used to represent the drug component of the linker-drug. The percentage of cleavage relative to the control peptides (such as Val-Cit) was measured at a given time point as well as the kinetic parameters of the cleavage reaction (Km and Vmax). Detailed description of the assay is shown below. From this assay, a variety of proteolytically active and structurally diverse linkers were identified and later used in making ADCs.

Cathepsin B cleavage activity using experimental linker-drugs as substrate was measured by monitoring the release of Norfloxacin using LC/MS. Varying concentrations of linker-drug (3-fold serial dilutions) were incubated in 20 uL reactions containing 20 nM Cathepsin B (EMD Millipore cat. #219364, human liver), 10 mM MES pH 6.0, 1 mM DTT, 0.03% CHAPS, and 25 nM Norfloxacin-d5 internal standard (Santa Cruz Biotechnology, cat. #sc-301482). Reactions were incubated for 1 hour at 37° C., followed by addition of 60 uL of 2% formic acid to quench the reactions. Samples were analyzed by injecting 2 uL of stopped reactions on a Waters Acquity UPLC BEH Phenyl column (2.1 mm×50 mm, Waters cat. #186002884). Samples were purified using a linear 2 minute gradient (0% to 80%) of acetonitrile, 0.1% formic acid on a Water Acquity UPLC. Norfloxacin and Norfloxacin-d5 internal standard were detected using an AB Sciex QTrap 5500 triple quadrupole mass spectrometer operating in positive MRM mode (Norfloxacin 320→233 m/z, Norfloxacin-d5 325→233 m/z). The quantified norfloxacin (normalized with internal standard) was plotted against linker-drug concentration, and the resulting plot was curve fitted with a Michaelis-Menten fit using GraphPad Prism software for the kinetic constants Km and Vmax.

In Vitro Cell Proliferation Assay

Efficacy of ADC was measured by a cell proliferation assay employing the following protocol (CELLTITER GLO™ Luminescent Cell Viability Assay, Promega Corp. Technical Bulletin TB288; Mendoza et al (2002) Cancer Res. 62:5485-5488):

1. An aliquot of 100 μl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CELLTITER GLO™ Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Data are plotted as the mean of luminescence for each set of replicates, with standard deviation error bars. The protocol is a modification of the CELLTITER GLO™ Luminescent Cell Media: SK-BR-3 grow in 50150/10% FBS/glutamine/250 μg/mL G-418 OVCAR-3 grow in RPMI/20% FBS/glutamine In Vivo Assay 1. The efficacy of the anti-CD33 antibody-drug conjugates (ADCs) was investigated in a mouse xenograft model of HL-60 or EOL-1 (human acute myeloid leukemia). The HL-60 cell line was obtained from ATCC (American Type Culture Collection; Manassas, Va.) and EOL-1 cell line was originated from DSMZ (German Collection of Microorganisms and Cell Cultures; Braunschweig, Germany).

Female C.B-17 SCID mice (Charles River Laboratories; Hollister, Calif.) were each inoculated subcutaneously in the flank area with five million cells of HL-60 or EOL-1. When the xenograft tumors reached an average tumor volume of 100-300 mm3 (referred to as Day 0), animals were randomized into groups of 7-10 mice each and received a single intravenous injection of the ADCs. Approximately 4 hours prior to administration of ADCs, animals were dosed intraperitoneally with excess amount (30 mg/kg) of anti-gD control antibody to block possible nonspecific antibody binding sites on the tumor cells. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration.

2. The efficacy of the anti-Napi2B antibody-drug conjugates (ADCs) was investigated in a mouse xenograft model of OVCAR3-X2.1 (human ovarian cancer). The OVCAR3 cell line was obtained from ATCC (American Type Culture Collection; Manassas, Va.) and a sub-line OVCAR3-X2.1 was generated at Genentech for optimal growth in mice.

Female C.B-17 SCID-beige mice (Charles River Laboratories; San Diego, Calif.) were each inoculated in the thoracic mammary fat pad area with ten million OVCAR3-X2.1 cells. When the xenograft tumors reached an average tumor volume of 100-300 mm3 (referred to as Day 0), animals were randomized into groups of 7-10 mice each and received a single intravenous injection of the ADCs. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration.

3. The efficacy of the anti-CD22 antibody-drug conjugates (ADCs) is investigated in a mouse xenograft model of BJAB-luc (human Burkitt's lymphoma) or WSU-DLCL2 (human diffuse large B-cell lymphoma). The BJAB cell line is obtained from DSMZ (German Collection of Microorganisms and Cell Cultures; Braunschweig, Germany), and a sub-line BJAB-luc is generated at Genentech to stably express the luciferase gene. The WSU-DLCL2 cell line is also originated from DSMZ.

Female C.B-17 SCID mice (Charles River Laboratories; Hollister, Calif.) are each inoculated subcutaneously in the flank area with 20 million cells of BJAB-luc or WSU-DLCL2. When the xenograft tumors reached an average tumor volume of 100-300 mm3 (referred to as Day 0), animals are randomized into groups of 7-10 mice each and received a single intravenous injection of the ADCs. Tumors and body weights of mice are measured 1-2 times a week throughout the study. Mice are promptly euthanized when body weight loss is >20% of their starting weight. All animals are euthanized before tumors reached 3000 mm3 or showed signs of impending ulceration.

4. The efficacy of the anti-Her2 antibody-drug conjugates (ADCs) is investigated in a mouse allograft model of MMTV-HER2 Founder #5 (murine mammary tumor). The MMTV-HER2 Founder #5 (Fo5) model (developed at Genentech) is a transgenic mouse model in which the human HER2 gene, under transcriptional regulation of the murine mammary tumor virus promoter (MMTV-HER2), is overexpressed in mammary epithelium. The overexpression causes spontaneous development of mammary tumors that overexpress the human HER2 receptor. The mammary tumor from one of the founder animals (founder #5, Fo5) has been propagated in FVB mice (Charles River Laboratories) by serial transplantation of tumor fragments.

For efficacy studies, the Fo5 transgenic mammary tumor is surgically transplanted into the thoracic mammary fat pad of female nu/nu mice (Charles River Laboratories; Hollister, Calif.) as tumor fragments of approximately 2 mm×2 mm in size. When the allograft tumors reached an average tumor volume of 100-300 mm3 (referred to as Day 0), animals are randomized into groups of 7-10 mice each and received a single intravenous injection of the ADCs. Tumors and body weights of mice are measured 1-2 times a week throughout the study. Mice are promptly euthanized when body weight loss is >20% of their starting weight. All animals are euthanized before tumors reached 3000 mm3 or showed signs of impending ulceration.

Biological Data
ADC Linker-Drug Structures

| Example | Corresponding ADC | Structure | Name |
|---|---|---|---|
| PBD-LD1 | Napi3b PBD ADC1-1 | 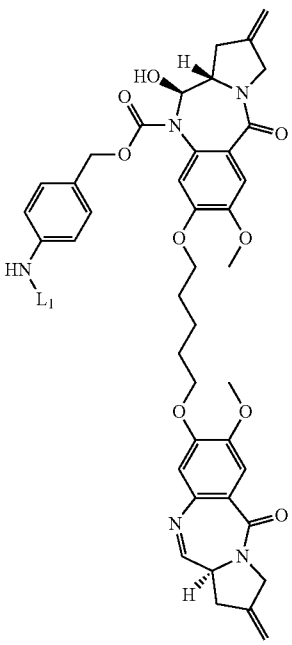 | $L_1$ is a cleavable linker |

-continued

| Example | Corresponding ADC | Structure | Name |
|---|---|---|---|
| PBD-LD2 | Napi3b PBD ADC2-1, CD33 CBI-PBD-ADC2-2, MUV16 PBD ADC2-4 | 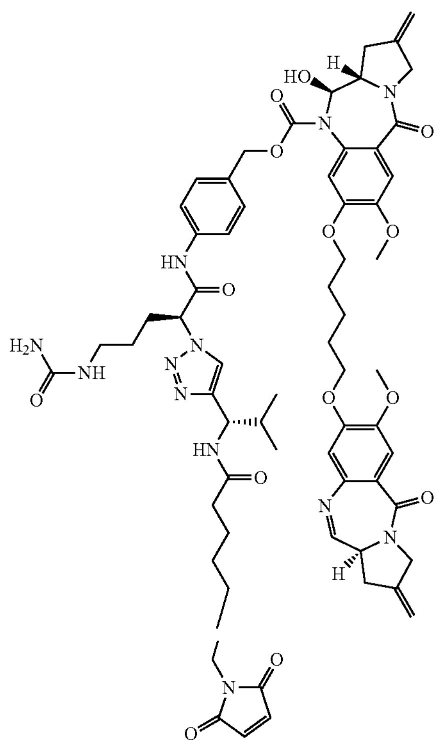 | [4-[[(2S)-2-[4-[(1S)-1-[6-(2,5-dioxopyrrol-1-yl)hexanoylamino]-2-methyl-propyl]triazol-1-yl]-5-ureido-pentanoyl]amino]phenyl]methyl(6S,6aS)-3-[5-[[(6aS)-2-methoxy-8-methylene-11-oxo-7,9-dihydro-6aH-pyrrolo[2,1-c][1,4]benzodiazepin-3-yl]oxy]pentoxy]-6-hydroxy-2-methoxy-8-methylene-11-oxo-6,6a,7,9-tetrahydropyrrolo[2,1-c][1,4]benzodiazepine-5-carboxylate |
| PBD-LD3 | Napi3b PBD ADC3-1 and CD33 CBI-PBD ADC3-2 | 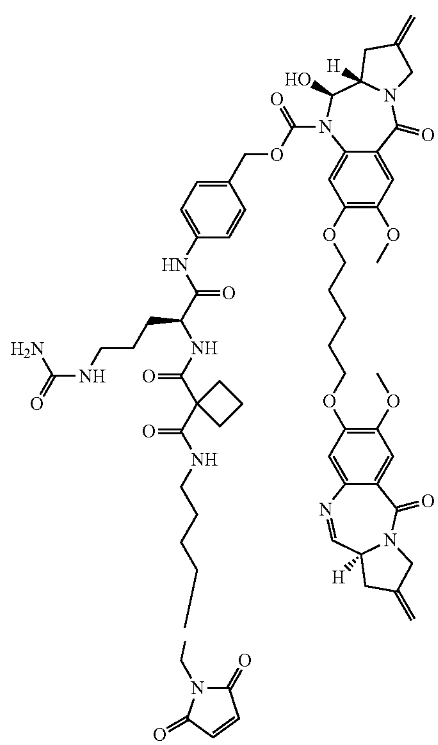 | [4-[[(2S)-2-[[1-[5-(2,5-dioxopyrrol-1-yl)pentylcarbamoyl]cyclobutanecarbonyl]amino]-5-ureido-pentanoyl]amino]phenyl]methyl(6S,6aS)-3-[5-][(6aS)-2-methoxy-8-methylene-11-oxo-7,9-dihydro-6aH-pyrrolo[2,1-c][1,4]benzodiazepin-3-yl]oxy]pentoxy]-6-hydroxy-2-methoxy-8-methylene-11-oxo-6,6a,7,9-tetrahydropyrrolo[2,1-c][1,4]benzodiazepine-5-carboxylate |

PBD-LD1 is compound 87 of WO 2011/130598.

Sequences

NaPi3b Humanized Antibody:

In one embodiment, the Napi3b antibody of ADCs of the present invention comprises three light chain hypervariable regions and three heavy chain hypervariable regions (SEQ ID NO: 1-6), the sequences of which are shown below.

In one embodiment, the Napi3b antibody of ADCs of the present invention comprises the variable light chain sequence of SEQ ID NO: 7 and the variable heavy chain sequence of SEQ ID NO: 8 In one embodiment, the NaPi3b antibody of ADCs of the present invention comprises the light chain sequence of SEQ ID NO: 9 and the heavy chain sequence of SEQ ID NO: 10

| | | |
|---|---|---|
| 10H1.11.4B HVR-L1 | RSSETLVHSSGNTYLE | Seq ID No: 1 |
| 10H1.11.4B HVR-L2 | RVSNRFS | Seq ID No: 2 |
| 10H1.11.4B HVR-L3 | FQGSFNPLT | Seq ID No: 3 |
| 10H1.11.4B HVR-H1 | GFSFSDFAMS | Seq ID No: 4 |
| 10H1.11.4B HVR-H2 | ATIGRVAFHTYYPDSMKG | Seq ID No: 5 |
| 10H1.11.4B HVR-H3 | ARHRGFDVGHFDF | Seq ID No: 6 |
| 10H1.11.4B $V_L$ | DIQMTQSPSSLSASVGDRVTITCRSS ETLVHSSGNTYLEWYQQKPGKAPKLL IYRVSNRFSGVPSRFSGSGSGTDFTL TISSLQPEDFATYYCFQGSFNPLTFG QGTKVEIKR | SEQ ID NO: 7 |
| 10H1.11.4B $V_H$ | EVQLVESGGGLVQPGGSLRLSCAASG FSFSDFAMSWVRQAPGKGLEWVATIG RVAFHTYYPDSMKGRFTISRDNSKNT LYLQMNSLRAEDTAVYYCARHRGFDV GHFDFWGQGTLVTVSS | SEQ ID NO: 8 |
| 10H1.11.4B Light Chain | DIQMTQSPSSLSASVGDRVTITCRSS ETLVHSSGNTYLEWYQQKPGKAPKLL IYRVSNRFSGVPSRFSGSGSGTDFTL TISSLQPEDFATYYCFQGSFNPLTFG QGTKVEIKRTVAAPSVFIFPPSDEQL KSGTASVVCLLNNFYPREAKVQWKVD NALQSGNSQESVTEQDSKDSTYSLSS TLTLSKADYEKHKVYACEVTHQGLSS PVTKSFNRGEC | SEQ ID NO: 9 |
| 10H1.11.4B Heavy Chain | EVQLVESGGGLVQPGGSLRLSCAASG FSFSDFAMSWVRQAPGKGLEWVATIG RVAFHTYYPDSMKGRFTISRDNSKNT LYLQMNSLRAEDTAVYYCARHRGFDV GHFDFWGQGTLVTVSSCSTKGPSVFP LAPSSKSTSGGTAALGCLVKDYFPEP VTVSWNSGALTSGVHTFPAVLQSSGL YSLSSVVTVPSSSLGTQTYICNVNHK PSNTKVDKKVEPKSCDKTHTCPPCPA PELLGGPSVFLFPPKPKDTLMISRTP EVTCVVVDVSHEDPEVKFNWYVDGVE VHNAKTKPREEQYNSTYRVVSVLTVL HQDWLNGKEYKCKVSNKALPAPIEKT ISKAKGQPREPQVYTLPPSREEMTKN QVSLTCLVKGFYPSDIAVEWESNGQP ENNYKTTPPVLDSDGSFFLYSKLTVD KSRWQQGNVFSCSVMHEALHNHYTQK SLSLSPGK | SEQ ID NO: 10 |

Anti-CD33 Humanized Antibody:

In one embodiment, the anti-CD33 antibody of ADCs of the present invention comprises three light chain hypervariable regions and three heavy chain hypervariable regions, the sequences (SEQ ID NO: 11-16) of which are shown below In one embodiment, the anti-CD33 antibody of ADCs of the present invention comprises the variable light chain sequence of SEQ ID NO: 17 and the variable heavy chain sequence of SEQ ID NO: 18

| | | |
|---|---|---|
| 15G15.33-HVR L1 | RSSQSLLHSNGYNYLD | SEQ ID NO: 11 |
| 15G15.33-HVR L2 | LGVNSVS | SEQ ID NO: 12 |
| 15G15.33-HVR L3 | MQALQTPWT | SEQ ID NO: 13 |
| 15G15.33-HVR H1 | NHAIS | SEQ ID NO: 14 |
| 15G15.33-HVR H2 | GIIPIFGTANYAQKFQG | SEQ ID NO: 15 |
| 15G15.33-HVR H3 | EWADVFDI | SEQ ID NO: 16 |
| 15G15.33 $V_L$ | EIVLTQSPLSLPVTPGEPASISCRSS QSLLHSNGYNYLDWYLQKPGQSPQLL IYLGVNSVSGVPDRFSGSGSGTDFTL KISRVEAEDVGVYYCMQALQTPWTFG QGTKVEIK | SEQ ID NO: 17 |
| 15G15.33 $V_H$ | QVQLVQSGAEVKKPGSSVKVSCKASG GIFSNHAISWVRQAPGQGLEWMGGII PIFGTANYAQKFQGRVTITADESTST AFMELSSLRSEDTAVYYCAREWADVF DIWGQGTMVTVSS | SEQ ID NO: 18 |

In one embodiment, the anti-CD33 antibody of ADCs of the present invention comprises the light chain sequence of SEQ ID NO: 19 and the heavy chain sequence of SEQ ID NO: 20

In one embodiment, the anti-CD33 antibody of ADCs of the present invention comprises three light chain hypervariable regions and three heavy chain hypervariable regions, the sequences (Seq ID NO: 19-24) of which are shown below.

In one embodiment, the anti-CD33 antibody of ADCs of the present invention comprises the variable light chain sequence of SEQ ID NO: 25 and the variable heavy chain sequence of SEQ ID NO: 26

In one embodiment, the anti-CD33 antibody of ADCs of the present invention comprises the variable light chain sequence of SEQ ID NO: 27 and the variable heavy chain sequence of SEQ ID NO: 28

In one embodiment, the anti-CD33 antibody of ADCs of the present invention comprises the variable light chain sequence of SEQ ID NO: 29 and the variable heavy chain sequence of SEQ ID NO: 30

In one embodiment, the anti-CD33 antibody of ADCs of the present invention comprises the variable light chain sequence of SEQ ID NO: 31 and the variable heavy chain sequence of SEQ ID NO: 32

| | | |
|---|---|---|
| 9C3-HVR L1 | RASQGIRNDLG | Seq ID NO: 19 |
| 9C3-HVR L2 | AASSLQS | Seq ID NO: 20 |
| 9C3-HVR L3 | LQHNSYPWT | Seq ID NO: 21 |

-continued

| | | |
|---|---|---|
| 9C3-HVR H1 | GNYMS | Seq ID NO: 22 |
| 9C3-HVR H2 | LIYSGDSTYYADSVKG | Seq ID NO: 23 |
| 9C3-HVR H3 | DGYYVSDMVV | Seq ID NO: 24 |
| 9C3 $V_L$ | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKLEIK | Seq ID NO: 25 |
| 9C3 $V_H$ | EVQLVESGGALIQPGGSLRLSCVASGFTISGNYMSWVRQAPGKGLEWVSLIYSGDSTYYADSVKGRFNISRDISKNTVYLQMNSLRVEDTAVYYCVRDGYYVSDMVVWGKGTTVTVSS | Seq ID NO: 26 |
| 9C3.2 $V_L$ | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKLEIK | Seq ID NO: 27 |
| 9C3.2 $V_H$ | EVQLVESGGALIQPGGSLRLSCVASGFTISGNYMSWVRQAPGKGLEWVSLIYSGDSTYYADSVKGRFTISRDISKNTVYLQMNSLRVEDTAVYYCVRDGYYVSDMVVWGKGTTVTVSS | Seq ID NO: 28 |
| 9C3.3 $V_L$ | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKLEIK | Seq ID NO: 29 |
| 9C3.3 $V_H$ | EVQLVESGGALIQPGGSLRLSCVASGFTISGNYMSWVRQAPGKGLEWVSLIYSGDSTYYADSVKGRFSISRDISKNTVYLQMNSLRVEDTAVYYCVRDGYYVSDMVVWGKGTTVTVSS | Seq ID NO: 30 |
| 9C3.4 $V_L$ | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKLEIK | Seq ID NO: 31 |
| 9C3.4 $V_H$ | EVQLVESGGALIQPGGSLRLSCVASGFTISGNYMSWVRQAPGKGLEWVSLIYSGDSTYYADSVKGRFAISRDISKNTVYLQMNSLRVEDTAVYYCVRDGYYVSDMVVWGKGTTVTVSS | Seq ID NO: 32 |

ADC In Vitro Data

The following ADCs were tested in in vitro assays described above and were found to be active. The activities of said ADCs are illustrated in the table below.

| Code | Antibody ID | EOL-1 $IC_{50}$ (ng/mL) |
|---|---|---|
| Napi3b PBD ADC1-1 | 10H1.11.4B | NA |
| gD PBD ADCI-3 | | NA |
| Napi3b PBD ADC2-1 | 10H1.11.4B | NA |
| CD33 PBD ADC2-2 | 15G15.33 | 0.49 |
| MUC16 PBD ADC2-4 | | 196.3 |
| Napi3b PBD ADC3-1 | 10H1.11.4B | 65.2 |
| CD33 PBD ADC3-2 | 15G15.33 | 0.18 |

ADC In Vivo Data

The following ADCs were tested in in vivo assays described above and were found to be active. The activities of said ADCs are illustrated in FIGS. 1-3 and the description below.

FIG. 1 shows efficacy comparison of NaPi3b ADCs in SCID-beige mice with OVCAR3X2.1 human ovarian tumors. NaPi3b PBD ADC1-1 and ADC2-1 both showed dose-dependent inhibition of tumor growth compared with vehicle group. The non-targeting control gD or CD33 PBD ADCs had a noticeable effect on the tumor growth; however, the effect of the corresponding NaPi3b PBD ADCs at the matching dose was superior.

FIG. 2 shows efficacy comparison of NaPi3b ADCs in SCID-beige mice with OVCAR3X2.1 human ovarian tumors. NaPi3b PBD ADC1-1 and ADC3-1 both showed inhibition of tumor growth compared with vehicle group. The non-targeting control CD33 PBD ADC3-2 had minimal effect on the tumor growth.

FIG. 3 shows efficacy of CD33 PBD ADC2-2 at various doses in SCID mice with EOL-1 human acute myeloid leukemia tumors. CD33 PBD ADC2-2 demonstrated dose-dependent inhibition of tumor growth; led to tumor stasis at antibody dose of 0.2 mg/kg and tumor remission at 0.5 mg/kg or higher.

The invention claimed is:

1. A non-peptide compound of Formula (IV) or Formula (V):

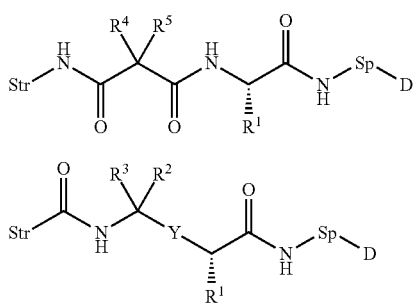

wherein

Str is a stretcher unit which can be covalently attached to an antibody;

Sp is a bond or a spacer unit covalently attached to a drug moiety;

Y is selected from:

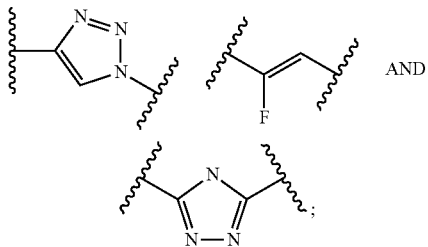

$R^1$ is $C_1$-$C_{10}$alkyl, ($C_1$-$C_{10}$alkyl)NHC(NH)NH$_2$ or ($C_1$-$C_{10}$alkyl)NHC(O)NH$_2$;

$R^3$ and $R^2$ are each independently H, $C_1$-$C_{10}$alkyl, arylalkyl or heteroarylalkyl, or $R^3$ and $R^2$ together may form a $C_3$-$C_7$cycloalkyl;

$R^4$ and $R^5$ form a $C_3$-$C_7$cycloalkyl ring;

D is a drug moiety of formula A or of formula B:

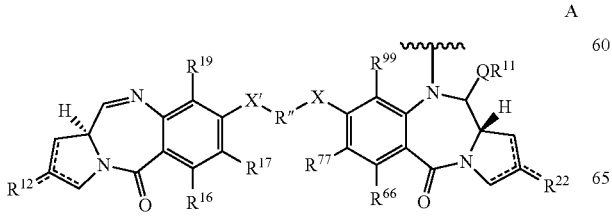

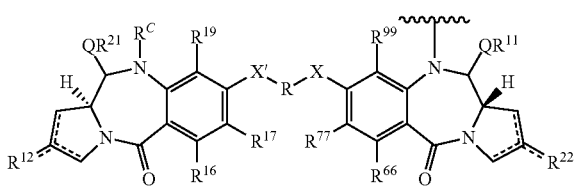

or a pharmaceutically acceptable salt thereof, wherein:

the wavy line indicates the covalent attachment site to the linker;

the dotted lines indicate the optional presence of a double bond between C1 and C2 or C2 and C3;

$R^{22}$ is independently selected from H, OH, =O, =CH$_2$, CN, R''', O R''', =CH—R$^D$, =C(R$^D$)$_2$, O—SO$_2$—$_R'''$, CO$_2$ R''' and CO R''', and optionally further selected from halo or dihalo, wherein $R^D$ is independently selected from R''', CO$_2$ R''', CO R''', CHO, CO$_2$H, and halo;

$R^{66}$ and $R^{99}$ are independently selected from H, R''', OH, O R''', SH, S R''', NH$_2$, NH R''', N R''' R$^P$, NO$_2$, Me$_3$Sn and halo;

$R^{77}$ is independently selected from H, R''', OH, O R''', SH, S R''', NH$_2$, NH R''', N R''' R$^P$, NO$_2$, Me$_3$Sn and halo;

Q is independently selected from O, S and NH;

$R^{11}$ is either H, or R''' or, where Q is O, SO$_3$M, where M is a metal cation;

R''' and R$^P$ are each independently selected from optionally substituted $C_{1-8}$ alkyl, $C_2$-$C_8$alkenyl, $C_2$-$C_8$ alkynyl, $C_3$-$C_8$ cycloalyl, $C_{3-8}$ heterocyclyl, $C_{5-20}$ aryl and $C_{5-20}$ heteroaryl groups, and optionally in relation to the group N R''' R$^P$, R'''and R$^P$ together with the nitrogen atom to which they are attached form an optionally substituted 4-, 5-, 6- or 7-membered heterocyclic ring;

$R^{12}$, $R^{16}$, $R^{19}$, $R^{21}$ and$R^{17}$ are as defined for $R^{22}$, $R^{66}$, $R^{99}$, $R^{11}$ and $R^{77}$ respectively;

R'' is a $C_3$-$C_{12}$ alkylene group, which chain may be interrupted by one or more heteroatoms selected from O, S, N(H), or NMe or aromatic rings, which rings are optionally substituted;

X and X' are independently selected from O, S and N(H); and $R^C$ is a capping group.

2. The compound of claim 1 represented by one of the following formulae:

(a)(i)

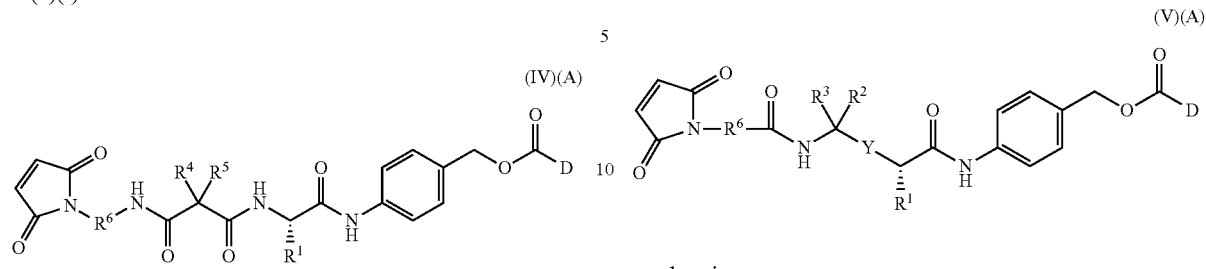

wherein $R^6$ is $C_1$-$C_{10}$alkylene;

(a)(ii)

(V)(A)

wherein
$R^6$ is $C_1$-$C_{10}$alkylene;

(b)(i)

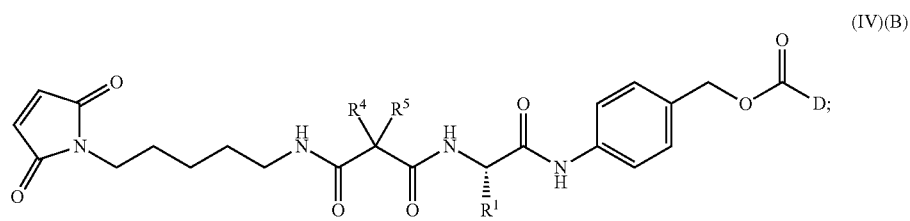

(IV)(B)

(b)(ii)

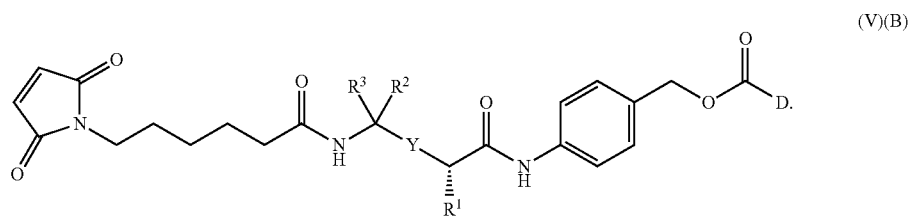

(V)(B)

3. The non-peptide compound of claim 1 wherein $C_3$-$C_7$cycloalkyl is cyclobutyl.

4. The non-peptide compound of claim 1 wherein $R^1$ of Formula (IV) or Formula (V) is $CH_2CH_2CH_2NHC(O)NH_2$.

5. The non-peptide compound of claim 1 wherein Str is:

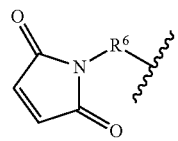

where $R^6$ is $C_1$-$C_{10}$ alkylene.

6. The non-peptide compound of claim 1 wherein Sp has the structure:

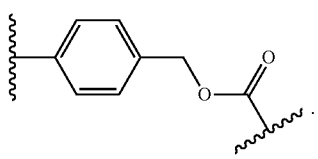 [SMILES: *C(=O)OCc1ccc(*)cc1]

7. The non-peptide compound of claim 1 selected from:
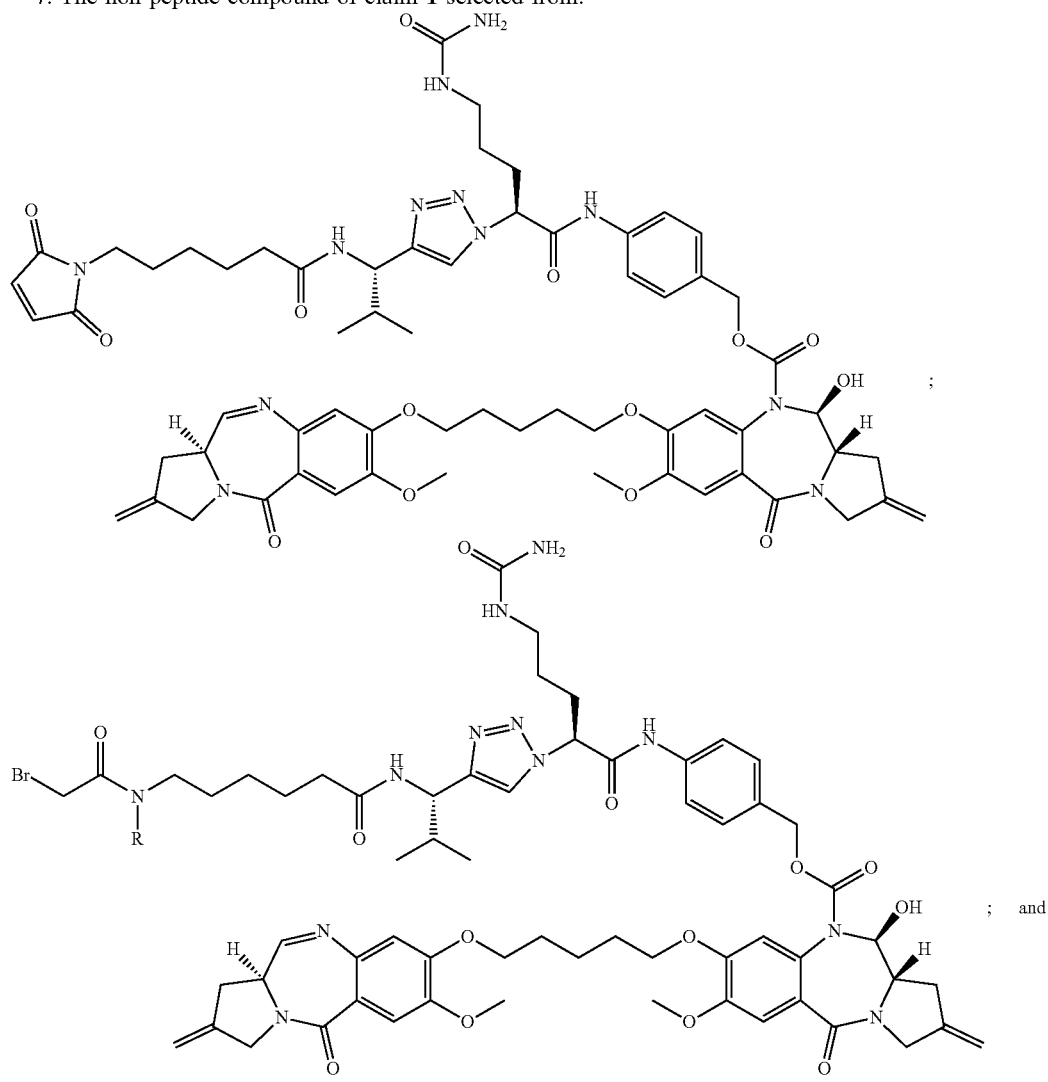
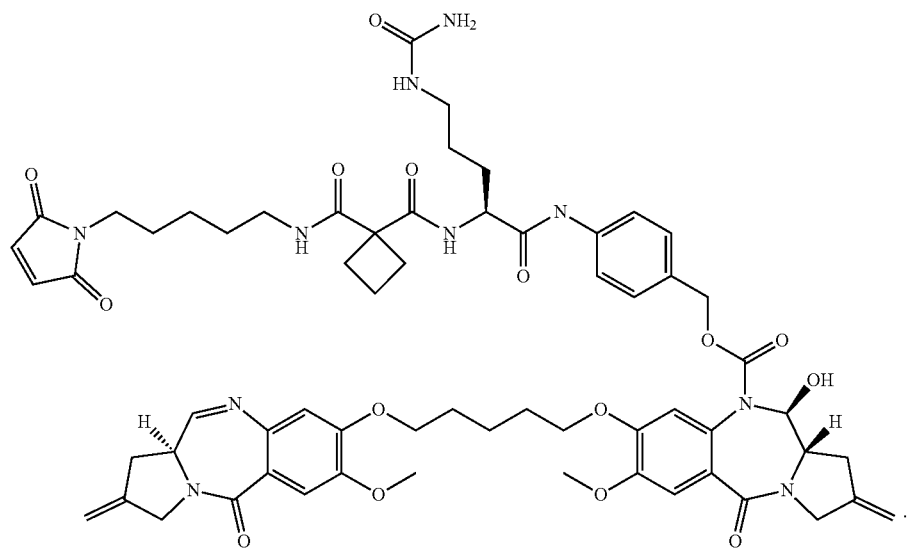
* * * * *

UNITED STATES PATENT AND TRADEMARK OFFICE
CERTIFICATE OF CORRECTION

PATENT NO. : 10,533,058 B2
APPLICATION NO. : 15/104388
DATED : January 14, 2020
INVENTOR(S) : John Flygare et al.

Page 1 of 1

It is certified that error appears in the above-identified patent and that said Letters Patent is hereby corrected as shown below:

In the Claims

In Claim 1, Column 130, Line 30 reads:
"$O\text{-}SO_2\text{-}{}_R{}^m$, $CO_2\ R^m$ and $CO\ R^m$, and optionally further"

However, it should read:
"$O\text{-}SO_2\text{-}R^m$, $CO_2\ R^m$ and $CO\ R^m$, and optionally further"

Signed and Sealed this
Third Day of March, 2020

Andrei Iancu
*Director of the United States Patent and Trademark Office*

SEQUENCE LISTING

<160> NUMBER OF SEQ ID NOS: 32

<210> SEQ ID NO 1
<211> LENGTH: 16
<212> TYPE: PRT
<213> ORGANISM: Artificial sequence
<220> FEATURE:
<223> OTHER INFORMATION: Synthetic construct: NaPi3b humanized antibody, light chain hypervariable region

<400> SEQUENCE: 1

Arg Ser Ser Glu Thr Leu Val His Ser Ser Gly Asn Thr Tyr Leu Glu
1               5                   10                  15

```
<210> SEQ ID NO 2
<211> LENGTH: 7
<212> TYPE: PRT
<213> ORGANISM: Artificial sequence
<220> FEATURE:
<223> OTHER INFORMATION: Synthetic construct: NaPi3b humanized antibody,
      light chain hypervariable region

<400> SEQUENCE: 2

Arg Val Ser Asn Arg Phe Ser
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic construct: NaPi3b humanized antibody,
      light chain hypervariable region

<400> SEQUENCE: 3

Phe Gln Gly Ser Phe Asn Pro Leu Thr
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic construct: NaPi3b humanized antibody,
      heavy chain hypervariable region

<400> SEQUENCE: 4

Gly Phe Ser Phe Ser Asp Phe Ala Met Ser
1               5                   10

<210> SEQ ID NO 5
<211> LENGTH: 18
<212> TYPE: PRT
<213> ORGANISM: Artificial sequence
<220> FEATURE:
<223> OTHER INFORMATION: Synthetic construct: NaPi3b humanized antibody,
      heavy chain hypervariable region

<400> SEQUENCE: 5

Ala Thr Ile Gly Arg Val Ala Phe His Thr Tyr Tyr Pro Asp Ser Met
1               5                   10                  15

Lys Gly

<210> SEQ ID NO 6
<211> LENGTH: 13
<212> TYPE: PRT
<213> ORGANISM: Artificial sequence
<220> FEATURE:
<223> OTHER INFORMATION: Synthetic construct: NaPi3b humanized antibody,
      heavy chain hypervariable region

<400> SEQUENCE: 6

Ala Arg His Arg Gly Phe Asp Val Gly His Phe Asp Phe
1               5                   10

<210> SEQ ID NO 7
<211> LENGTH: 113
<212> TYPE: PRT
<213> ORGANISM: Artificial sequence
<220> FEATURE:
<223> OTHER INFORMATION: Synthetic construct: NaPi3b humanized antibody,
      variable light chain sequence
```

```
<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg

<210> SEQ ID NO 8
<211> LENGTH: 120
<212> TYPE: PRT
<213> ORGANISM: Artificial sequence
<220> FEATURE:
<223> OTHER INFORMATION: Synthetic construct: NaPi3b humanized antibody,
      variable heavy chain sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser
        115                 120

<210> SEQ ID NO 9
<211> LENGTH: 219
<212> TYPE: PRT
<213> ORGANISM: Artificial sequence
<220> FEATURE:
<223> OTHER INFORMATION: Synthetic construct: NaPi3b humanized antibody,
      light chain sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45
```

```
Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 450
<212> TYPE: PRT
<213> ORGANISM: Artificial sequence
<220> FEATURE:
<223> OTHER INFORMATION: Synthetic construct: NaPi3b humanized antibody,
      heavy chain sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser Cys Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 11
<211> LENGTH: 16
<212> TYPE: PRT
<213> ORGANISM: Artificial sequence
<220> FEATURE:
<223> OTHER INFORMATION: Synthetic construct: Anti-CD33 humanized
      antibody, light chain hypervariable region

<400> SEQUENCE: 11

Arg Ser Ser Gln Ser Leu Leu His Ser Asn Gly Tyr Asn Tyr Leu Asp
1               5                   10                  15

<210> SEQ ID NO 12
<211> LENGTH: 7
<212> TYPE: PRT
<213> ORGANISM: Artificial sequence
<220> FEATURE:
<223> OTHER INFORMATION: Synthetic construct: Anti-CD33 humanized
      antibody, light chain hypervariable region

<400> SEQUENCE: 12

Leu Gly Val Asn Ser Val Ser
1               5

```
<210> SEQ ID NO 13
<211> LENGTH: 9
<212> TYPE: PRT
<213> ORGANISM: Artificial sequence
<220> FEATURE:
<223> OTHER INFORMATION: Synthetic construct: Anti-CD33 humanized
      antibody, light chain hypervariable region

<400> SEQUENCE: 13

Met Gln Ala Leu Gln Thr Pro Trp Thr
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic construct: Anti-CD33 humanized
      antibody, heavy chain hypervariable region

<400> SEQUENCE: 14

Asn His Ala Ile Ser
1               5

<210> SEQ ID NO 15
<211> LENGTH: 17
<212> TYPE: PRT
<213> ORGANISM: Artificial sequence
<220> FEATURE:
<223> OTHER INFORMATION: Synthetic construct: Anti-CD33 humanized
      antibody, heavy chain hypervariable region

<400> SEQUENCE: 15

Gly Ile Ile Pro Ile Phe Gly Thr Ala Asn Tyr Ala Gln Lys Phe Gln
1               5                   10                  15

Gly

<210> SEQ ID NO 16
<211> LENGTH: 8
<212> TYPE: PRT
<213> ORGANISM: Artificial sequence
<220> FEATURE:
<223> OTHER INFORMATION: Synthetic construct: Anti-CD33 humanized
      antibody, heavy chain hypervariable region

<400> SEQUENCE: 16

Glu Trp Ala Asp Val Phe Asp Ile
1               5

<210> SEQ ID NO 17
<211> LENGTH: 112
<212> TYPE: PRT
<213> ORGANISM: Artificial sequence
<220> FEATURE:
<223> OTHER INFORMATION: Synthetic construct: Anti-CD33 humanized
      antibody, variable light chain sequence

<400> SEQUENCE: 17

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Phe Gly Gln Gly Thr Lys Val Glu Ile Lys
            100                 105                 110

<210> SEQ ID NO 18
<211> LENGTH: 117
<212> TYPE: PRT
<213> ORGANISM: Artificial sequence
<220> FEATURE:
<223> OTHER INFORMATION: Synthetic construct: Anti-CD33 humanized
      antibody, variable heavy chain sequence

<400> SEQUENCE: 18

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Ile Phe Ser Asn His
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Phe
 65                  70                  75                  80

Met Glu Leu Ser Ser Leu Arg Ser Glu Asp Thr Ala Val Tyr Tyr Cys
                 85                  90                  95

Ala Arg Glu Trp Ala Asp Val Phe Asp Ile Trp Gly Gly Thr Met
            100                 105                 110

Val Thr Val Ser Ser
        115

<210> SEQ ID NO 19
<211> LENGTH: 11
<212> TYPE: PRT
<213> ORGANISM: Artificial sequence
<220> FEATURE:
<223> OTHER INFORMATION: Synthetic construct: Anti-CD33 humanized
      antibody, light chain hypervariable region

<400> SEQUENCE: 19

Arg Ala Ser Gln Gly Ile Arg Asn Asp Leu Gly
 1               5                  10

<210> SEQ ID NO 20
<211> LENGTH: 7
<212> TYPE: PRT
<213> ORGANISM: Artificial sequence
<220> FEATURE:
<223> OTHER INFORMATION: Synthetic construct: Anti-CD33 humanized
      antibody, light chain hypervariable region

<400> SEQUENCE: 20

Ala Ala Ser Ser Leu Gln Ser
 1               5

<210> SEQ ID NO 21
<211> LENGTH: 9
<212> TYPE: PRT
<213> ORGANISM: Artificial sequence
```

```
<220> FEATURE:
<223> OTHER INFORMATION: Synthetic construct: Anti-CD33 humanized
      antibody, light chain hypervariable region

<400> SEQUENCE: 21

Leu Gln His Asn Ser Tyr Pro Trp Thr
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic construct: Anti-CD33 humanized
      antibody, heavy chain hypervariable region

<400> SEQUENCE: 22

Gly Asn Tyr Met Ser
1               5

<210> SEQ ID NO 23
<211> LENGTH: 16
<212> TYPE: PRT
<213> ORGANISM: Artificial sequence
<220> FEATURE:
<223> OTHER INFORMATION: Synthetic construct: Anti-CD33 humanized
      antibody, heavy chain hypervariable region

<400> SEQUENCE: 23

Leu Ile Tyr Ser Gly Asp Ser Thr Tyr Tyr Ala Asp Ser Val Lys Gly
1               5                   10                  15

<210> SEQ ID NO 24
<211> LENGTH: 10
<212> TYPE: PRT
<213> ORGANISM: Artificial sequence
<220> FEATURE:
<223> OTHER INFORMATION: Synthetic construct: Anti-CD33 humanized
      antibody, heavy chain hypervariable region

<400> SEQUENCE: 24

Asp Gly Tyr Tyr Val Ser Asp Met Val Val
1               5                   10

<210> SEQ ID NO 25
<211> LENGTH: 107
<212> TYPE: PRT
<213> ORGANISM: Artificial sequence
<220> FEATURE:
<223> OTHER INFORMATION: Synthetic construct: Anti-CD33 humanized
      antibody, variable light chain sequence

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 26
<211> LENGTH: 118
<212> TYPE: PRT
<213> ORGANISM: Artificial sequence
<220> FEATURE:
<223> OTHER INFORMATION: Synthetic construct: Anti-CD33 humanized
      antibody, variable heavy chain sequence

<400> SEQUENCE: 26

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Asn Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 27
<211> LENGTH: 107
<212> TYPE: PRT
<213> ORGANISM: Artificial sequence
<220> FEATURE:
<223> OTHER INFORMATION: Synthetic construct: Anti-CD33 humanized
      antibody, variable light chain sequence

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 28
<211> LENGTH: 118
<212> TYPE: PRT
<213> ORGANISM: Artificial sequence
```

```
<220> FEATURE:
<223> OTHER INFORMATION: Synthetic construct: Anti-CD33 humanized
      antibody, variable heavy chain sequence

<400> SEQUENCE: 28

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Thr Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 29
<211> LENGTH: 107
<212> TYPE: PRT
<213> ORGANISM: Artificial sequence
<220> FEATURE:
<223> OTHER INFORMATION: Synthetic construct: Anti-CD33 humanized
      antibody, variable light chain sequence

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 30
<211> LENGTH: 118
<212> TYPE: PRT
<213> ORGANISM: Artificial sequence
<220> FEATURE:
<223> OTHER INFORMATION: Synthetic construct: Anti-CD33 humanized
      antibody, variable heavy chain sequence

<400> SEQUENCE: 30

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30
```

```
Tyr Met Ser Trp Val Arg Gln Ala Pro Gly Lys Gly Leu Glu Trp Val
            35                  40                  45

Ser Leu Ile Tyr Ser Gly Asp Ser Thr Tyr Tyr Ala Asp Ser Val Lys
 50                  55                  60

Gly Arg Phe Ser Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
            85                  90                  95

Arg Asp Gly Tyr Tyr Val Ser Asp Met Val Val Trp Gly Lys Gly Thr
            100                 105                 110

Thr Val Thr Val Ser Ser
            115
```

<210> SEQ ID NO 31
<211> LENGTH: 107
<212> TYPE: PRT
<213> ORGANISM: Artificial sequence
<220> FEATURE:
<223> OTHER INFORMATION: Synthetic construct: Anti-CD33 humanized
      antibody, variable light chain sequence

<400> SEQUENCE: 31

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
            85                  90                  95

Thr Phe Gly Gln Gly Thr Lys Leu Glu Ile Lys
            100                 105
```

<210> SEQ ID NO 32
<211> LENGTH: 118
<212> TYPE: PRT
<213> ORGANISM: Artificial sequence
<220> FEATURE:
<223> OTHER INFORMATION: Synthetic construct: Anti-CD33 humanized
      antibody, variable heavy chain sequence

<400> SEQUENCE: 32

```
Glu Val Gln Leu Val Glu Ser Gly Gly Ala Leu Ile Gln Pro Gly Gly
 1               5                  10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
            35                  40                  45

Ser Leu Ile Tyr Ser Gly Asp Ser Thr Tyr Tyr Ala Asp Ser Val Lys
 50                  55                  60

Gly Arg Phe Ala Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
            85                  90                  95
```

```
Arg Asp Gly Tyr Tyr Val Ser Asp Met Val Val Trp Gly Lys Gly Thr
            100                 105                 110
Thr Val Thr Val Ser Ser
            115
```